United States Patent
Oliveira et al.

(10) Patent No.: US 12,094,587 B2
(45) Date of Patent: Sep. 17, 2024

(54) APPARATUS AND METHOD FOR IDENTIFICATION OF PRIMARY IMMUNE RESISTANCE IN CANCER PATIENTS

(71) Applicant: BIODESIX, INC., Boulder, CO (US)

(72) Inventors: Carlos Oliveira, Steamboat Springs, CO (US); Heinrich Roder, Steamboat Springs, CO (US); Joanna Roder, Steamboat Springs, CO (US)

(73) Assignee: Biodesix, Inc., Boulder, CO (US)

( * ) Notice: Subject to any disclaimer, the term of this patent is extended or adjusted under 35 U.S.C. 154(b) by 955 days.

(21) Appl. No.: 17/031,042

(22) PCT Filed: Mar. 11, 2019

(86) PCT No.: PCT/US2019/021641
§ 371 (c)(1),
(2) Date: Sep. 24, 2020

(87) PCT Pub. No.: WO2019/190732
PCT Pub. Date: Oct. 3, 2019

(65) Prior Publication Data
US 2021/0118538 A1    Apr. 22, 2021

Related U.S. Application Data

(60) Provisional application No. 62/649,762, filed on Mar. 29, 2018, provisional application No. 62/649,771, filed on Mar. 29, 2018.

(51) Int. Cl.
*G16H 20/10*    (2018.01)
*G01N 33/68*    (2006.01)
(Continued)

(52) U.S. Cl.
CPC ......... *G16H 20/10* (2018.01); *G01N 33/6848* (2013.01); *G06N 20/00* (2019.01);
(Continued)

(58) Field of Classification Search
None
See application file for complete search history.

(56) References Cited

U.S. PATENT DOCUMENTS

| | | | |
|---|---|---|---|
| 7,736,905 B2 | 6/2010 | Roder et al. |
| 7,858,389 B2 | 12/2010 | Roder et al. |

(Continued)

FOREIGN PATENT DOCUMENTS

| | | | |
|---|---|---|---|
| CN | 101201355 A | 6/2008 |
| CN | 103339509 A | 10/2013 |

(Continued)

OTHER PUBLICATIONS

Aliferis, Constantin F., Alexander Statnikov, and Ioannis T. Tsamardinos. "Challenges in the Analysis of Mass-Throughput Data: A Technical Commentary from the Statistical Machine Learning Perspective." Cancer Informatics 2 (2006): n/a. ProQuest. Web. Jun. 4, 2024. (Year: 2006).*

(Continued)

*Primary Examiner* — Lena Najarian
(74) *Attorney, Agent, or Firm* — Lathrop GPM LLP; Lisa Hillman

(57) ABSTRACT

Laboratory test apparatus for conducting a mass spectrometry test on a blood-based sample of a cancer patient includes a classification procedure implemented in a programmed computer that generates a class label. In one form of the test, "Test 1", if the sample is labelled "Bad" or equivalent the patient is predicted to exhibit primary immune resistance if they are later treated with anti-PD-1 or anti-PD-L1 therapies. In "Test 2" the Bad class label predicts that the patient will have a poor prognosis in response to treatment by either anti-PD-1 or anti-PD-L1 therapies or alternative chemotherapies, such as docetaxel or pemetrexed. "Test 3" identifies patients that are likely to have a poor prognosis in response to treatment by either anti-PD-1

(Continued)

or anti-PD-L1 therapies but have improved outcomes on alternative chemotherapies. A Good class label by either Test 1 or 2 predicts very good outcome on anti-PD-1 or anti-PD-L1 monotherapy.

19 Claims, 19 Drawing Sheets

(51) Int. Cl.

| | |
|---|---|
| G06N 20/00 | (2019.01) |
| G16B 40/20 | (2019.01) |
| G16H 50/20 | (2018.01) |
| H01J 49/00 | (2006.01) |
| H01J 49/16 | (2006.01) |
| H01J 49/44 | (2006.01) |

(52) U.S. Cl.
CPC ............. *G16B 40/20* (2019.02); *G16H 50/20* (2018.01); *H01J 49/0036* (2013.01); *H01J 49/164* (2013.01); *H01J 49/446* (2013.01)

(56) References Cited

U.S. PATENT DOCUMENTS

| | | | |
|---|---|---|---|
| 7,858,390 | B2 | 12/2010 | Roder et al. |
| 7,867,775 | B2 | 1/2011 | Roder et al. |
| 7,879,620 | B2 | 2/2011 | Roder et al. |
| 7,906,342 | B2 | 3/2011 | Roeder et al. |
| 8,024,282 | B2 | 9/2011 | Tsypin et al. |
| 8,097,469 | B2 | 1/2012 | Roder et al. |
| 8,119,417 | B2 | 2/2012 | Roeder et al. |
| 8,119,418 | B2 | 2/2012 | Roeder et al. |
| 8,467,988 | B1 | 6/2013 | Roder et al. |
| 8,586,379 | B2 | 11/2013 | Roeder et al. |
| 8,586,380 | B2 | 11/2013 | Roeder et al. |
| 8,718,996 | B2 | 5/2014 | Brauns et al. |
| 8,914,238 | B2 | 12/2014 | Roder et al. |
| 9,152,758 | B2 | 10/2015 | Roder et al. |
| 9,211,314 | B2 | 12/2015 | Roder et al. |
| 9,254,120 | B2 | 2/2016 | Roeder et al. |
| 9,279,798 | B2 | 3/2016 | Roder et al. |
| 9,477,906 | B2 | 10/2016 | Roder et al. |
| 9,563,744 | B1 | 2/2017 | Roder et al. |
| 9,606,101 | B2 | 3/2017 | Roder et al. |
| 9,724,413 | B2 | 8/2017 | Maecker et al. |
| 9,779,204 | B2 | 10/2017 | Roder et al. |
| 9,824,182 | B2 | 11/2017 | Roder et al. |
| 10,007,766 | B2 | 6/2018 | Roder et al. |
| 10,037,874 | B2 | 7/2018 | Roder et al. |
| 10,217,620 | B2 | 2/2019 | Roder et al. |
| 10,489,550 | B2 | 11/2019 | Roder et al. |
| 10,713,590 | B2 | 7/2020 | Roder et al. |
| 2003/0225526 | A1 | 12/2003 | Golub et al. |
| 2005/0149269 | A1 | 7/2005 | Thomas et al. |
| 2006/0088894 | A1* | 4/2006 | Wright ................ C12Q 1/6886 435/7.23 |
| 2007/0231921 | A1 | 10/2007 | Roder et al. |
| 2007/0269804 | A1 | 11/2007 | Liew et al. |
| 2008/0032299 | A1 | 2/2008 | Burczynski et al. |
| 2008/0306898 | A1 | 12/2008 | Tsyin et al. |
| 2010/0174492 | A1 | 7/2010 | Roder et al. |
| 2010/0240546 | A1 | 9/2010 | Lo |
| 2011/0208433 | A1* | 8/2011 | Grigorieva .............. A61P 43/00 702/19 |
| 2011/0271358 | A1 | 11/2011 | Freeman et al. |
| 2013/0131996 | A1 | 5/2013 | Roder et al. |
| 2013/0344111 | A1 | 12/2013 | Roder et al. |
| 2014/0044673 | A1 | 2/2014 | Caprioli |
| 2014/0200825 | A1 | 7/2014 | Roder et al. |
| 2014/0341902 | A1 | 11/2014 | Maecker et al. |
| 2015/0071910 | A1 | 3/2015 | Kowanetz et al. |
| 2015/0102216 | A1 | 4/2015 | Roder et al. |
| 2015/0125463 | A1 | 5/2015 | Cogswell et al. |
| 2015/0283206 | A1 | 10/2015 | Roder et al. |
| 2015/0285817 | A1 | 10/2015 | Roder et al. |
| 2016/0019342 | A1 | 1/2016 | Roder et al. |
| 2016/0098514 | A1 | 4/2016 | Roder et al. |
| 2016/0163522 | A1 | 6/2016 | Roder et al. |
| 2016/0018410 | A1 | 10/2016 | Roder et al. |
| 2016/0299146 | A1 | 10/2016 | Garraway et al. |
| 2017/0039345 | A1* | 2/2017 | Röder .................... G16B 40/10 |
| 2017/0271136 | A1 | 9/2017 | Roder et al. |
| 2018/0021431 | A1 | 1/2018 | Maecker et al. |
| 2018/0027249 | A1 | 9/2018 | Roder et al. |
| 2019/0018929 | A1 | 1/2019 | Steingrimsson et al. |
| 2019/0035364 | A1 | 11/2019 | Oliveira et al. |

FOREIGN PATENT DOCUMENTS

| | | | | |
|---|---|---|---|---|
| CN | 103384827 | A | 11/2013 | |
| CN | 103842030 | A | 6/2014 | |
| CN | 104470949 | A | 3/2015 | |
| CN | 104685360 | A | 6/2015 | |
| CN | 105512669 | A | 4/2016 | |
| CN | 105745659 | A | 7/2016 | |
| EP | 1043676 | A2 | 10/2000 | |
| EP | 2241335 | A1 | 10/2010 | |
| WO | WO-2005010492 | A2 * | 2/2005 | ............. G06F 19/24 |
| WO | 2010085234 | A1 | 7/2010 | |
| WO | 2012069462 | A1 | 5/2012 | |
| WO | 2014003853 | A1 | 1/2014 | |
| WO | 2014007859 | A1 | 1/2014 | |
| WO | 2014055543 | A2 | 4/2014 | |
| WO | 2014149629 | A1 | 9/2014 | |
| WO | 2015039021 | A2 | 3/2015 | |
| WO | 2015153991 | A1 | 10/2015 | |
| WO | 2015157109 | A1 | 10/2015 | |
| WO | 2015176033 | A1 | 11/2015 | |
| WO | 2016049385 | A1 | 3/2016 | |
| WO | 2016054031 | A1 | 4/2016 | |
| WO | 2016089553 | A1 | 6/2016 | |
| WO | 2017011439 | A1 | 1/2017 | |
| WO | 2017136139 | A1 | 8/2017 | |

OTHER PUBLICATIONS

Zwierzina, "ASCO 2013—new concepts and the path to individualized therapy", magazine of european medical oncology, vol. 6, pp. 251-253, Dec. 10, 2013.

Extended European Search Report in International Application No. 19775503.6, dated May 16, 2022, 12 pages.

Althammer et al, "Biomarkers and Immune Monitoring", Journal for Immunotherapy of Caner, vol. 4, No. 91, pp. 223-242, Dec. 8, 2016.

Biodesix's Diagnostic Cortex™ Platform Used in Three Studies Presented at SITC, Nov. 15, 2016, Retrieved from the Internet Oct. 26, 2020, URL: https://www.biodesix.com/press-releases/biodesixs-diagnostic-cortex-platform-used-three-studies-presented-sitc.

Blanco et al, "Feature selection in Bayesian classifiers for the prognosis of survival of cirrhotic patients treated with TIPS", Journal of Biomedical Informatics, vol. 38, pp. 376-388, (2005).

Bruno et al, "Overexpression of PD-1 and PD-L 1 in Penal Cell Carcinoma is associated with poor prognosis in metastatic patients treated with subtinib", Annals of Oncology, vol. 26, No. 2, Annual Meeting Poster, (2015).

Carvajal-Hausdorf et al, "Quantitative Measurement of Cancer Tissue Biomarkers in the Lab and in the Clinic", Lab Invest, vol. 95, No. 4, pp. 385-396, (2015).

International Search Report for corresponding PCT application No. PCT/US2019/021641, dated Jul. 3, 2019, 7 pages.

Girosi et al, "Regularization Theory and Neural Architectures", Neural Computation, vol. 7, pp. 219-269, (1995).

Grivennikov et al, "Immunity, inflammation, and cancer", Cell, vol. 140, pp. 883-899, (2010).

Gunn et al, "Opposing roles for complement component C5a in tumor progression and the tumor microenvironment", J Immunol, vol. 189, pp. 2985-2994, (2012).

(56) References Cited

OTHER PUBLICATIONS

International Search Report and Written Opinion for corresponding PCT Application No. PCT/US2016/041860 dated Oct. 6, 2016.
International Search Report for PCT application No. PCT/US17/13920, dated May 19, 2017.
International Search Report for PCT application No. PCT/US2018/12564, dated Mar. 26, 2018.
Janelle et al, "Role of the complement system in NK cell-mediated antitumor T-cell responses", Oncoimmunology, vol. 3, e27897, (2014).
Janelle et al, "Transient complement inhibition promotes a tumor-specific immune response through the implication of natural killer cells", Cancer Immunol Res, vol. 2, pp. 200-206, (2014).
Kani et al, "Quantitative Proteomic profiling identifies protein correlates to EGFR kinase inhibition", Mol Cancer Ther., Vo. 11, No. 5, pp. 1071-1081, (2012).
Karpievitch et al, "Liquid Chromatography Mass Spectrometry-Based Proteomics: Biological and Technological Aspects", Ann Appl Stat., vol. 4, No. 4, pp. 1797-1823, (2010).
Kennedy-Crispin et al, "Human keratinocytes' response to injury upregulates CCl20 and other genes linking innate and adaptive immunity", J Invest Dermatol., vol. 132, No. 1, pp. 105-113, (2012).
Larkin et al, "Combined Nivolumab and Ipilimumab or Monotherapy in Untreated Melanoma", The New England Journal of Medicine, vol. 373, No. 1, pp. 23-34, (2015).
Lundqvist et al, "Adoptive Cellular Therapy", Journal for Immunotherapy of Cancer, vol. 4, No. 82, pp. 1-221, Nov. 16, 2016.
Mantovani et al, "Cancer-related inflammation", Nature, vol. 454, pp. 436-444, (2008).
Markiewski et al, "Modulation of the antitumor immune response by complement", Natl Immunol, vol. 9, pp. 1225-1235, (2008).
Mathern et al, "Molecules Great and Small: The Complement System", Clin J Am Soc Nephrol, vol. 10, pp. 1636-1650, (2015).
McDeromott et al, "Durable benefit and the potential for long-term survival with immunotherapy in advanced melanoma", Cancer Treatment, vol. 40, No. 9, pp. 1056-1064, Apr. 8, 2014.
Mootha et al, "PGC-1 α-responsive genes involved in oxidative phosphorylation are coordinately downregulated in human diabetes", Nat Genet., vol. 34, No. 3, pp. 267-273, (2003).
Pearson et al, J. Clinical Oncology, vol. 34, No. 15, Meeting Abstract, May 2016.
Pio et al, "The role of complement in tumor growth", Adv Exp Med Biol, vol. 772, pp. 229-262, (2014).
Porta et al, "Cellular and molecular pathways linking inflammation and cancer", Immunobiology, vol. 214, pp. 461-777, (2009).
Postow et al, "Peripheral and tumor immune correlates in patients with advanced melanoma treated with nivolumab (aniti-PD-1, BMS-936558, ONO-4538) monotherapy or in combination with ipilimumab", Journal of Translational Medicine, vol. 12, No. 1, pp. 1-2, (2014).
Qi et al, "Advances in the study of serum tumor markers of lung cancer", Journal of Cancer and Therapeutics, vol. 10, No. 2, pp. C95-C101, (2014).
Redman et al, "Advances in immunotherapy for melanoma", BNC Medicine, vol. 14, No. 1, pp. 1-11, (2016).
Romano et al, "The therapeutic promise of disrupting the PD-1/PD-L1 immunie checkpoint in cancer: unleashing the CD8 cell mediated anti-tumor activity results in significant, unprecedented clinical efficacy in various solid tumors", J. ImmunoTher. Can., vol. 3, No. 15, pp. 1-5, (2015).
Shrivastava, "Improving Neural Networks with Dropout", Master's Thesis, Graduate Department of Computer Science, University of Toronto, (2013).
Subramanian et al, "Gene set enrichment analysis: A knowledge-based approach for interpreting genome-wide expression profiles", Proc Natl Acad Sci USA, vol. 102, No. 43, pp. 15545-15550, (2005).
Taguchi et al, "Mass Spectrometry to Classify Non-Small-Cell Lung Cancer Patients for Clinical Outcome after Treatment with Epidermal Growth Factor Receptor Tyrosine Kinase Inhibitors: A Multicohort Cross-Institutional Study", UNCI Journal of the National Cancer Institute, vol. 99, No. 11, pp. 838-846, (2007).
Taneja et al, "Markers of Small Cell Lung Cancer", World Journal of Surgical Oncology, vol. 2, No. 10, 5 pages, May 5, 2004.
Tibshirani, "Regression shrinkage and selection via the lasso", J. Royal. Statist. Soc B, vol. 58, No. 1, pp. 267-288, (1996).
Tikhonov, "On the stability of inverse problems", Doklady Akademii Nauk SSSR, vol. 39, No. 5, pp. 195-198, (1943).
Vadrevu et al, "Complement c5a receptor facilities cancer metastasis by altering T-cell responses in the metastatic niche", Cancer Res, vol. 74, pp. 3454-3565, (2014).
Vu et al, "RAC1 P29S regulates PD-L1 expression in melanoma", Pigment Cell Melanoma Res., vol. 28, No. 5, pp. 590-598, (2015).
Weber et al, "Pre-treatment selection for nivolumab benefit based on serum mass spectra", Journal for Immunotherapy of Cancer, No. 3, pp. 1-2, Nov. 4, 2015.
Weber et al, "A Serum Protein Signature Associated with Outcome After Anti-PD-1 Therapy in Metastatic Melanoma", ACCR Special Conference on Tumor Immunology and Immunotherapy, Boston, MA, vol. 6, No. 1, pp. 79-86, (2016).
Weber et al, "A test identifying advanced melanoma patients with long survival outcomes on nivolumab shows potential for selection for benefit from combination checkpoint blockade", 31st Annual Meeting and Associated Programs of the Society for Immunotherapy of Cancer, vol. 4, No. 82, (2016).
Weber et al, "Safety, Efficacy, Biomarkers of Nivoluamb With Vaccine in Ipilimumab or -Naïve Melanoma", J. Clin. Oncol., vol. 31, pp. 4311-4318, (2013).
Zhang et al, "A Protective Role for C5a in the Development of Allergic Asthma Associated with Altered Levels of B7-H1 and B7-DC on Plasmacytoid Dendritic Cells", J. Immunol., vol. 182, pp. 5123-5130, (2009).
Written Opinion of the International Searching Authority for corresponding PCT application No. PCT/US2019/021641, dated Jul. 3, 2019, 12 pages.

* cited by examiner

Example of features defined in the dataset

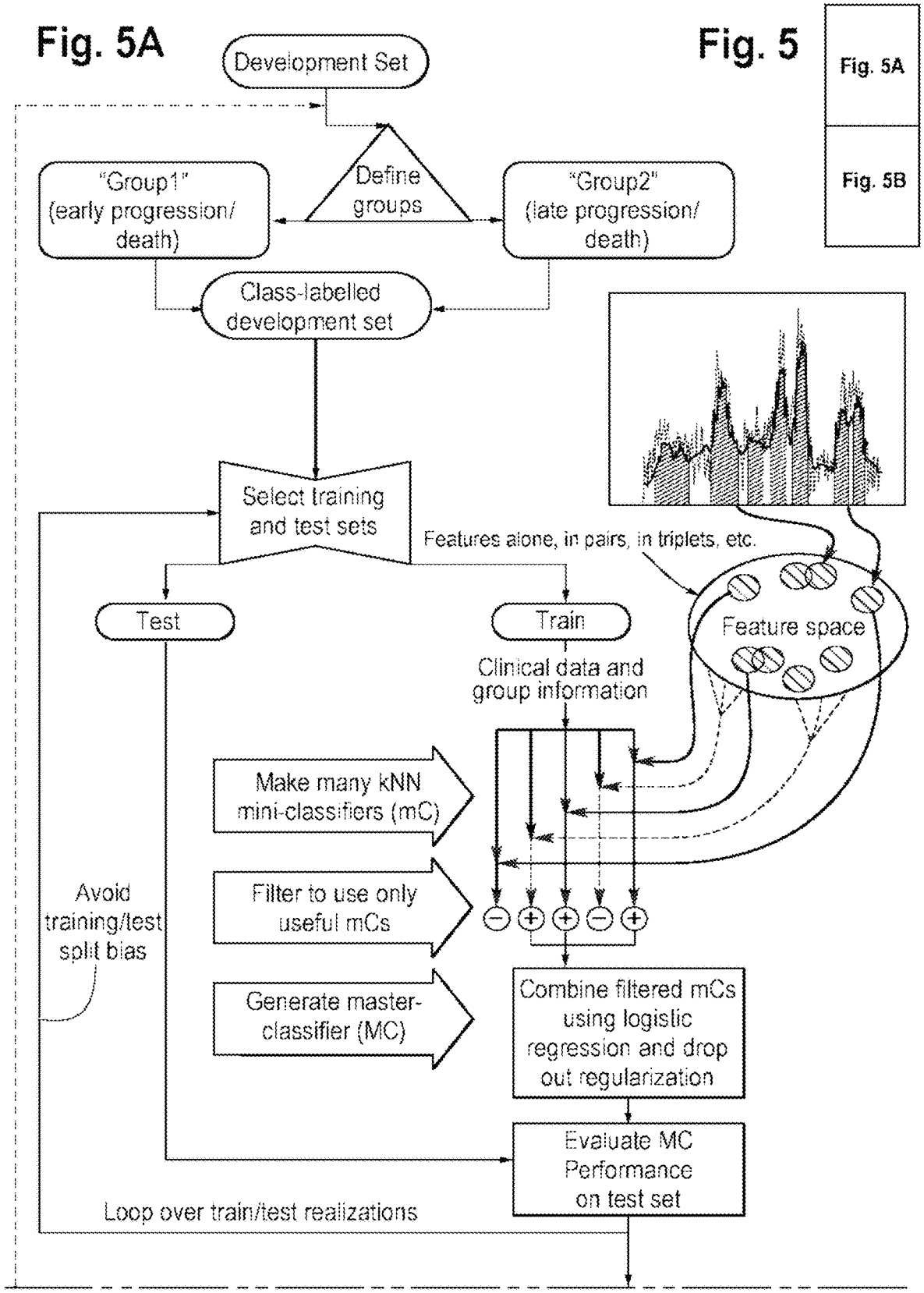

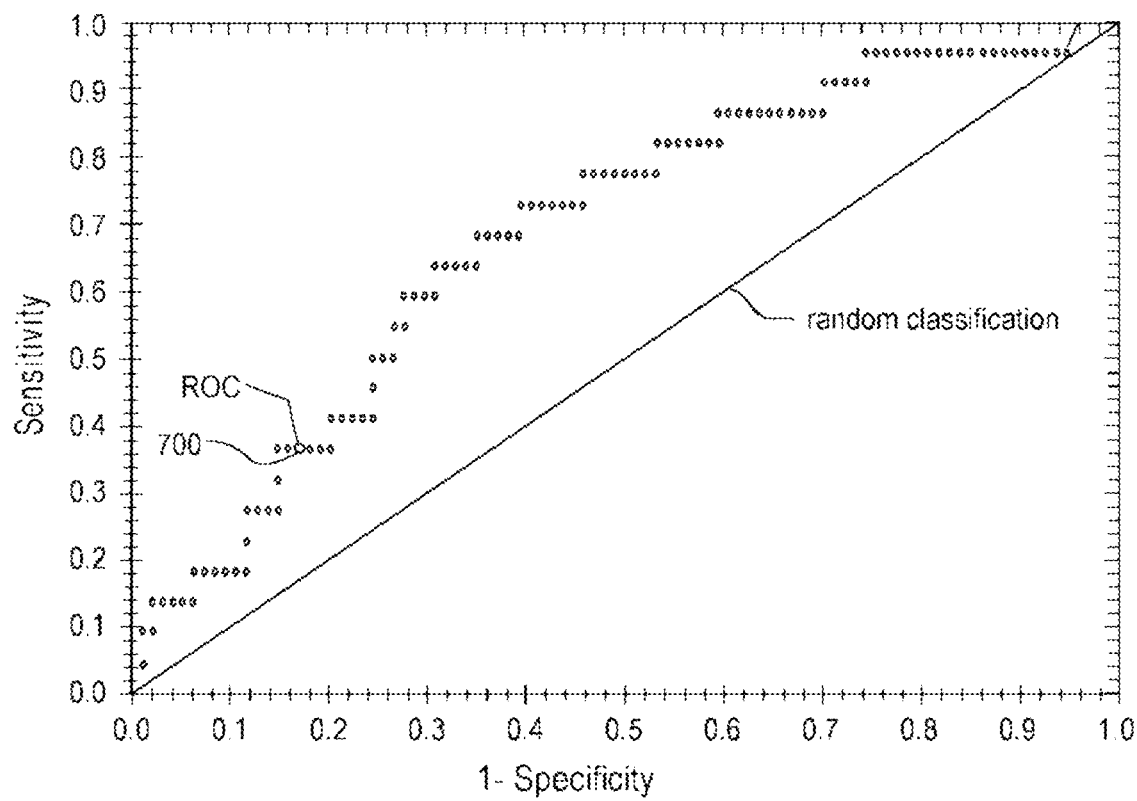

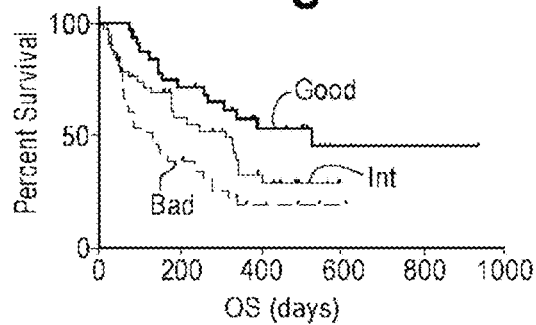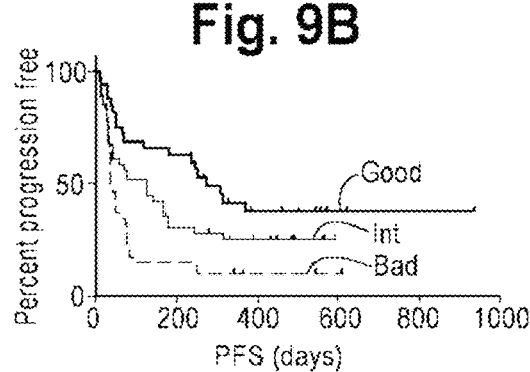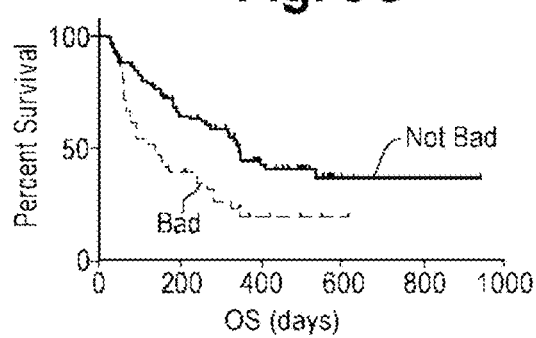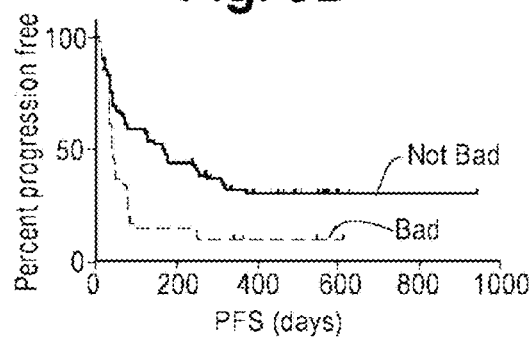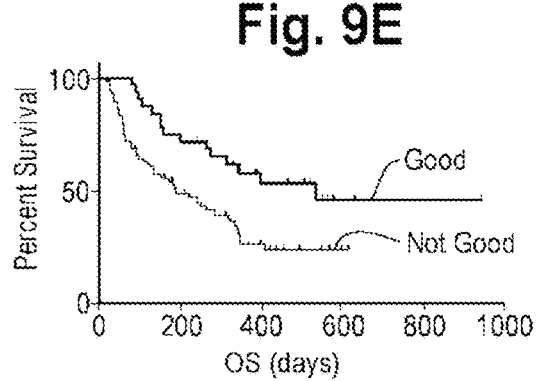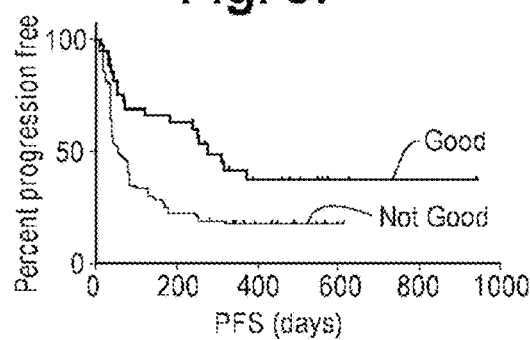

| HR (95% CI) [stratified by line] | 0.59 (0.35-0.97) |
| P value | 0.038 |
| OS Median (95% CI): Bad | 4.8 (2.9-9.3) months |
| OS Median (95% CI): Not Bad | 12.6 (7.4-17.6) months |

| HR (95% CI) | 0.69 (0.36-1.33) |
| P value | 0.267 |
| OS Median (95% CI): Bad | 6.2 (2.2-23.5) months |
| OS Median (95% CI): Not Bad | 12.8 (7.4-undefined) months |

| HR (95% CI) | 0.49 (0.23-1.04) |
| P value | 0.062 |
| OS Median (95% CI): Bad | 4.3 (2.1-8.3) months |
| OS Median (95% CI): Not Bad | 10.7 (5.1 undefined) months |

| HR (95% CI) | 0.39 (0.19-0.77) |
| P value | 0.007 |
| OS Median (95% CI): Bad | 9.1 (3.9-13.1) months |
| OS Median (95% CI): Not Bad | not reached (9.5-undefined) months |

APPARATUS AND METHOD FOR IDENTIFICATION OF PRIMARY IMMUNE RESISTANCE IN CANCER PATIENTS

PRIORITY

This application is a 371 International of PCT Application Number PCT/US19/21641, filed Mar. 11, 2019, which claims priority to two U.S. Provisional Applications, Ser. Nos. 62/649,762 and 62/649,771, both filed on Mar. 29, 2018, the contents of which, including the appendices thereof, are incorporated by reference herein.

BACKGROUND

This disclosure relates generally to the field of cancer treatment and more particularly to testing apparatus and method for identification, in advance, of cancer patients which are likely to be resistant to treatment with immunotherapy drugs. One specific application of this testing apparatus is predicting in advance whether a non-small-cell lung cancer patient is likely to exhibit primary immune resistance (PIR) to treatment with anti-PD-1 or anti-PD-L1 drugs, such as nivolumab.

Tumor mutations create specific neoantigens that can be recognized by the immune system. However, tumors develop a variety of mechanisms of immune evasion, including local immune suppression in the tumor microenvironment, induction of T-cell tolerance, and immunoediting. As a result, even when T-cells infiltrate the tumor they cannot kill the cancer cells. An example of this immunosuppression in cancer is mediated by a protein known as programmed cell death 1 (PD-1) which is expressed on the surface of activated T-cells. If another molecule. called programmed cell death 1 ligand 1 or programmed cell death 1 ligand 2 (PD-L1 or PD-L2), binds to PD-1, the T-cell becomes inactive. Production of PD-L1 and PD-L2 is one way that the body naturally regulates the immune system. Many cancer cells make PD-L1, hijacking this natural system and thereby allowing cancer cells to inhibit T-cells from attacking the tumor.

One approach to the treatment of cancer is to interfere with the inhibitory signals produced by cancer cells, such as PD-L1 and PD-L2, to effectively prevent the tumor cells from puffing the brakes on the immune system. Recently, an anti-PD-1 monoclonal antibody, known as nivolumab, marketed as Opdivo®, was approved by the Food and Drug Administration for treatment of patients with unresectable or metastatic melanoma who no longer respond to other drugs. In addition, nivolumab was approved for the treatment of squamous and non-squamous non-small cell lung cancer and renal cell carcinoma. Nivolumab has also been approved in melanoma in combination with ipilimumab, an anti-cytotoxic T-lymphocyte-associated protein 4 (CTLA4) antibody. Nivolumab acts as an immunomodulator by blocking ligand activation of the PD-1 receptor on activated T-cells. In contrast to traditional chemotherapies and targeted anti-cancer therapies, which exert their effects by direct cytotoxic or tumor growth inhibition, nivolumab acts by blocking a negative regulator of T-cell activation and response, thus allowing the immune system to attack the tumor. PD-1 blockers appear to free up the immune system only around the tumor, rather than more generally, which could reduce side effects from these drugs.

There is considerable cost related to these therapies, e.g. the recently approved combination of ipilimumab and nivolumab in melanoma while showing spectacular results is only effective in about 55% of patients while costing around $295,000 per treatment course. (Leonard Saltz, MD, at ASCO 2015 plenary session: "The Opdivo+Yervoy combo is priced at approximately 4000× the price of gold ($158/mg)"). This results in a co-pay of around $60,000 for patients on a standard Medicare plan. Avoiding this cost by selecting these treatments only for those patients who are likely to benefit from them would result in substantial savings to the health care system and patients.

Some patients exhibiting primary immune resistance, i.e., poor outcomes on treatment with immunotherapy, have been characterized as experiencing hyperprogression. The phenomenon of hyperprogressive disease (HPD), rapid progression and deterioration at a rate significantly exceeding that on the preceding treatment, has been anecdotally reported in cancer patients treated with anti-PD1/PD-L1 therapies for quite a while, and was systematically described in the paper of Champiat, Dercle et al., "*Hyperprogressive disease (HPD) is a new pattern of progression in cancer patients treated by anti-PD-1/PD-L1.*" Clin Cancer Res. 23 (8): 1920-1928 (2016).

Champiat et al. defined patients with HPD as those with disease progression by RECIST (Response Evaluation Criteria in Solid Tumors) at first evaluation and 2 two-fold increase in tumor growth rate upon treatment (Experimental period) vs. before treatment (Reference period). HPD was associated with worse overall survival (OS) and older age, but not with advanced disease; it was observed across various tumor types (melanoma, urothelial, colorectal, ovarian, biliary tract, lymphomas) and equally with PD-1 and PD-L1 blockers. However, one has to keep in mind that the phenomenon of disease flare on treatment is not specific to anti-PD1/PD-L1 agents and has sometimes been observed with other agents, e.g. targeted therapies. Mellema, W. W., S. A. Burgers, et al., "*Tumor flare after start of RAF inhibition in KRAS mutated NSCLC: a case report.*" Lung Cancer 87(2): 201-203 (2015).

Since publication by Champiat et al., more reports on HPD have emerged, indicating that the phenomenon may be actually more common than previously considered; for example, HPD was observed in 29% of patients with recurrent or metastatic head and neck cancer treated with anti-PD1/PD-L1 therapy. Saada-Bouzid, Defaucheux et al., "*Hyperprogression during anti-PD-1/PD-L1 therapy in patients with recurrent and/or metastatic head and neck squamous cell carcinoma.*" Ann Oncol. July 1; 28(7): 1605-1611 (2017).

The mechanism and causality of HPD is a matter of debate, and several mechanisms including genomic alterations of elements of the IFN-gamma pathway have been suggested. Given the severity of the flare in HPD, it is clinically important to be able to predict or detect it as early as possible. The HPD phenomenon is now recognized in the medical community (Sharon, "*Can an immune checkpoint inhibitor (sometimes) make things worse?*" Clinical Cancer Research. 23 (8): 1879-1881 (2017)) and needs to be addressed by finding relevant pre-treatment markers, which would allow avoiding harm to susceptible patients.

This disclosure describes a practical test and system for identifying in advance cancer patients which are likely to exhibit primary immune resistance if later treated with anti-PD-1/PD-L1 therapies. In this document, we use the term "primary immune resistance" as meaning a general resistance to immunotherapy, that is, patients who have bad outcomes and experience rapid progression on immune checkpoint inhibitors, including patients with HPD. Thus, patients with HPD, as defined quite specifically in Champiat et al. article, supra, are thus considered a subset of patients with primary immune resistance as that term is used in this document.

Our previous work in the area of predictive tests for patient benefit from immunotherapy drugs is described in U.S. Pat. No. 10,007,766, the content of which is incorporated by reference.

SUMMARY

This document will describe the classifier development sample sets we used to discover a practical test that is predictive for primary immune resistance in cancer patients, and a classifier development process or methodology we used to discover mass spectral features and parameters for classification procedures which are used to make predictions about whether a cancer patient is likely to not perform well on immunotherapies, in particular is likely to experience rapid progression on checkpoint inhibition, i.e., exhibit primary immune resistance. In one embodiment, the practical tests predict whether a non-small-cell lung cancer patient is likely to exhibit primary immune resistance if later treated with anti-PD-1/PD-L1 therapies, for example Nivolumab.

The tests of this document involve obtaining a blood-based sample of a cancer patient, subjecting the sample to mass spectrometry and producing a mass spectrum, obtaining integrated intensity values of the spectrum for a set of predefined mass spectral peaks present in the mass spectrum of the sample, and then supplying those values to a computer that is configured as a classifier which executes program instructions in the form of a test which produces a class label for the spectrum. The class label indicates whether the patient providing the sample is likely to exhibit primary immune resistance if later treated with anti-PD-1/PD-L1 therapies. The definitions of the mass spectral features which are used in the tests of this disclosure are listed in the Appendix A and Appendix B as will be explained in more detail below.

This document discloses subsidiary mass spectral classifiers, referred to as Classifier A, Classifier B, Classifier C and Classifier D, each of which produces a class label for the spectrum. We developed these four classifiers based on the same spectral acquisition and processing procedure that in various combinations address the issue of identifying patients not performing well on immunotherapies, in particular those patients that are likely to experience rapid progression on immune checkpoint inhibitors such as anti-PD-1 therapy. The program instructions for the computer implement classification instructions and parameters operating on the intensity values of the mass spectrum of the patient sample on these subsidiary classifiers and the logic for combining the outputs of these subsidiary classifiers to produce a test output or test classification label. Three of such tests are described in this document, "Test 1", "Test 2" and "Test 3."

Test 1

Test 1 is implemented in a programmed computer that executes a classification procedure coded as software instructions. See FIG. 8. Test 1 is the principal test for primary immune resistance as defined above. In one configuration, Test 1 assigns one of three classification labels, Bad, Intermediate, and Good to a patient's sample. The computer memory is configured with program code in the form of logic for comparing the class labels produced by Classifier A and Classifier D on the mass spectrum of the blood-based sample of the cancer patient, wherein if the class labels produced by both Classifier A and Classifier D are "Group1" or the equivalent indicating poor overall survival or progression free survival the patient providing the blood-based sample is assigned a "Bad" class label and the patient is predicted to exhibit primary immune resistance if treated with immunotherapy drugs.

We also evaluated the results of the binary combinations. Bad vs. Not Bad (intermediate and Good), and Good vs. Not Good (Intermediate and Bad). This test assigned 35% of the development cohort to the Bad group and 28% to the Good group. It is noteworthy that the medians in the Bad group are very short indeed, i.e. 1.4 months for PFS and 4.3 months for OS, and 85% of patients in the Bad group had a best response of PD. In comparison to the chemotherapy arm of PROSE (described below), the Bad group does appear to do worse on immune therapy than on chemotherapy, indicating that we have indeed identified a group of patients where checkpoint inhibition may not provide the advantage seen in the other groups. Although these data are not from a randomized study, we believe that the test is likely to be predictive for anti-PD1 vs chemotherapy. The Good group defined by Test 1 had excellent outcomes, with median OS in excess of 17 months and median PFS of 9.1 months. The proportion of patients experiencing PD as best response in this group was only 28% and the response rate (CR+PR) was 28%. No significant association of Test 1 with baseline clinical characteristics was found for the ternary classification, although Bad vs Not Bad classification was associated with performance status. However, multivariate analysis indicated that test classification (Bad vs Not Bad or Good vs Not Good) remained an independent predictor of OS and PFS when adjusted for other prognostic factors including smoking status, histology, and performance status.

In one specific embodiment, there is described a testing apparatus for predicting primary immune resistance to immunotherapy drugs for a cancer patient, comprising, in combination:
  a mass spectrometer configured to conduct mass spectrometry on a blood-based sample obtained from the cancer patient and obtaining a mass spectrum in the form of a set of integrated intensity values for a multitude of features in the mass spectrum;
  a processing unit, and
  a nontransitory computer memory storing instructions and classification parameters for at least a first classifier and a second classifier (Classifiers A and D, respectively), for execution by the processing unit,
  wherein Classifier A is defined by:
  a) a reference set of integrated intensity mass spectral feature values for a set of mass spectral features associated with immune response type 2, the feature values obtained by conducting mass spectrometry on a development set of blood-based samples obtained from a population of non-small cell lung cancer patients treated with an anti-PD-1 drug; and
  b) parameters defining a classification procedure for generating a class label for the mass spectrum of the blood-based sample of the cancer patient by comparing the integrated intensity values of features associated with immune response type 2 In the mass spectrum of the blood-based sample of the cancer patient with the reference set of Classifier A:
  wherein Classifier D is defined by:
  a) a reference set of integrated intensity mass spectral feature values for a set of mass spectral features, the feature values obtained by conducting mass spectrometry on a development set of blood-based samples obtained from a population of melanoma patients treated with an anti-PD-1 drug; and b) parameters defining a classification procedure for generating a class label for the mass spectrum of the blood-based sample of the cancer patient by comparing the integrated intensity values of features in the mass spectrum of the blood-based sample of the cancer patient with the reference set of Classifier D.

On the other hand, one can perform Test 1 as explained above and if the class label for the patient is tested as Good or the equivalent the patient is predicted to have a very good outcome on immune monotherapy.

Test 2

Test 2 is implemented in a programmed computer that executes a classification procedure coded as software instructions. See FIG. 12. The final class label "Bad" of Test 2 indicates poor prognosis, whether the patient gets immunotherapy or an alternative chemotherapy such as docetaxel or pemetrexed. Bad is the class label assigned if Classifier C assigns a "Group1" label or the equivalent indicating poor prognosis. Classifiers B and D are only used to generate Indeterminate or Good class labels. The Test 1 bad group appears to identify patients with a poor prognosis on immunotherapy, regardless of whether they would have better or similar outcomes on alternative therapies. Test 2 identifies the subgroup of patients with poor prognosis on both immunotherapy and alternative chemotherapy, i.e. the Group1 label from Classifier C. Test 2 can also be used to identify patients who are predicted to have a very good outcome on monotherapy with the Good class label or the equivalent, using classifiers B and D.

Based on comparison with data from a chemotherapy-treated cohort, such patients seem to have similarly poor outcomes on alternative therapy. Test 2 assigned 21% of the development cohort to the Bad group. Like Test 1, in one configuration Test 2 assigns samples one of three classifications Bad, Intermediate and Good, and for the development cohort the Test 2 Good group is identical to the Test 1 Good group. The Bad group demonstrated very poor outcomes with median OS and PFS of 3.1 months and 1.4 months, respectively, with 79% of patients with a best response of PD. Ternary and binary test classification was associated with performance status, but classification Good vs Not Good was an independent predictor of OS and PFS in multivariate analysis. The association of test classification with performance status together with the lack of independent prognostic power of test classification Bad vs Not Bad for OS and PFS in multivariate analysis points towards the generally poor prognosis of patients classified as Bad by this test.

In another aspect, testing apparatus is described for predicting poor prognosis in response to treatment by either an immunotherapy drug or an alternative chemotherapy for a cancer patient. The testing apparatus includes:

a mass spectrometer configured to conduct mass spectrometry on a blood-based sample obtained from the cancer patient and obtaining a mass spectrum in the form of a set of integrated intensity values for a multitude of features in the mass spectrum;

a processing unit, and a nontransitory computer memory storing instructions and classification parameters for at least a first classifier (Classifier C), for execution by the processing unit, wherein Classifier C is defined by:

a) a reference set of integrated intensity mass spectral feature values for a set of mass spectral features, the feature values obtained by conducting mass spectrometry on a development set of blood-based samples obtained from a population of non-small-cell lung cancer patients treated with an anti-PD1 drug; and b) parameters defining a classification procedure for generating a class label for the mass spectrum of the blood-based sample of the cancer patient by comparing the integrated intensity values of features in the mass spectrum of the blood-based sample of the cancer patient with the reference set of Classifier C.

If the class label generated by Classifier C is "Group1" or the equivalent indicating poor overall survival or progression free survival the patient is predicted to have a poor prognosis in response to treatment by either the immunotherapy drug or the alternative chemotherapy.

Test 3

A third test, Test 3 herein, is based on a logical combination of the outputs of Tests 1 and 2. See FIG. 16. Test 3 assigns samples which are classified as Bad by Test 1 and Not Bad by Test 2 (e.g., either Intermediate or Good in a ternary classification regime for Test 2) as "Resistant", with the hypothesis that, while patients classified as Bad by Test 2 may have very poor outcomes under all therapies, the poor prognosis of "Resistant" patients labelled in accordance with Test 3 may be induced by checkpoint inhibition, and these patients may have better outcomes with alternative therapies, such as docetaxel, or newer chemotherapy regimens, such as docetaxel plus ramucirumab, than on an anti-PD-1 agent.

Preliminary data on reproducibility from an independent set of 98 samples taken from patients with NSCLC indicated ternary classification concordance between 85% and 89% for the tests. Reproducibility for any binary version of Test 1 and Test 2 was 91% or higher.

Protein set enrichment analysis indicates the association of all three tests with complement activation and acute phase reactants. In addition, Tests 1 and 3 were associated with wound healing and extracellular matrix and Tests 1 and 2 were associated with innate immune response.

In summary, the presented tests provide a potential tool to inform on the likelihood of immune therapy benefit, with special emphasis on primary resistance. In its Bad group Test 1, the PIR test, identifies a group of patients that, compared to chemotherapy, obtains little benefit. Test 2 identifies a group of patients that appears to have poor outcomes regardless of therapy. Test 3 identifies a group of patients where checkpoint inhibition might potentially be detrimental, guiding patients towards treatment with alternative chemotherapies. The Good group of Test 1 and Test 2 demonstrates excellent outcomes, indicating that these patients are likely to do well on checkpoint inhibition, for example anti-PD-1 monotherapy.

BRIEF DESCRIPTION OF THE DRAWINGS

FIG. 1A shows overall survival (OS), FIG. 1B shows progression free survival (PFS).

FIG. 2A shows overall survival (OS), FIG. 2B shows time to progression (TTP).

FIG. 3A shows overall survival (OS), FIG. 3B shows progression free survival (PFS).

FIGS. 5A and 5B is a diagram of a classifier development procedure we refer to as "Diagnostic Cortex" which was used to develop Classifiers A, B, C and D in this disclosure.

FIG. 7 is a Receiver Operating Characteristic (ROC) curve for Classifier C, considering the 116 samples used in development.

FIG. 9A-9F: Kaplan-Meier plots of OS and PFS split by Test 1 classifications (and their binary combinations) of Set A.

DETAILED DESCRIPTION

Figure 1A:
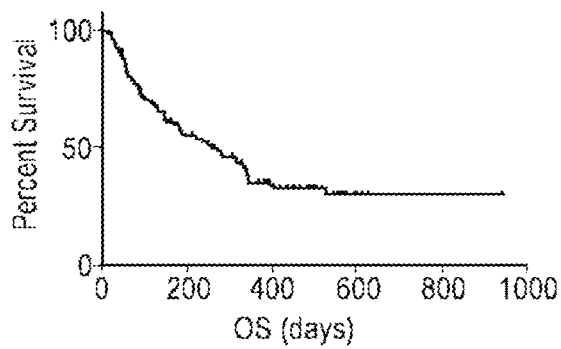
FIGS. 1A and 1B: Time-to-event data for all 116 patients from Set A with available clinical data and spectra from pretreatment samples.

This document will describe the sample sets and a classifier development process we used to discover mass spectral features and parameters for a classification procedure which is used to make predictions about whether a patient is likely to exhibit primary immune resistance if later treated with anti-PD-1/PD-L1 therapies. This document will also present results from the application of the classifier to the classifier development set and validation set and describe the biological associations with classifier labels.

This document discloses subsidiary mass spectral classifiers, referred to as Classifier A, Classifier B, Classifier C and Classifier D, each of which produces a class label for the mass spectrum of a blood-based sample. VW developed these four classifiers based on the same spectral acquisition and processing procedure that in various combinations address the issue of identifying patients not performing well on immunotherapies, in particular those patients that are likely to experience rapid progression on immune checkpoint inhibitors such as anti-PD-1 therapy. The program instructions for the computer implement classification instructions and parameters operating on the intensity values of the mass spectrum of the patient sample for each of these subsidiary classifiers and the logic for combining the outputs of these subsidiary classifiers to produce a test output or test classification label. Three of such tests are described in this document, "Test 1", "Test 2" and "Test 3."

Test 1

Test 1 is implemented in a programmed computer that executes a classification procedure coded as software instructions. See FIG. 8. Test 1 is the principal test for primary immune resistance as defined in the Background section previously. In one configuration, Test 1 assigns one of three classification labels, Bad, Intermediate, and Good to a patient's sample. The computer memory is configured with program code in the form of logic for comparing the class labels produced by Classifier A and Classifier D on the mass spectrum of the blood-based sample of the cancer patient, wherein if the class labels produced by both Classifier A and Classifier D are "Group1" or the equivalent indicating poor overall survival or progression free survival the patient providing the blood-based sample is assigned a "Bad" class label and the patient is predicted to exhibit primary immune resistance if treated with immunotherapy drugs. On the other hand, patients classified as Good under Test 1 are predicted to have very good outcomes on immune monotherapy.

Test 2

Test 2 is implemented in a programmed computer that executes a classification procedure coded as software instructions. See FIG. 12. The final class label "Bad" of Test 2 indicates poor prognosis, whether the patient gets immunotherapy or an alternative chemotherapy such as docetaxel or pemetrexed. Bad is the class label assigned if Classifier C assigns a "Group1" label or the equivalent indicating poor prognosis. Classifiers B and D are only used to generate Indeterminate or Good class labels. The Test 1 bad group appears to identify patients with a poor prognosis on immunotherapy, regardless of whether they would have better or similar outcomes on alternative therapies. Test 2 identifies the subgroup of patients with poor prognosis on both immunotherapy and alternative chemotherapy, i.e. the Group1 label from Classifier C. In one possible embodiment, Classifiers B and D may also be used and if the class label is Good or the equivalent the patient is predicted to have a very good outcome on immune monotherapy.

Test 3

Figure 16:
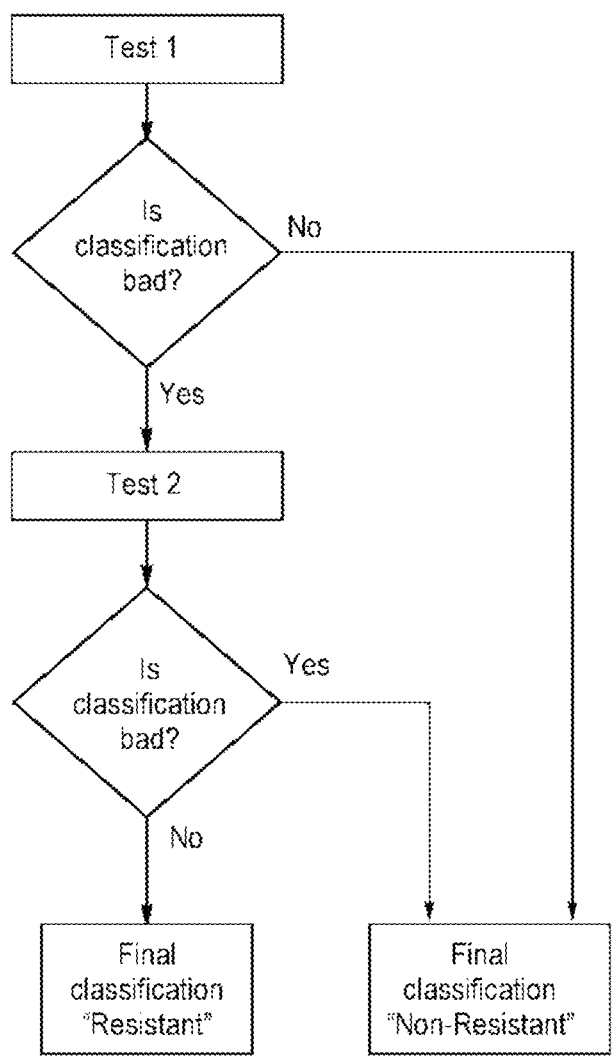
FIG. 16 is a diagram showing the logic for combining Tests 1 and 2 as a schema for Test 3.

A third test, Test 3 herein, is based on a logical combination of the outputs of Tests 1 and 2. See FIG. 16. Test 3 assigns samples which are classified as Bad by Test 1 and Not Bad by Test 2 (e.g., either Intermediate or Good in a ternary classification regime for Test 2) as "Resistant", with the hypothesis that, while patients classified as Bad by Test 2 may have very poor outcomes under all therapies, the poor prognosis of "Resistant" patients labelled in accordance with Test 3 may be induced by checkpoint inhibition, and these patients may have better outcomes with alternative therapies, such as docetaxel, or newer chemotherapy regimens, such as docetaxel plus ramucirumab, than on an anti-PD-1 agent.

The tests of this document involve obtaining a blood-based sample of a cancer patient, subjecting the sample to mass spectrometry and producing a mass spectrum, obtaining integrated intensity values of the spectrum for a set of predefined mass spectral regions present in the mass spectrum of the sample, and then supplying those values to a computer that is configured as a classifier which executes program instructions in the form of a test which produces a class label for the spectrum. The class label indicates whether the patient providing the sample is likely to exhibit primary immune resistance, or depending on the configuration of the test, whether the patient is likely to exhibit very good outcomes on immune monotherapy.

Figure 1B:
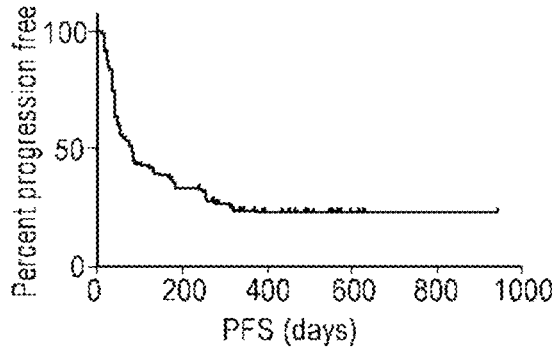

Classifier Development Samples:

The classifiers and tests presented in this document made use of three datasets:

"Set A": pre-treatment samples collected from Non-Small Cell Lung Cancer (NSCLC) patients receiving nivolumab in second line. A total of 118 samples had available clinical data (including progression free survival (PFS), overall survival (OS), and response) and mass spectra passing QC metrics. The baseline clinical characteristics are listed in table 1 and survival plots (PFS and OS) are shown in FIGS. 1A and 1B. This set was used in the development of three of the Classifiers described in this document, Classifiers A, B and C.

Figure 2A:
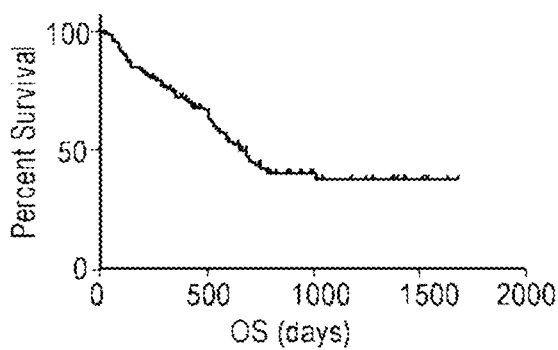
FIGS. 2A and 2B: Time-to-event data for all 113 patients from Set B with available clinical data and spectra from pretreatment samples.
Figure 2B:
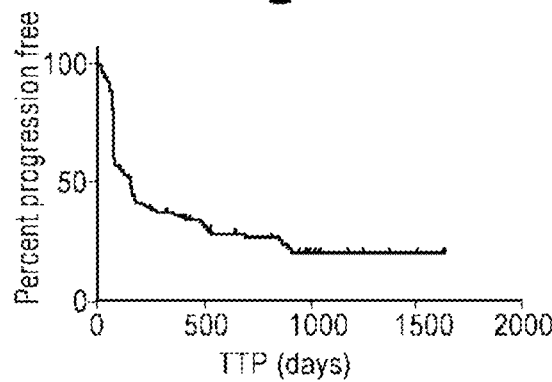

"Set B": pre-treatment samples collected from Melanoma patients receiving nivolumab. A total of 113 samples had available clinical data (including time-to-progression (TTP), OS, and response) and mass spectra passing QC metrics. The baseline clinical characteristics are listed in table 2 and survival plots (TTP and OS) are shown in FIGS. 2A and 2B. This set was used in the development of one of the Classifiers described in this document, Classifier D.

Figure 3A:
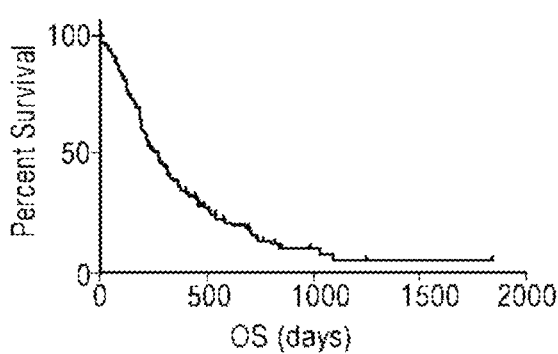
FIGS. 3a and 3B: Time-to-event data for all 123 patients from Set C with available clinical data and spectra from pretreatment samples.
Figure 3B:
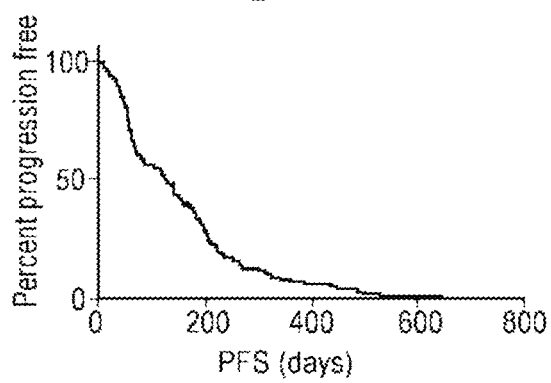

"Set C": pre-treatment samples collected from second line NSCLC patients enrolled in the PROSE trial. See Gregorc, et al., *Predictive value of a proteomic signature in patients with non-small-cell lung cancer treated with second-line erlotinib or chemotherapy (PROSE): a biomarker-stratifed, randomised phase 3 trial*, Lancet Oncology, vol. 15 no. 7 pp. 713-721 (June 2014). As part of the trial, patients were randomized between two treatment arms: erlotinib and chemotherapy (docetaxel or pemetrexed). Set C comprises samples from 123 patients assigned to the chemotherapy arm, that had available clinical data (PFS and OS) and mass spectra passing QC metrics. Sixty-eight of those samples received treatment with docetaxel and 54 received treatment with pemetrexed. The baseline clinical characteristics are listed in table 3 and survival plots (OS and PFS) are shown in FIGS. 3A and 3B. This set was run through the classifiers and tests described in this document after their parameters were locked, and thus were not used, strictly speaking, in the development of Classifiers A-D.

TABLE 1

Baseline characteristics and response to therapy of patients from Set A (NSCLC) with available spectra

|  |  | N (%) |
|---|---|---|
| Gender | Male | 66 (57) |
|  | Female | 50 (43) |
| Age | Median (Range) | 65 (43-83) |
| Response | CR | 1 (1) |
|  | PR | 16 (14) |
|  | SD | 19 (16) |
|  | PD | 65 (56) |
|  | NA | 15 (13) |
| Histology | Two primary tumors | 2 (2) |
|  | Adenocarcinoma | 77 (66) |
|  | NSCLC-NEC | 3 (3) |
|  | NSCLC-NOS | 8 (7) |
|  | Squamous | 26 (22) |
| PFS | Median (days) | 79 |
| OS | Median (days) | 260 |
| Performance Status | 0 | 36 (31) |
|  | 1 | 60 (52) |
|  | 2 | 12 (10) |
|  | 3 | 3 (3) |
|  | NA | 5 (4) |
| PD-L1 status |  | N (%) |
| Positive (≥1%) |  | 32 (28) |
| Negative (<1%) |  | 38 (33) |
| NA |  | 46 (40) |
| Smoking Status | Current | 23 (20) |
|  | Former | 81 (70) |
|  | Never | 10 (9) |
|  | NA | 2 (2) |
| Brain Metastases at start of Itx | No | 87 (75) |
|  | Yes | 29 (25) |
| Previous Rtx | No | 43 (37) |
|  | Yes | 73 (63) |
| Previous Thoracic Rtx | No | 79 (68) |
|  | Yes | 37 (32) |
| VeriStrat classification[1] | Good | 88 (76) |
|  | Poor | 28 (24) |

[1]VeriStrat Classifier (see U.S. Pat. No. 7,736,905) applied to Deep MALDI average spectra

TABLE 2

Baseline characteristics and response to therapy of patients from Set B (Melanoma) with available spectra

|  |  | N (%) |
|---|---|---|
| Gender | Male | 69 (61) |
|  | Female | 43 (38) |
|  | NA | 1 (1) |
| Age | Median (Range) | 61 (16-87) |
| Response | PR | 30 (27) |
|  | SD | 18 (16) |
|  | PD | 65 (58) |
| TTP | Median (days) | 162 |
| OS | Median (days) | 658 |
| Prior Ipi | No | 30 (27) |
|  | Yes | 83 (73) |
| PD-L1 expression (5% tumor) | Positive | 8 (7) |
|  | Negative | 28 (25) |
|  | NA | 77 (68) |
| PD-L1 expression (1% tumor) | Positive | 17 (15) |
|  | Negative | 19 (17) |
|  | NA | 77 (68) |

TABLE 2-continued

Baseline characteristics and response
to therapy of patients from Set B
(Melanoma) with available spectra

|  |  | N (%) |
|---|---|---|
| PD-L1 expression (1% tumor + immune cells) | Positive | 27 (23) |
| | Negative | 7 (6) |
| | NA | 79 (70) |
| VenStrat-like classification * | Good | 94 (83) |
| | Poor | 19 (17) |

* A "VeriStrat-like" classification was obtained by averaging 3 deep MALDI 800-shot raster spectra in triplicate and applying the standard VeriStrat classification algorithm (see U.S. Pat. No. 7,736,905) to the three averaged spectra. It has been observed that the amplitude of some peaks contained within the VeriStrat feature definition windows can decrease as a function of increasing spot number for deep MALDI spotting procedures. Hence rasters were only selected from the first spot for each sample. A pool of 18 rasters was selected from the raster passing filtering for number of peaks and alignment for the first spot for each sample. Nine of the 18 rasters were chosen at random and divided into three sets of three. Each set of three rasters was averaged together to produce three averaged spectra, each one approximating a spectrum obtained from a standard VeriStrat spectral acquisition. The standard VeriStrat classification algorithm was applied to the triplicate spectra to yield a label of good, poor, or indeterminate.

TABLE 3

Baseline characteristics of patients
from Set C (NSCLC) with available
spectra

|  |  | N (%) |
|---|---|---|
| Gender | Male | 87 (71) |
| | Female | 36 (29) |
| Age | Median (Range) | 64 (39-77) |
| Response | PR | 13 (11) |
| | SD | 49 (40) |
| | PD | 42 (34) |
| | NA | 19 (15) |
| PFS | Median (days) | 127 |
| OS | Median (days) | 272 |
| Performance Status | 0 | 61 (50) |
| | 1 | 54 (44) |
| | 2 | 8 (7) |
| Histology | Adenocarcinoma | 88 (72) |
| | BAC | 2 (2) |
| | Large | 6 (5) |
| | Squamous | 14 (11) |
| | NA | 13 (11) |
| Stage | IIIB | 17 (14) |
| | IV | 104 (85) |
| | NA | 2 (2) |
| Smoking Status | Current | 37 (30) |
| | Former | 70 (57) |
| | Never | 16 (13) |
| Previous Rtx | No | 79 (64) |
| | Yes | 42 (34) |
| | NA | 2 (2) |
| Previous Surgery | No | 90 (73) |
| | Yes | 31 (25) |
| | NA | 2 (2) |
| VeriStrat classification | Good | 84 (68) |
| | Poor | 39 (32) |
| Chemotherapy type | Docetaxel | 68 (55) |
| | Pemetrexed | 54 (44) |

Sample Preparation

The sample preparation procedures we used are similar to those described in previous patent applications and issued patents of the Assignee, see e.g., U.S. patent application publication 2017/0039345, ¶¶ 182-186.

Spectral Acquisition Processing

Matrix assisted laser desorption and ionization (MALDI) time of flight (TOF) mass spectra were obtained from the samples. Generally speaking, the spectra were processed and raster spectra averaged in accordance with the procedures described in U.S. patent application publication 2017/0039345, ¶¶ 188-222 and described below. The result of the spectral acquisition and processing steps described below is a set of integrated intensity values of the spectra for all samples in the classifier development set (Sets A, B) for the set of features listed in Appendix A. The mass spectral data acquisition and processing described below makes use of the method we refer to as DEEP MALDI, described in U.S. Pat. No. 9,279,798 assigned to Biodesix, Inc., the content of which is incorporated by reference herein. (Note: development set C was used to asses performance post-hoc and was not as a reference set in classifier test development).

Background estimation and subtraction were performed on the spectra. The Convex Hull method of background estimation and subtraction was used to conservatively remove the bulk of background that is variable between samples within a batch of spectra. This background is largest in the low m/z range and decays with increasing m/z. The convex hull does not allow the background estimation to fit to peak humps (regions of overlapping peaks). There are no parameters for estimation, but the method works properly only when the estimate is performed on smoothed data to prevent spurious noise spikes from dominating the fit.

The spectra were rescaled following background subtraction by combining several wide windows of spectra to compute a normalization scalar and applying it to the spectra.

An external evaluation revealed that removing the peak humps, retaining only the independent peak portion, improved reproducibility across instrument states (i.e., reduced batch effects). Feature value distributions comparing methods of preprocessing revealed that this step may protect against changes in instrument state that lead to batch shifts in feature values. To do this, an aggressive background estimation method was used that fits to the base signal. Residual background and peak humps are reduced to leave a flat background. A caveat is that the signal is reduced from prominent peaks as a result of the aggressive estimation. While this is an undesired effect of the method, as it effectively reduces signal to noise ratios, the gains in reproducibility are important for ensuring tests run similarly over many instrument states.

The spectra were again rescaled following background subtraction using normalization. The peaks included in normalization were determined using an analysis of several projects collected at several instrument states and cancer indications. This approach examined peaks to find regions of intrinsic stability. The combination of these regions was used to compute a normalization scalar for each spectrum.

The peak alignment of the average spectra is typically very good; however, a fine-tune alignment step was performed to address minor differences in peak positions in the spectra. A set of alignment points was identified and applied to the analysis spectra using a calibration tolerance of 800 ppm.

Feature Definitions

Figure 4:
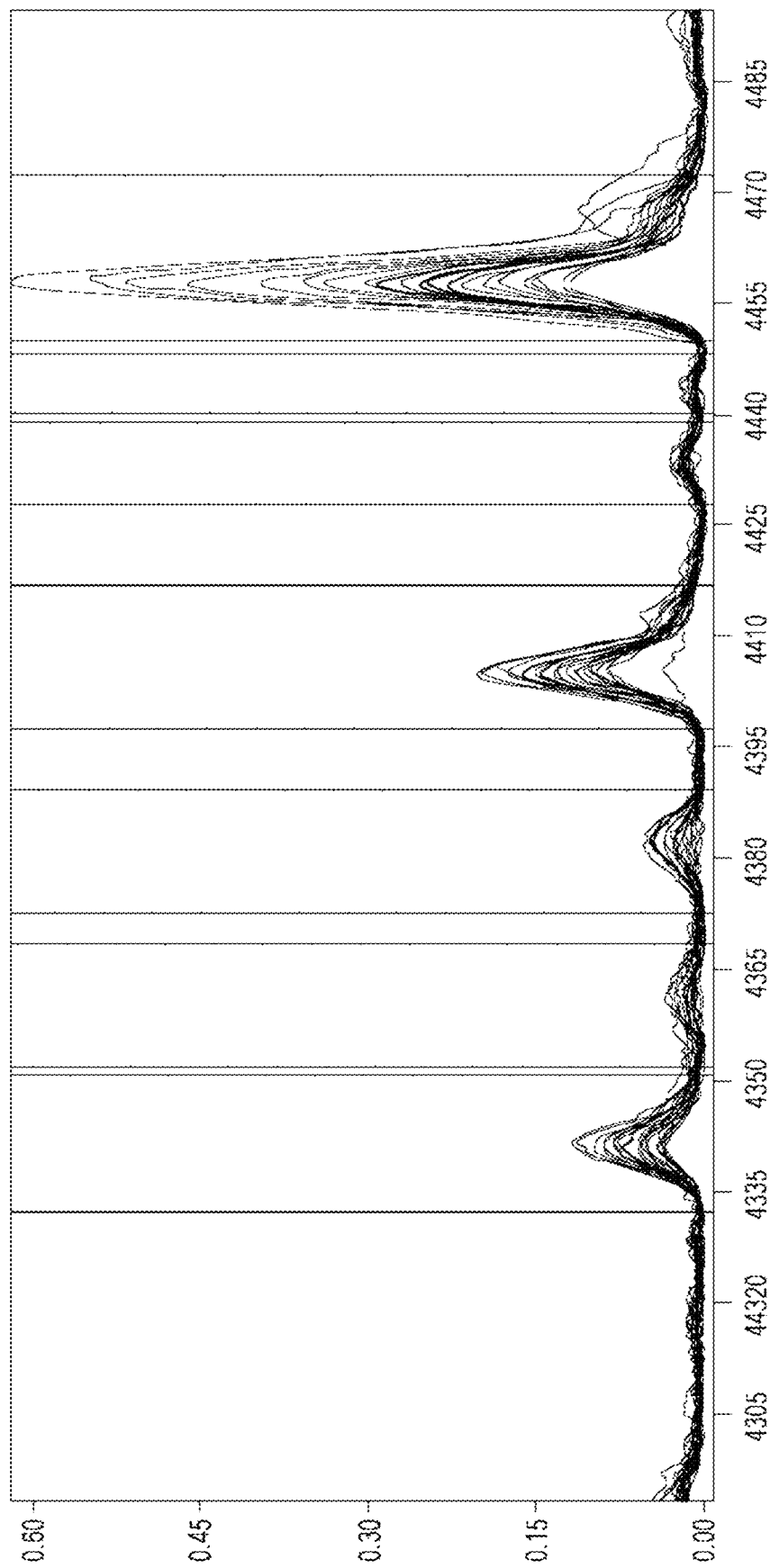
FIG. 4: Example of features defined in the mass spectral dataset.

Feature definitions were selected in several steps using a subset of spectra (from Set A) at each iteration as described. Several spectra were first loaded simultaneously and features defined. After the first round, a second set of spectra were examined. Some features were not optimally defined from the first round and were adjusted to meet requirements of the second set of spectra. New features were identified that were not present in the first set of spectra. This process was continued until the final set was determined. As a final step, each batch was examined to determine if any additional features could be defined that could only be identified with knowledge from many spectra loaded simultaneously. Several features were identified that may have heightened susceptibility to peptide modifications that take place during the sample preparation procedure. These manifest in spectra in specific m/z regions where the peaks change in intensity and shape and may depend on the position on the plate where the sample was spotted. These regions were excluded from the final feature tables. A final set of 282 feature definitions was applied to the spectra and is listed in Appendix A. An example of features defined using the described method is illustrated in FIG. 4.

Batch Correction of Analysis Spectra and Partial Ion Current (PIC) Normalization A batch correction of analysis spectra was performed as described in U.S. patent application publication 2017/0039345. A partial ion current normalization (PIC) process was also carried out as described in U.S. patent application publication 2017/0039345. Features used for PIC normalization are listed in Table 4:

TABLE 4

| m/z |
| --- |
| 4360 |
| 4381 |
| 4566 |
| 5404 |
| 8366 |
| 8411 |
| 8961 |
| 8978 |
| 8999 |
| 9037 |
| 9097 |
| 9208 |
| 9263 |
| 9648 |
| 10140 |
| 10185 |
| 10211 |
| 14431 |

The normalization scalar is computed by summing the feature values for each of the listed features for each sample. The resulting scalars were compared for association with clinical groups defined by the median OS (Early vs Late) for Set A. We generated plots of the normalization scalars for Early and Late groups, similar to FIG. 7 of U.S. patent application publication 2017/0039345, which demonstrated that the normalization scalars were not found to be associated with the OS groups.

The final feature table, in the form of integrated intensity values of the mass spectra as processed above from all samples to be used in new Classifier development (NCD), is stored in computer memory and used for Classifier development in accordance with FIGS. 5A-5B described below. These feature values are referred to as a "reference set" herein.

Trim Feature Table

Eight features were included in the preprocessing that are ill-suited for inclusion in classifier development as they are related to hemolysis. It has been observed that these large peaks are useful for stable batch corrections because once in the serum, they appear stable over time and resistant to modifications. However, these peaks are related to the amount of red blood cell shearing during the blood collection procedure and should not be used for test development beyond feature table corrections in preprocessing. The features marked with an asterisk in Appendix A were removed from the final feature table, yielding a total of 274 mass spectral features used for new classifier development.

Figure 5B:
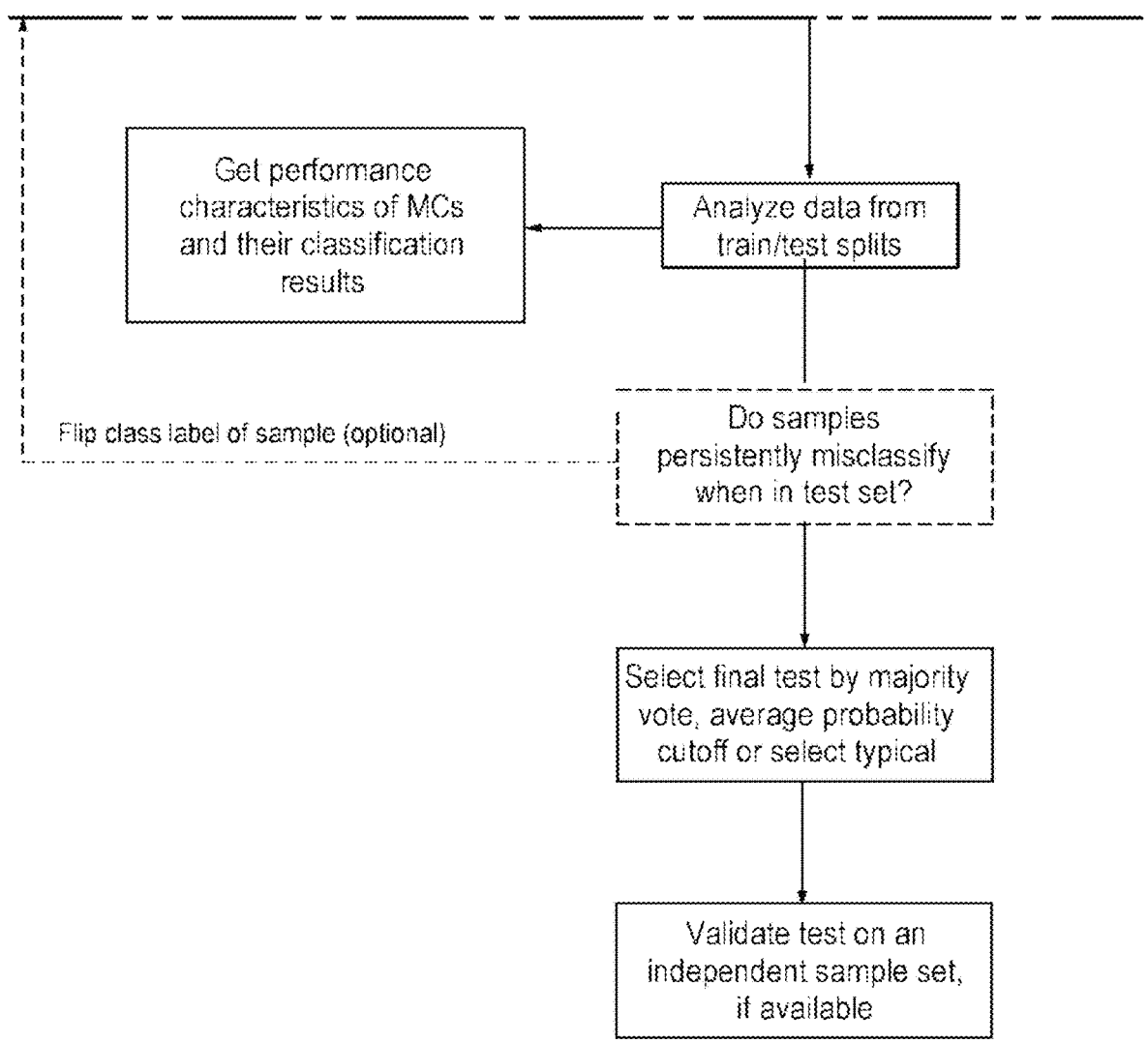

Classifier Development (FIGS. 5A-5B)

The new classifier development process was carried out using the Diagnostic Cortex® procedure shown in FIGS. 5A-5B. This procedure is described at length in the patent literature, see U.S. Pat. No. 9,477,906. See also pages 44-54 and FIGS. 8A-8B of U.S. patent application publication 2017/0039345. An overview of the process will be described and then the specifics for the present classifier generation exercise will be described later on.

This document presents the results for Test 1, Test 2 and Test 3. In one possible configuration, these tests combine the classifications obtained by one or more of the following Classifiers: Classifier A, Classifier B, Classifier C and Classifier D in a hierarchical schema shown in the figures and explained below. Classifiers A-C were developed using Set A (described above) and Classifier D was developed using Set B (described above). Further details about the mentioned classifiers and the combination rules or logic implemented in each of the reported tests will be given in the following sections.

In contrast to standard applications of machine learning focusing on developing classifiers when large training data sets are available, the big data challenge, in bio-life-sciences the problem setting is different. Here we have the problem that the number (n) of available samples, arising typically from clinical studies, is often limited, and the number of attributes (measurements) (p) per sample usually exceeds the number of samples. Rather than obtaining information from many instances, in these deep data problems one attempts to gain information from a deep description of individual instances. The present methods take advantage of this insight, and are particularly useful, as here, in problems where $p \gg n$.

The method includes a first step a) of obtaining measurement data for classification from a multitude of samples. i.e., measurement data reflecting some physical property or characteristic of the samples. The data for each of the samples consists of a multitude of feature values, and a class label. In this example, the data takes the form of mass spectrometry data, in the form of feature values (integrated peak intensity values at a multitude of m/z ranges or peaks, see Appendix A) as well as a label associated with some attribute of the sample (for example, patient Early or Late death or disease progression, "Group1", "Group2" etc. the precise moniker of the label is not important). In this example, the class labels were assigned by a human operator to each of the samples after investigation of the clinical data associated with the sample. The development sample set is then split into a training set and a test set and the training set is used in the following steps b), c) and d).

The method continues with a step b) of constructing a multitude of individual mini-Classifiers using sets of feature values from the samples up to a pre-selected feature set size s (s=integer 1 . . . p). For example a multiple of individual mini- or atomic classifiers could be constructed using a single feature (s=1), or pairs of features (s=2), or three of the features (s=3), or even higher order combinations containing more than 3 features. The selection of a value of s will normally be small enough to allow the code implementing the method to run in a reasonable amount of time, but could be larger in some circumstances or where longer code run-times are acceptable. The selection of a value of s also may be dictated by the number of measured variables (p) in the data set, and where p is in the hundreds, thousands or even tens of thousands, s will typically be 1, or 2 or possibly 3, depending on the computing resources available. The mini-Classifiers execute a supervised learning classification algorithm, such as k-nearest neighbors (kNN), in which the values for a feature, pairs or triplets of features of a sample instance are compared to the values of the same feature or features in a training set and the nearest neighbors (e.g., k=9) in an s-dimensional feature space are identified and by majority vote a class label is assigned to the sample instance for each mini-Classifier. In practice, there may be thousands of such mini-Classifiers depending on the number of features which are used for classification.

The method continues with a filtering step c), namely testing the performance, for example the accuracy, of each of the individual mini-Classifiers to correctly classify the sample, or measuring the individual mini-Classifier performance by some other metric (e.g. the Hazard Ratios (HRs) obtained between groups defined by the classifications of the individual mini-Classifier for the training set samples) and retaining only those mini-Classifiers whose classification accuracy, predictive power, or other performance metric, exceeds a pre-defined threshold to arrive at a filtered (pruned) set of mini-Classifiers. The class label resulting from the classification operation may be compared with the class label for the sample known in advance if the chosen performance metric for mini-Classifier filtering is classification accuracy. However, other performance metrics may be used and evaluated using the class labels resulting from the classification operation. Only those mini-Classifiers that perform reasonably well under the chosen performance metric for classification are maintained. Alternative supervised classification algorithms could be used, such as linear discriminants, decision trees, probabilistic classification methods, margin-based Classifiers like support vector machines, and any other classification method that trains a Classifier from a set of labeled training data.

To overcome the problem of being biased by some univariate feature selection method depending on subset bias, we take a large proportion of all possible features as candidates for mini-Classifiers. We then construct all possible kNN classifiers using feature sets up to a pre-selected size (parameters). This gives us many "mini-Classifiers": e.g. if we start with 100 features for each sample (p=100), we would get 4950 "mini-Classifiers" from all different possible combinations of pairs of these features (s=2), 161,700 mini-Classifiers using all possible combination of three features (s=3), and so forth. Other methods of exploring the space of possible mini-Classifiers and features defining them are of course possible and could be used in place of this hierarchical approach. Of course, many of these "mini-Classifiers" will have poor performance, and hence in the filtering step c) we only use those "mini-Classifiers" that pass predefined criteria. These filtering criteria are chosen dependent on the particular problem: If one has a two-class classification problem, one would select only those mini-Classifiers whose classification accuracy exceeds a pre-defined threshold, i.e., are predictive to some reasonable degree. Even with this filtering of "mini-Classifiers" we end up with many thousands of "mini-Classifier" candidates with performance spanning the whole range from borderline to decent to excellent performance.

The method continues with step d) of generating a Master Classifier (MC) by combining the filtered mini-Classifiers using a regularized combination method. In one embodiment, this regularized combination method takes the form of repeatedly conducting a logistic training of the filtered set of mini-Classifiers to the class labels for the samples. This is done by randomly selecting a small fraction of the filtered mini-Classifiers as a result of carrying out an extreme dropout from the filtered set of mini-Classifiers (a technique referred to as drop-out regularization herein), and conducting logistical training on such selected mini-Classifiers. While similar in spirit to standard classifier combination methods (see e.g. S. Tulyakov et al., *Review of Classifier Combination Methods, Studies in Computational Intelligence*, Volume 90, 2008, pp. 361-386), we have the particular problem that some "mini-Classifiers" could be artificially perfect just by random chance, and hence would dominate the combinations. To avoid this overfitting to particular dominating "mini-Classifiers", we generate many logistic training steps by randomly selecting only a small fraction of the "mini-Classifiers" for each of these logistic training steps. This is a regularization of the problem in the spirit of dropout as used in deep learning theory. In this case, where we have many mini-Classifiers and a small training set we use extreme dropout, where in excess of 99% of filtered mini-Classifiers are dropped out in each iteration.

In more detail, the result of each mini-Classifier is one of two values, either "Group1" or "Group2" in this example. We can then combine the results of the mini-Classifiers by defining the probability of obtaining an "Early" label via standard logistic regression (see e.g. http://en.wikipedia.org/wiki/Logistic_regression)

$$P(\text{"Early"}|\text{feature values for a spectrum}) = \frac{1 - \exp(\sum w_{mc} I(mc(\text{feature values})))}{\text{Normalization}} \text{ mini Classifiers} \quad \text{Eq. (1)}$$

where $I(mc(\text{feature values}))=1$, If the mini-Classifier mc applied to the feature values of a sample returns "Group2", and 0 if the mini-Classifier returns "Group1". The weights $w_{mc}$ for the mini-Classifiers are unknown and need to be determined from a regression fit of the above formula for all samples in the training set using +1 for the left hand side of the formula for the Group2-labeled samples in the training set, and 0 for the Group1-labeled samples, respectively. As we have many more mini-Classifiers, and therefore weights, than samples, typically thousands of mini-Classifiers and only tens of samples, such a fit will always lead to nearly perfect classification, and can easily be dominated by a mini-Classifier that, possibly by random chance, fits the particular problem very well. We do not want our final test to be dominated by a single special mini-Classifier which only performs well on this particular set and is unable to generalize well. Hence we designed a method to regularize such behavior-Instead of one overall regression to fit all the weights for all mini-Classifiers to the training data at the same time, we use only a few of the mini-Classifiers for a regression, but repeat this process many times in generating the master classifier. For example we randomly pick three of the mini-Classifiers, perform a regression for their three weights, pick another set of three mini-Classifiers, and determine their weights, and repeat this process many times, generating many random picks, i.e. realizations of three mini-Classifiers. The final weights defining the master Classifier are then the averages of the weights over all such realizations. The number of realizations should be large enough that each mini-Classifier is very likely to be picked at least once during the entire process. This approach is similar in spirit to "drop-out" regularization, a method used in the deep learning community to add noise to neural network training to avoid being trapped in local minima of the objective function.

Other methods for performing the regularized combination method in step (d) that could be used include:

Logistic regression with a penalty function like ridge regression (based on Tikhonov regularization, Tikhonov, Andrey Nikolayevich (1943). "Об устойчивости обратных задач" [On the stability of inverse problems]. Doklady Akademii Nauk SSSR 39 (5): 195-198.)

The Lasso method (ibshirani, R. (1996). Regression shrinkage and selection via the lasso. J. Royal. Statist. Soc B., Vol. 58, No. 1, pages 267-288).

Neural networks regularized by drop-out (Nitish Shrivastava, "*Improving Neural Networks with Dropout*", Master's Thesis, Graduate Department of Computer Science, University of Toronto), available from the website of the University of Toronto Computer Science department.

General regularized neural networks. (Girosi F. et al. Neural Computation, (7), 219 (1995)).

The above-cited publications are incorporated by reference herein. Our approach of using drop-out regularization has shown promise in avoiding over-fitting, and increasing the likelihood of generating generalizable tests, i.e. tests that can be validated in independent sample sets.

"Regularization" is a term known in the art of machine learning and statistics which generally refers to the addition of supplementary information or constraints to an underdetermined system to allow selection of one of the multiplicity of possible solutions of the underdetermined system as the unique solution of an extended system. Depending on the nature of the additional information or constraint applied to "regularize" the problem (i.e. specify which one or subset of the many possible solutions of the unregularized problem should be taken), such methods can be used to select solutions with particular desired properties (e.g. those using fewest input parameters or features) or, in the present context of classifier training from a development sample set, to help avoid overfitting and associated lack of generalization (i.e., selection of a particular solution to a problem that performs very well on training data but only performs very poorly or not all on other datasets). See e.g., https://en.wikipedia.org/wiki/Regularization_(mathematics). One example is repeatedly conducting extreme dropout of the filtered mini-Classifiers with logistic regression training to classification group labels. However, as noted above, other regularization methods are considered equivalent. Indeed it has been shown analytically that dropout regularization of logistic regression training can be cast, at least approximately, as L2 (Tikhonov) regularization with a complex, sample set dependent regularization strength parameter $\lambda$. (S Wager, S Wang, and P Liang, *Dropout Training as Adaptive Regularization*, Advances in Neural Information Processing Systems 25, pages 351-359, 2013 and D Helmbold and P Long. *On the Inductive Bias of Dropout*, JMLR, 16:3403-3454, 2015). In the term "regularized combination method" the "combination" simply refers to the fact that the regularization is performed over combinations of the mini-Classifiers which pass filtering. Hence, the term "regularized combination method" is used to mean a regularization technique applied to combinations of the filtered set of mini-Classifiers so as to avoid overfitting and domination by a particular mini-Classifier.

The performance of the master classifier is then evaluated by how well it classifies the subset of samples forming the test set.

In step e), steps b)-d) are repeated in the programmed computer for different realizations of the separation of the set of samples into test and training sets, thereby generating a plurality of master classifiers, one for each realization of the separation of the set of samples into training and test sets. The performance of the classifier is evaluated for all the realizations of the separation of the development set of samples into training and test sets. If there are some samples which persistently misclassify when in the test set, the process optionally loops back and steps b), c) and d) and e) are repeated with flipped class labels for such misclassified samples.

The method continues with step f) of defining a final classifier from one or a combination of more than one of the plurality of master classifiers. In the present example, the final classifier is defined as a majority vote or ensemble average of all the master classifiers resulting from each separation of the sample set into training and test sets, or alternatively by an average probability cutoff, selecting one Master Classifier that has typical performance, or some other procedure.

Referring now to FIG. 5A, at the top of the figure, the Development Set is the set of samples from one of the two sample sets A and B as described above. The procedure of FIGS. 5A-5B was executed four times, one time to develop Classifier A, one time to develop Classifier B, one time to develop Classifier C, and one time to develop Classifier D.

Definition of Class Labels (Groups)

For Classifier C, the time-to-event data was dichotomized by assigning a class label of "Group1" to patients that died before or at 60 days after beginning of treatment (i.e. poor outcome) and a class label of "Group2" to patients that were alive 60 days after beginning of treatment (i.e. good outcome).

Classifiers A, B and D make use of time-to-event data for Classifier training. In this situation class labels are not obvious and, as shown in FIG. 5, the procedure uses an iterative method to refine class labels at the same time as creating the Classifier (optional "Flip class label of sample" loop) for persistently misclassified samples. An initial guess is made for the class labels in the "define groups" step. The samples are sorted on PFS for Classifiers A and B and on OS for Classifier D. Then, half of the samples with the lowest time-to-event outcome are assigned the "Group1" class label (early death or progression, i.e. poor outcome) while the other half are assigned the "Group2" class label (late death or progression, i.e. good outcome). For each case (Classifiers A, B, and D), a classifier is then constructed using the outcome data and these class labels. This classifier can then be used to generate classifications for all of the development set samples and these are then used as the new class labels for a second iteration of the classifier construction step. This process is iterated until convergence.

Creation and Filtering of Mini-Classifiers

As shown in the flow chart of FIG. 5, the development set samples were split into training and test sets in multiple different random realizations. Six hundred twenty five realizations were used for Classifiers A, B and D while 1275 realizations were used for Classifier C. The procedure of FIG. 5 works best when training classes have the same number of samples. Hence, if classes had different numbers of members, they were split in different ratios into test and training.

Many k-nearest neighbor (kNN) mini-Classifiers (mCs) that use the training set as their reference set were constructed using subsets of all the features (29 features for Classifier A and 274 for Classifiers B. C and D). Subsets of single (parameter s=1) and two mass spectral (MS) features (parameter s=2) were used in the construction of the mCs, yielding a total of 435 mCs created for Classifier A and 37,675 mCs created for Classifiers B, C and D. The k parameters used for the mCs in the different Classifiers is listed in table 5.

TABLE 5

List of k parameters used in the mCs (kNN models) for the 4 developed Classifiers

| Classifier | k |
|---|---|
| A | 11 |
| B | 11 |
| C | 9 |
| D | 9 |

To target a final classifier that has certain performance characteristics, these mCs were filtered as follows. Each mC was applied to its training set and performance metrics were calculated from the resulting classifications of the training set. Only mCs that satisfy thresholds on these performance metrics pass filtering to be used further in the process. The mCs that fail filtering are discarded. Table 6 shows the metric types and the intervals that each mC needs to meet to pass filtering.

TABLE 6

Mini-Classifier metric types and corresponding passing intervals for the 4 developed Classifiers

| Classifier | Metric Type | Passing interval |
|---|---|---|
| A | Hazard ratio on PFS | [2.0-10.0] |
| B | Hazard ratio on PFS | [2.0-10.0] |
| C | Overall accuracy | [0.7-1.0] |
| D | Hazard ratio on OS | [2.2-10.0] |

In the next step in FIG. 5 ("Generate Master Classifier (MC)"), once the filtering of the mCs was complete, the mCs were combined in one master classifier (MC) using a logistic regression trained using the training set class labels. To help avoid overfitting the regression is regularized using extreme drop out with only a small number of the mCs chosen randomly for inclusion in each of the logistic regression iterations. The number of dropout iterations was selected based on the typical number of mCs passing filtering to ensure that each mC was likely to be included within the drop out process multiple times. Ten randomly selected mCs were left in per drop out iteration. Table 7 lists the total number of dropout Iterations performed for the different Classifiers.

Two different methods of combining the results of all dropout iterations were used.

In the first method (weights combination), the weight corresponding to a given mC was averaged over all the dropout iterations that included it. In this way, a combined logistic function was created, with the number of weights equal to the number of mCs that passed filtering plus unity (intercept or bias term). This logistic function provides an output "probability" per Master Classifier.

In the second method (probabilities combination), all the fitted weights, from all the dropout iterations were kept. In this way, a multitude of logistic functions (equal in number to the number of dropout iterations performed, as listed in table 7) made of 11 weights each (10 corresponding to the mCs left in and 1 corresponding to the intercept term), was created. The "probability" outputs from all the logistic functions were then averaged to yield a "probability" per Master Classifier.

TABLE 7

List of the number of dropout iterations and the combining method used in the 4 developed classifiers.

| Classifier | Number of dropout iterations | Combining method |
|---|---|---|
| A | 20,000 | Weights |
| B | 200,000 | Weights |
| C | 100,000 | Probabilities |
| D | 130,000 | Probabilities |

Training/Test Splits

The use of multiple training/test splits avoids selection of a single, particularly advantageous or difficult, training set for Classifier creation and avoids bias in performance assessment from testing on a test set that could be especially easy or difficult to classify.

Master Classifiers (MC)

The output of each MC is a probability of being in one of the two training classes (Group1 or Group2).

For Classifier C, these MC probabilities were averaged to yield one average probability per sample. When working with samples in the development set, this approach was adjusted to average over MCs for which a given sample is not included in the training set ("out-of-bag" estimate). These average probabilities were converted Into a binary classification by applying a threshold (cutoff). ROC and precision curves were used to investigate the performance of the whole family of Classifiers created from the procedure of FIG. 5 which are parameterized by different choices of cutoff and to help choose a cutoff suitable for the clinical question.

For Classifiers A, B and D classifications were assigned by majority vote of the individual MC labels obtained with a cutoff of 0.5 applied to the output "probability" of each MC. This process was modified to incorporate only MCs where the sample was not in the training set for samples in the development set (modified or "out-of-bag" majority vote).

Results

The tests described in this document, in one configuration, consist of logical combinations of the outputs of subsidiary mass spectral classifiers, referred to as Classifier A, Classifier B, Classifier C and Classifier D, each of which produce a class label for the spectrum. Three of such tests are described in this document, Tests 1, 2 and 3, which are described below.

Classifier A

This classifier was designed using, as development set, the 96 samples in Set A that were not simultaneously classified as IS2 "Late" (a classification procedure described in Example 1 of U.S. Pat. No. 10,007,766, described as "full set, approach 1 Classifier" or "IS2") and were from patients with Performance Status (PS) 0. The subset of 29 mass spectral features associated with Immune Response Type 2 (see Appendix B) were used in the Diagnostic Cortex platform (FIG. 5) to create a classifier able to stratify patients into two groups with better and worse PFS. No feature deselection was used, i.e., all 29 mass spectral features associated with Immune Response Type 2 were used at each step of refinement of the class labels and Classifier A. From the 625 generated train/test splits of the development set, only 554 had enough mini-Classifiers passing the filtering step to produce a Master Classifier. Hence, the "final test" of Classifier A consists of an ensemble average (majority vote) over 554 Master Classifiers. If a tie exists in the number of MCs giving a classification of Group1 versus the number of MCs giving the classification of Group2, a final classification Group2 is given to the sample. Fifty (43%) samples of Set A were assigned to the poor performing group ("Group1" label) and the remaining 66 (57%) samples were assigned to the good performing group ("Group2" label).

Classifier B

This classifier was designed using, as development set, the 76 samples in Set A that were not simultaneously classified as Group1 in Classifier A and IS2 "Early", see example 1 of U.S. Pat. No. 10,007,766, described as "full set, approach 1 Classifier". All of the 274 available mass spectral features were used in the Diagnostic Cortex platform to create a classifier able to stratify patients into two groups with better and worse PFS. No feature deselection was used, i.e., all 274 mass spectral features were used at each step of refinement of the class labels and Classifier B. All the 625 generated train/test splits of the development set had enough mini-Classifiers passing the filtering step to produce a Master Classifier. Hence, Classifier B consists of an ensemble average (majority vote) over 625 Master Classifiers. Forty-five (39%) samples of Set A were assigned to the poor performing group ("Group1" label) and the remaining 71 (61%) samples were assigned to the good performing group ("Group2" label).

Classifier C

This classifier was designed using, as development set, all of the 116 samples of Set A. All of the 274 available mass spectral features (Appendix A) were used in the Diagnostic Cortex platform to create a classifier able to distinguish between patients whose death would happen at or before 60 days after treatment started and patients whose death would happen after 60 days from treatment starting date. No refinement of the class labels (label flip process) was implemented for this classifier. All 274 mass spectral features were used. All the 1,275 generated train/test splits of the development set had enough mini-Classifiers passing the filtering step to produce a Master Classifier. Hence, Classifier C consists of an ensemble average over 1,275 Master Classifier output probabilities followed by the application of a cut-off.

Figure 6A:
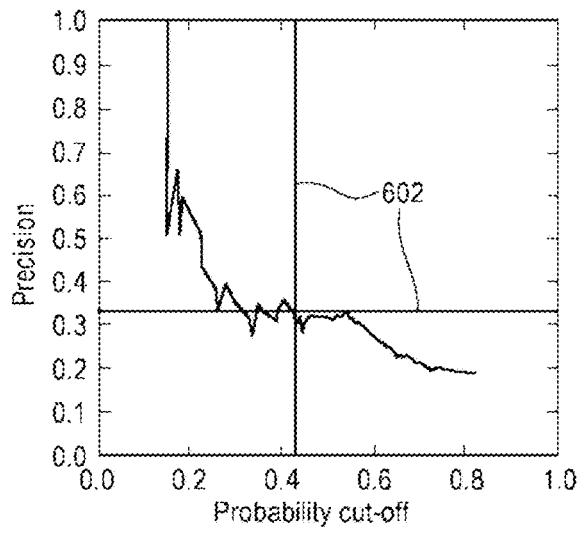
FIGS. 6A-6C: Precision curves obtained by scanning the different averaged probability cut-offs accessible in the development set.
Figure 6B:
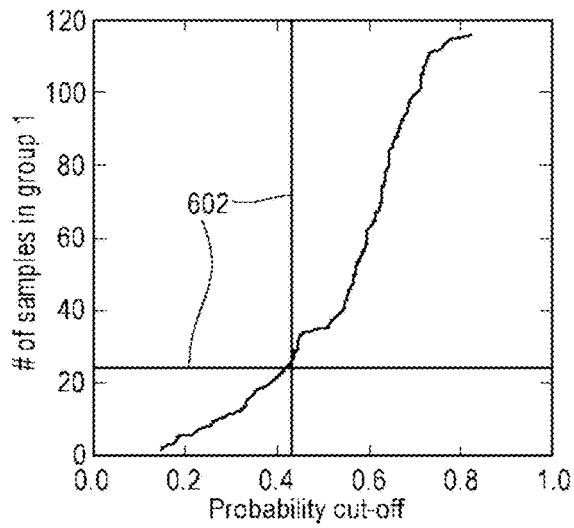
Figure 6C:
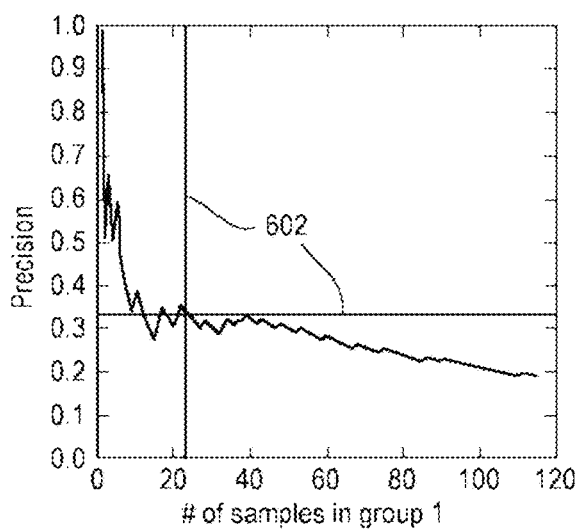

FIG. 6A shows the precision curve for Group1, plotted using the 116 samples used in development and obtained by scanning the different averaged probability cut-offs accessible in the data. FIG. 6B shows the number of samples assigned to Group1 as function of the probability cutoff and FIG. 6C shows the achievable points in the precision vs number of samples assigned to Group1 space. A probability cut-off of 0.43271 was chosen, corresponding to a precision of 33.3% and to 24 samples (21%) assigned to Group1 (the remainder 92 (79%) assigned to Group2). The lines 602 allow identification of the chosen point in each of the parameter spaces.

FIG. 7 shows the ROC curve, plotted using the same 116 development samples. The corresponding area under the curve (AUC) is 0.687. In this plot it is assumed that the "positive" classification label (related to sensitivity and corresponding to a smaller averaged probability) is Group1; and that the "negative" classification label (related to specificity and corresponding to a higher averaged probability) is Group2. The open circle 700 shows the chosen point in terms of sensitivity (36.4%) and specificity (83.0%).

Classifier D

This classifier was designed using, as development set, the 113 samples of Set B. All of the 274 available mass spectral features were used in the Diagnostic Cortex platform to create a classifier able to stratify patients into two groups with better and worse OS. No feature deselection was used, i.e., all 274 mass spectral features were used at each step of refinement of the class labels and Classifier D. All the 625 generated train/test splits of the development set had enough mini-Classifiers passing the filtering step to produce a MC. Hence, Classifier D consists of an ensemble average (majority vote) over 625 Master Classifiers.

Forty-three samples of the whole Set B were assigned to the poor performing group ("Group1" label) and the remaining 70 samples were assigned to the good performing group ("Group2" label). Baseline characteristics and Kaplan-Meier plots of OS and TTP split by Classifier D classifications of Set B are shown in Appendix C of our priority provisional applications, as well as the corresponding survival statistics.

When applying this Classifier to Set A, 59 (51%) samples were assigned to the "Group1" label and the remaining 57 (49) samples were assigned the "Group2" label.

Test 1

Test 1, in one format, consists of a logical combination of outputs of Classifiers A and D alone, or alternatively a combination of Classifiers A, B and D. Test 1 is the principal test for primary immune resistance. In one configuration, where it uses a logical combination of Classifiers A, B and D. Test 1 assigns one of three classification labels, Bad, Intermediate, or Good to a patient's sample.

Figure 8:
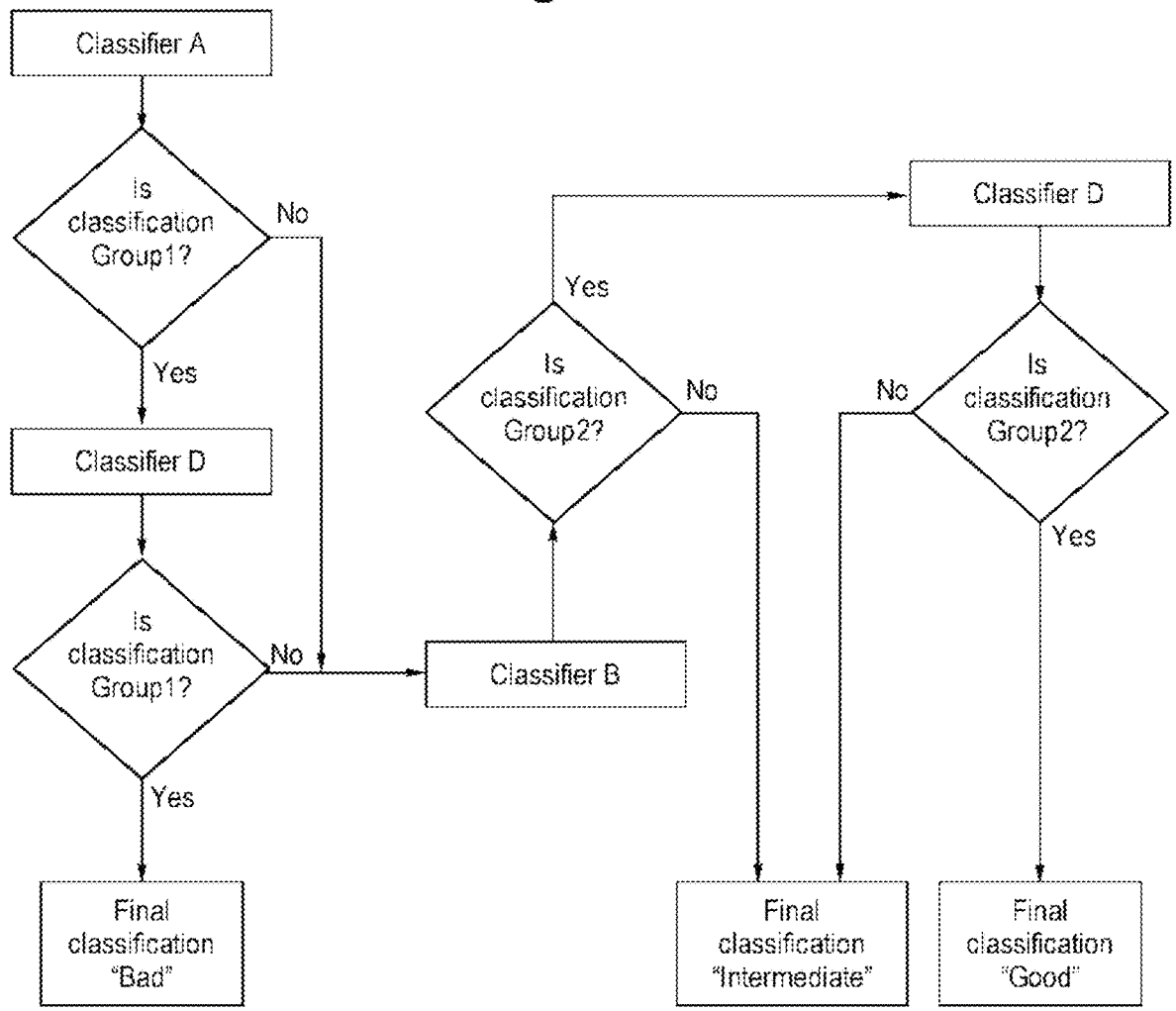
FIG. 8 is a diagram showing the logic for combining Classifiers A, B and D in a ternary classification schema for Test 1. In one variation, only Classifiers A and D could be used to generate the class label Bad indicating primary immune resistance.
Figure 10A:
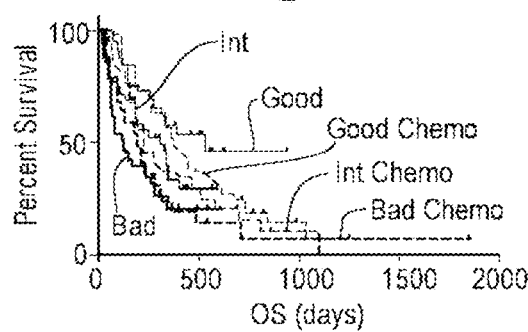
FIG. 10A-10F: Kaplan-Meier plots of OS and PFS split by Test 1 classifications of Set A and Set C (whole set, docetaxel and pemetrexed arms).
Figure 10B:
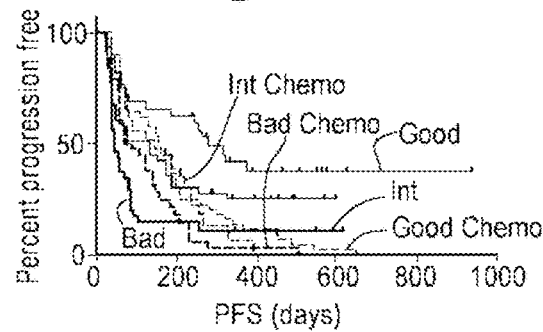
Figure 10C:
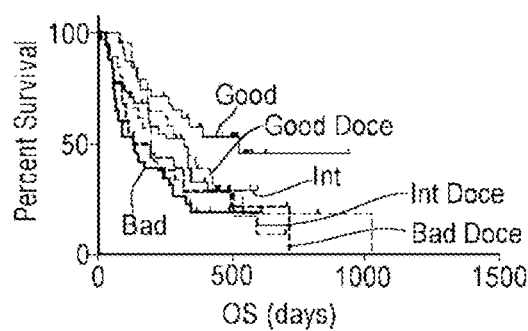
Figure 10D:
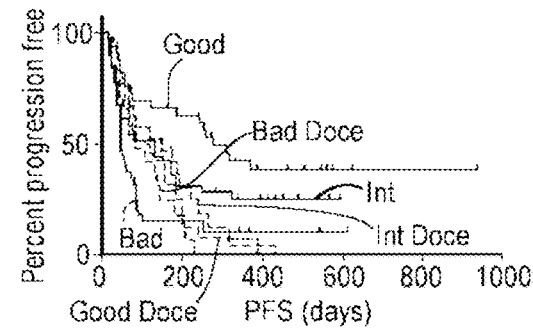
Figure 10E:
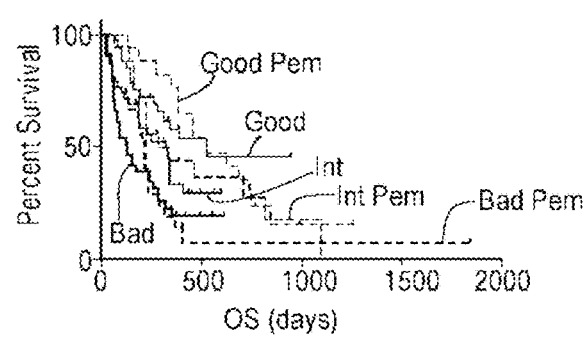
Figure 10F:
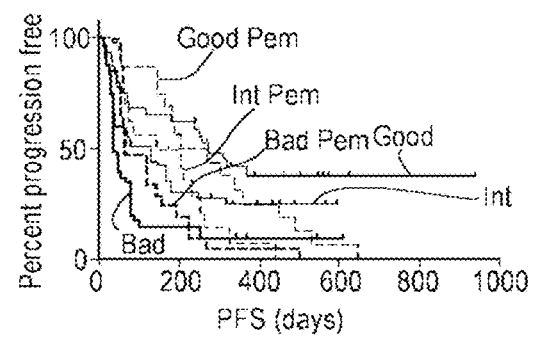
Figure 11A:
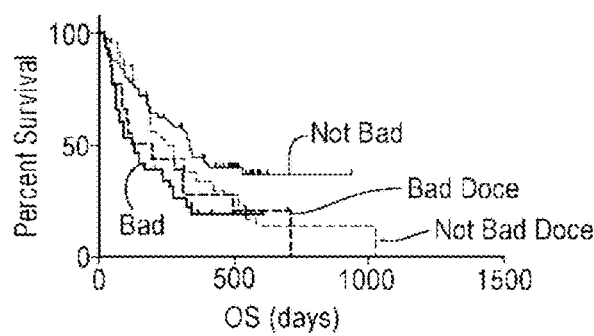
FIG. 11A-11D: Kaplan-Meier plots of OS and PFS split by binary combinations of Test 1 classifications of Set A and Set C (docetaxel arm).
Figure 11B:
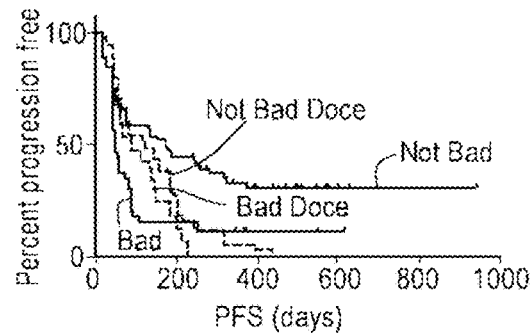
Figure 11C:
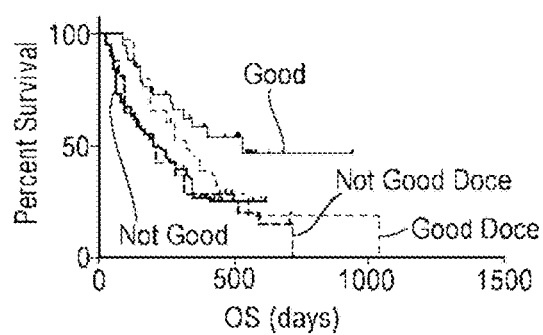
Figure 11D:
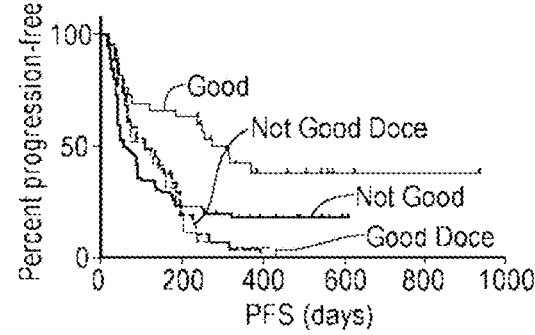

If a sample is classified as Group1 by both Classifiers A and D, It is given a final classification of "Bad". If both classifications from Classifiers B and D are Group2, the final classification is set to "Good". All other samples are given a final classification of "Intermediate". This combination scheme is shown in FIG. 8. If the final class label of "Bad" or the equivalent is assigned to the spectrum of a sample in accordance with Test 1 the patient is predicted to be primary immune resistant, as defined in the Introduction of this document. Since this Bad label can be produced by just Classifiers A and D, in one configuration of the test only these two Classifiers are used. If the final class label is "Good or the equivalent, the patient is predicted to have very good outcomes on immune monotherapy.

Forty-one (35%) samples of the whole Set A were assigned to the "Bad" group, 43 (37%) to the "Intermediate" group and the remaining 32 (28%) samples were assigned to the "Good" group. The baseline clinical characteristics of Set A split by Test 1 classifications are listed in table 8. Kaplan-Meier plots of OS and PFS split by Test 1 classifications of Set A (and binary combinations of classification labels) are shown in FIGS. 9A-9F. Hazard ratios (HRs), Cox p values and log-rank p values obtained when comparing the time-to-event data between the classification groups and their binary combinations are shown in table 9 for OS and in table 10 for PFS. Hazard ratios (HRs) and cox p values, adjusted for PS, smoking status, histology and PD-L1 status and obtained when comparing the time-to-event data (OS and PFS) between the Bad vs Not Bad binary combination are shown in table 11 and between the Not Good vs Good binary combination are shown in table 12. The OS and PFS medians are shown in table 13 for each of the classification groups and for their binary combinations.

TABLE 8 baseline clinical characteristics of Set A split by Test 1 classifications

| | | Bad (N = 41) n (%) | Intermediate (N = 43) n (%) | Good (N = 32) n (%) | P value |
|---|---|---|---|---|---|
| Gender | Male | 25 (61) | 22 (51) | 19 (59) | 0.649 |
| | Female | 16 (39) | 21 (49) | 13 (41) | |
| Age | Median (Range) | 68 (52-83) | 63 (43-80) | 64 (49-82) | — |
| Response | CR | 0 (0) | 0 (0) | 1 (3) | <0.001 |
| | PR | 4 (10) | 4 (9) | 8 (25) | |
| | SD | 1 (2) | 11 (26) | 7 (22) | |
| | PD | 35 (85) | 21 (49) | 9 (28) | |
| | NA | 1 (2) | 7 (16) | 7 (22) | |
| Histology | Two primary tumors | 1 (2) | 1 (2) | 0 (0) | 0.474 |
| | Adenocarcinoma | 25 (61) | 27 (63) | 25 (78) | |
| | NSCLC-NEC | 0 (0) | 2 (5) | 1 (3) | |
| | NSCLC-NOS | 2 (5) | 4 (9) | 2 (6) | |
| | Squamous | 13 (32) | 9 (21) | 4 (13) | |
| Performance Status | 0 | 8 (20) | 13 (30) | 15 (47) | 0.112 |
| | 1 | 22 (54) | 24 (56) | 14 (44) | |
| | 2 | 8 (20) | 3 (7) | 1 (3) | |
| | 3 | 2 (5) | 1 (2) | 0 (0) | |
| | NA | 1 (2) | 2 (5) | 2 (6) | |
| Smoking Status | Current | 10 (24) | 6 (14) | 7 (22) | 0.431 |
| | Former | 26 (63) | 35 (81) | 20 (63) | |
| | Never | 4 (10) | 2 (5) | 4 (13) | |
| | NA | 1 (2) | 0 (0) | 1 (3) | |
| Brain Metastases at start of Itx | No | 31 (76) | 32 (74) | 24 (75) | >0.999 |
| | Yes | 10 (24) | 11 (26) | 8 (25) | |
| Previous Rtx | No | 13 (32) | 15 (35) | 15 (47) | 0.389 |
| | Yes | 28 (68) | 28 (65) | 17 (53) | |
| Previous Thoracic Rtx | No | 30 (73) | 24 (56) | 25 (78) | 0.087 |
| | Yes | 11 (27) | 19 (44) | 7 (22) | |
| VeriStrat classification† | Good | 16 (39) | 40 (93) | 32 (100) | <0.001 |
| | Poor | 25 (61) | 3 (7) | 0 (0) | |
| PD-L1 status | Positive (≥1%) | 10 (24) | 12 (28) | 10 (31) | 0.154 |
| | Negative (<1%) | 16 (39) | 17 (40) | 5 (16) | |
| | NA | 15 (37) | 14 (33) | 17 (53) | |

†VeriStrat Classifier applied to Deep MALDI average spectra

TABLE 9

Statistics for OS by Test 1 classification (of Set A) bad vs intermediate vs good and by combinations not bad vs bad and good vs not good

| | CP HR (95% CI) | Cox p value | Log-rank p value |
|---|---|---|---|
| Intermediate vs Bad | 0.63 (0.38-1.06) | 0.083 | 0.080 |
| Good vs Intermediate | 0.56 (0.29-1.05) | 0.072 | 0.068 |
| Good vs Bad | 0.34 (0.19-0.64) | <0.001 | <0.001 |
| Not Bad vs Bad | 0.48 (0.30-0.77) | 0.002 | 0.002 |
| Good vs Not Good | 0.45 (0.25-0.79) | 0.006 | 0.004 |

TABLE 10

Statistics for PFS by Test 1 classification (of Set A) bad vs intermediate vs good and by combinations not bad vs bad and good vs not good

| | CP HR (95% CI) | Cox p value | Log-rank p value |
|---|---|---|---|
| Intermediate vs Bad | 0.59 (0.37-0.96) | 0.035 | 0.033 |
| Good vs Intermediate | 0.58 (0.33-1.02) | 0.059 | 0.056 |
| Good vs Bad | 0.33 (0.19-0.58) | <0.001 | <0.001 |
| Not Bad vs Bad | 0.46 (0.30-0.71) | <0.001 | <0.001 |
| Good vs Not Good | 0.45 (0.27-0.76) | 0.003 | 0.002 |

TABLE 11

Multivariate statistics for OS and PFS by Test 1 Bad vs Not Bad binary combination of the classification groups (of Set A)

| | OS | | PFS | |
|---|---|---|---|---|
| HR | (95% CI) | p value | HR (95% CI) | p value |
| PIR Test1 (NotBad vs Bad) | 0.64 (0.37-1.11) | 0.113 | 0.55 (0.33-0.92) | 0.022 |
| ECOG PS (1 vs 0) | 1.69 (0.90-3.17) | 0.106 | 1.35 (0.78-2.32) | 0.284 |
| ECOG PS (≥2 vs 0) | 4.67 (2.05-10.64) | <0.001 | 2.42 (1.15-5.08) | 0.020 |
| Never vs ever smoker | 2.07 (0.92-4.69) | 0.081 | 1.30 (0.58-2.89) | 0.525 |
| Squamous vs Non-squamous | 1.04 (0.58-1.89) | 0.886 | 1.04 (0.62-1.76) | 0.882 |
| PD-L1 (<1% vs ≥1%) | 1.64 (0.83-3.23) | 0.155 | 1.35 (0.72-2.54) | 0.354 |
| PD-L1 (NA vs ≥1%) | 0.81 (0.40-1.63) | 0.559 | 0.82 (0.44-1.53) | 0.528 |

TABLE 12

Multivariate statistics for OS and PFS by Test 1 Not Good vs Good binary combination of the classification groups (of Set A)

| | OS | | PFS | |
|---|---|---|---|---|
| | HR (95% CI) | p value | HR (95% CI) | p value |
| PIR Test1 (Good vs NotGood) | 0.65 (0.32-1.29) | 0.216 | 0.65 (0.36-1.17) | 0.148 |
| ECOG PS (1 vs 0) | 1.63 (0.86-3.09) | 0.133 | 1.37 (0.80-2.36) | 0.257 |
| ECOG PS (≥2 vs 0) | 4.74 (2.08-10.80) | <0.001 | 2.54 (1.22-5.30) | 0.013 |
| Never vs ever smoker | 2.32 (1.00-5.37) | 0.051 | 1.43 (0.63-3.23) | 0.390 |
| Squamous vs Non-squamous | 1.04 (0.57-1.88) | 0.899 | 1.06 (0.63-1.79) | 0.831 |
| PD-L1 (<1% vs ≥1%) | 1.76 (0.91-3.42) | 0.095 | 1.63 (0.89-2.97) | 0.113 |
| PD-L1 (NA vs ≥1%) | 0.91 (0.46-1.80) | 0.777 | 0.96 (0.52-1.78) | 0.893 |

TABLE 13

Medians for OS and PFS by Test 1 classification (of Set A) bad vs intermediate vs good and by combinations not bad vs bad and good vs not good

| | Number of samples | Median OS (95% CI) days | Median PFS (95% CI) days |
|---|---|---|---|
| Bad | 41 | 132 (61-240) | 43 (39-69) |
| Intermediate | 43 | 316 (179-346) | 130 (43-172) |
| Good | 32 | 528 (260-undefined) | 276 (75-undefined) |
| Not Bad | 75 | 338 (248-528) | 170 (75-258) |
| Not Good | 84 | 183 (130-280) | 55 (42-83) |

Kaplan-Meier plots of OS and PFS split by Test 1 classifications of Set A and Set C (whole set, docetaxel and pemetrexed arms) are shown in FIGS. 10A-10F. Kaplan-Meier plots of OS and PFS split by binary combinations of Test 1 classifications of Set A and Set C (docetaxel arm) are shown in FIGS. 11A-11D.

We also evaluated the results of the binary combinations, Bad vs. Not Bad (Intermediate and Good), and Good vs. Not Good (Intermediate and Bad). This test assigned 34% of the development cohort to the Bad group and 27% to the Good group. It is noteworthy that the medians in the Bad group are very short indeed, i.e. 1.4 months for PFS and 4.3 months for OS, and 85% of patients in the Bad group had a best response of PD. In comparison to the chemotherapy arm of PROSE the Bad group does appear to do worse on immune therapy than on chemotherapy, indicating that we have indeed identified a group of patients where checkpoint inhibition may not provide the advantage seen in the other groups. Although these data are not from a randomized study, we believe that the test is likely to be predictive for anti-PD1 vs chemotherapy. The Good group defined by Test 1 had excellent outcomes, with median OS in excess of 17 months and median PFS of 9.1 months. The proportion of patients experiencing PD as best response in this group was only 28% and the response rate (CR+PR) was 28%. No significant association of Test 1 with baseline clinical characteristics was found for the ternary classification, although Bad vs Not Bad classification was associated with performance status. However, multivariate analysis indicated that test classification (Bad vs Not Bad or Good vs Not Good) remained numerically an independent predictor of OS and PFS when adjusted for other prognostic factors including smoking status, histology, performance status, and PD-L1 status.

To assess the reproducibility of Test 1, the Classifiers were run on the average spectra obtained from two rounds of spectral acquisition of an external set of 98 samples. These pre-treatment samples were collected from Non-Small Cell Lung Cancer (NSCLC) patients receiving nivolumab. The classifications obtained for Round1 and Round2 are compared in table 14 for Test 1 three-way classifications, in table 15 for the binary combination Bad vs Not Bad, and in table 16 for the binary combination Not Good vs Good. Classification concordance is 85% for the three-way classifications, 91% for the Bad/Not Bad combination and 93% for the Not Good/Good combination.

TABLE 14

Reproducibility of Test 1 (three-way classifications)

| | | Round 2 | | |
|---|---|---|---|---|
| | | Bad (N =37) | Intermediate (N = 30) | Good (N = 31) |
| Round 1 | Bad (N = 40) | 34 | 6 | 0 |
| | Intermediate (N = 22) | 2 | 19 | 1 |
| | Good (N-36) | 1 | 5 | 30 |

TABLE 15

Reproducibility of Test 1 (Bad vs Not Bad binary combination)

| | | Round2 | |
|---|---|---|---|
| | | Bad (N = 37) | Not Bad (N = 61) |
| Round1 | Bad (N = 40) | 34 | 6 |
| | Not Bad (N = 58) | 3 | 55 |

TABLE 16

Reproducibility of Test 1 (Not Good vs Good binary combination)

| | | Round2 | |
|---|---|---|---|
| | | Not Good (N = 67) | Good (N = 31) |
| Round1 | Not Good (N = 62) | 61 | 1 |
| | Good (N = 36) | 6 | 30 |

Relation to Protein Functional Groups
A. Original Results

Protein Set Enrichment Analysis (PSEA), a method inspired by gene set enrichment analysis, was used to look for an association of the classifications from Test 1 with biological processes. To do this, an independent set of 49 samples was used where paired deep MALDI spectra and protein panel (Somalogic, Boulder, CO) results were available. Of the 49 samples, 22 (45%) classified as Bad, 10 (20%) as Intermediate and 17 (35%) as Good. More details of the analysis method are described in our prior U.S. Pat. No. 10,007,788, Example 8; see also Mootha, et al., *PGC-1α-responsive genes involved in oxidative phosphorylation are coordinately downregulated in human diabetes.* Nat Genet. 2003; 34(3):267-73 and Subramanian, et al., *Gene set enrichment analysis: A knowedge-based approach for interpreting genome-wide expression profiles.* Proc Natl Acad Sci USA 2005; 102(43): 15545-50, the content of which are incorporated by reference herein.

The results for the 29 different biological processes tested are shown in table 17 when looking at the biological association of the Bad vs Not Bad binary combination. P values are not corrected for multiple comparisons. At the $\alpha=0.05$ significance level, associations of the test classifications were found with complement, wound healing, acute phase and extracellular matrix. In addition, at the $\alpha=0.10$ significance level, associations were found with acute inflammation, interleukin-10, immune response, immune response type 2 and angiogenesis.

TABLE 17

Results of Protein Set Enrichment Analysis for Test 1 binary combinations Bad vs Not Bad

| Biological Process | Enrichment | p value |
|---|---|---|
| Acute inflammation | 0.388 | 0.051 |
| Innate Immune Response | 0.471 | 0.413 |
| Adaptive immune response | 0.228 | 0.918 |
| Glycolytic Processes | −0.346 | 0.734 |
| Immune T-cells | −0.224 | 0.631 |
| Immune B-cells | 0.227 | 0.871 |
| Cell cycle | 0.173 | 0.962 |
| NK regulation | −0.410 | 0.384 |
| Complement | 0.604 | 0.002 |
| Cancer - experimental | 0.728 | 0.557 |
| Acute response | 0.468 | 0.224 |
| Cytokine activity | −0.296 | 0.326 |
| Wound healing | −0.446 | 0.017 |
| Interferon | 0.174 | 0.951 |
| Interleukin-10 | 0.290 | 0.079 |
| GFR* signaling | −0.269 | 0.139 |
| Immune response | 0.283 | 0.056 |
| Immune Response Type 1 | 0.451 | 0.422 |
| Immune Response Type 2 | 0.731 | 0.074 |
| Immune Response - Complement | −0.191 | 0.697 |
| Immune Response - Complement - Acute | −0.268 | 0.108 |
| Acute phase | 0.628 | 0.002 |
| Hypoxia | 0.183 | 0.938 |
| Cancer | 0.181 | 0.702 |
| Cell adhesion | −0.271 | 0.227 |
| Mesenchymal transition | 0.361 | 0.572 |
| Extracellular matrix - restricted source, UNIPROT | −0.553 | 0.009 |
| Extracellular matrix - from different sources | −0.394 | 0.049 |
| Angiogenesis | −0.329 | 0.088 |

*GFR = growth factor receptor

The results obtained when looking at biological associations of the Not Good vs Good binary combination are shown in table 18. P values are not corrected for multiple comparisons. At the $\alpha=0.05$ significance level, associations of the Not Good vs Good binary labels were found with innate immune response, acute response and acute phase. In addition, at the $\alpha=0.10$ significance level, associations were found with acute inflammation and wound healing.

TABLE 18

Results of Protein Set Enrichment Analysis for Test 1 binary combinations Not Good vs Good

| Biological Process | Enrichment score | p value |
|---|---|---|
| Acute inflammation | 0.370 | 0.079 |
| Innate Immune Response | 0.674 | 0.042 |
| Adaptive immune response | 0.379 | 0.409 |
| Glycolytic Processes | −0.380 | 0.630 |
| Immune T-cells | −0.296 | 0.218 |
| Immune B-cells | 0.228 | 0.866 |
| Cell cycle | 0.197 | 0.870 |

TABLE 18-continued

Results of Protein Set Enrichment Analysis for Test 1 binary combinations Not Good vs Good

| Biological Process | Enrichment score | p value |
|---|---|---|
| NK regulation | −0.481 | 0.217 |
| Complement | 0.411 | 0.161 |
| Cancer - experimental | 0.894 | 0.188 |
| Acute response | 0.604 | 0.031 |
| Cytokine activity | −0.257 | 0.523 |
| Wound healing | −0.386 | 0.082 |
| 00Interferon | 0.149 | 0.990 |
| Interleukin-10 | 0.233 | 0.366 |
| GFR* signaling | −0.235 | 0.324 |
| Immune response | 0.255 | 0.146 |
| Immune Response Type 1 | 0.194 | 0.996 |
| Immune Response Type 2 | 0.477 | 0.565 |
| Immune Response - Complement | −0.191 | 0.693 |
| Immune Response - Complement - Acute | −0.243 | 0.234 |
| Acute phase | 0.552 | 0.018 |
| Hypoxia | 0.214 | 0.821 |
| Cancer | 0.198 | 0.484 |
| Cell adhesion | −0.285 | 0.165 |
| Mesenchymal transition | −0.286 | 0.841 |
| Extracellular matrix - restricted source, UNIPROT | −0.369 | 0.270 |
| Extracellular matrix - from different sources | −0.273 | 0.439 |
| Angiogenesis | −0.197 | 0.833 |

*GFR = growth factor receptor

B. Changes to the PSE Analysis

We have developed a new way to apply the PSEA approach, since we now have protein panel data (again from SomaLogic) for an additional set of 100 samples from patients with NSCLC. These data are in addition to the set of 49 samples that we used in the original PSEA results explained immediately above.

For the sample set of 100 samples, we have discovered that it Is advantageous to split the sample set in half, calculate the PSEA enrichment score (as in Subramanian et al. and as was done above) for each discrete set of 50 samples and then average the two enrichment scores together to get one score for the whole set of 100 samples. To reduce the dependence of this process on the precise split of the samples into two halves, we repeat this for 25 random splits of the sample set into halves and also average over all 25 splits. This gives us a new enrichment score statistic to assess association between each biological process and the test classifications.

To combine this assessment from the data for the N=100 sample set with that from the previous N=49 sample set, we normalize the enrichment score for each sample set (we use the original enrichment score statistic for the N=49 sample set, as this is too small to gain from splitting in half) and average the normalized enrichment scores together to get an overall enrichment score spanning the N=100 and N=49 sample sets. The p value of association is calculated by generating the null distribution via permutation of the test classifications, just as before. The only difference is that we now do this for both sample sets and use the new combined metric. Both the splitting of the N=100 new data set and its incorporation with the old N=49 dataset give us Increased power to detect reliable association with the biological processes.

In addition to this, we have reworked the definitions of the protein sets associated with the biologicalprocessestotrytomakethemmorespecificandtocoversomeadditional processes of potential interest.

We have used this, new procedure and new protein set definitions to look at the association of Test classifications (Bad vs Not Bad) with biological processes.

The results are in the Table 17A below. This is considered an improved version of Table 17 above.

TABLE 17A

Results of Protein Set Enrichment Analysis for Test 1 binary combinations Bad vs Not Bad, using changed PSE Analysis Method

| Biological Process | p value of association |
| --- | --- |
| Acute phase response | <0.0001 |
| Acute inflammatory response | 0.0001 |
| Wound-healing | 0.0002 |
| Complement activation | 0.0005 |
| Innate immune response | 0.0014 |
| Chronic Inflammatory response | 0.0044 |
| Extra cellular matrix | 0.0231 |
| IFN-type-1 | 0.0315 |
| Cellular component morphogenesis | 0.0317 |
| Immune tolerance and suppression | 0.0526 |
| B cell mediated immunity | 0.0526 |
| Angiogenesis | 0.0753 |
| NK cell mediated immunity | 0.1222 |
| Behavior | 0.1270 |
| Cytokine production involved in immune response | 0.3198 |
| Glycolysis and positive regulators | 0.3560 |
| Epithelial-Mesenchymal Transition | 0.4548 |
| Type17 immune response | 0.4668 |
| Type1 immune response | 0.5102 |
| Type2 immune response 2 | 0.7791 |
| Response to hypoxia | 0.9287 |
| Tcell mediated immunity | 0.9861 |
| IFN-Gamma | 0.9884 |

Figure 12:
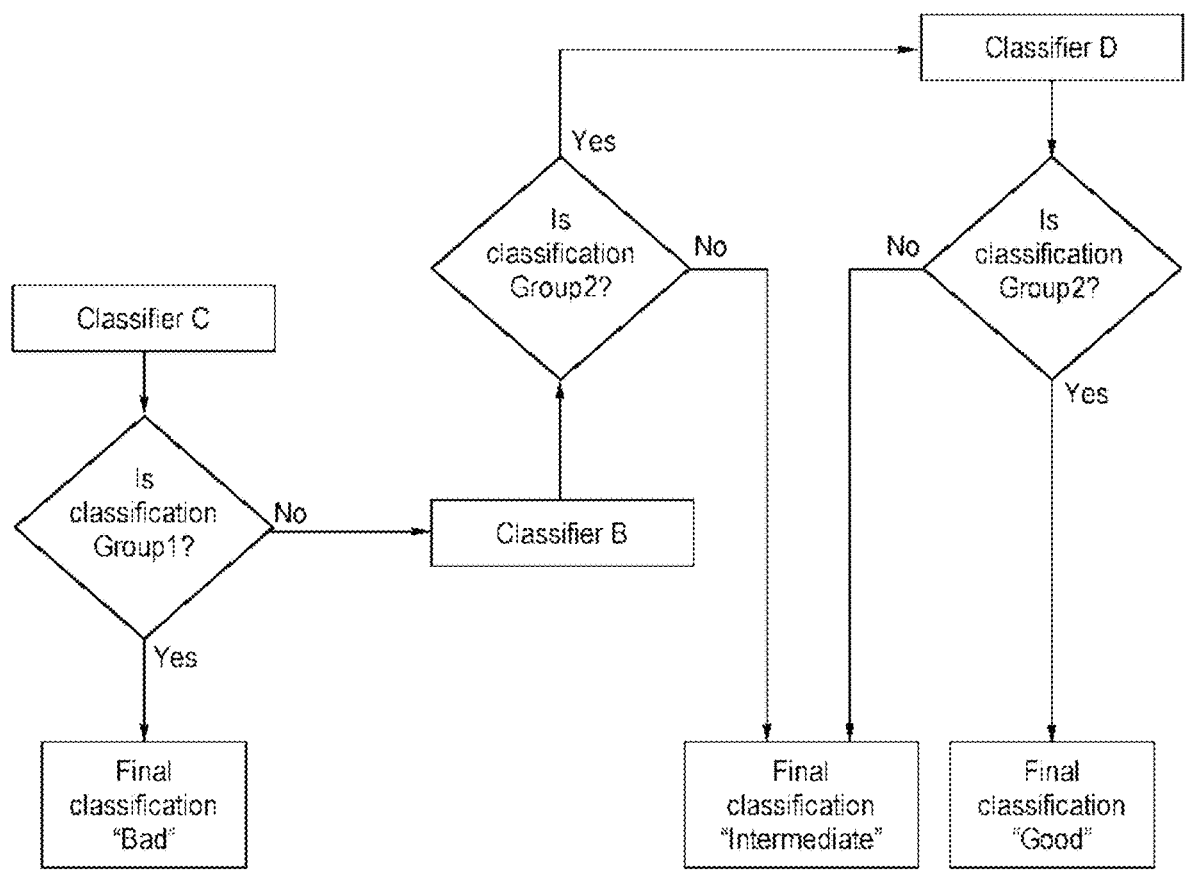
FIG. 12 is a diagram showing the logic for combining Classifiers C, B and D in a ternary classification schema for Test 2. In one variation, only Classifier C could be used, to generate the class label Bad, indicating poor prognosis on anti-PD-1 and anti-PD-L1 therapies or alternative chemotherapies.
Figure 13A:
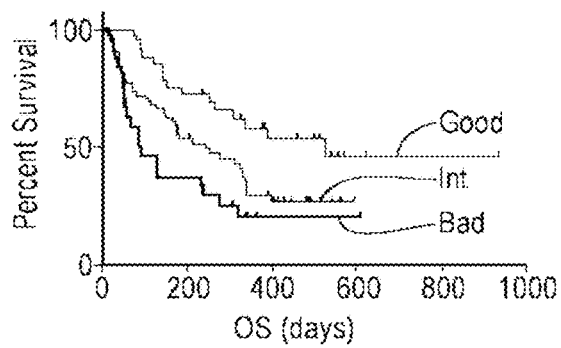
FIG. 13A-13F: Kaplan-Meier plots of OS and PFS split by Test 2 classifications (and their binary combinations) of Set A.
Figure 13B:
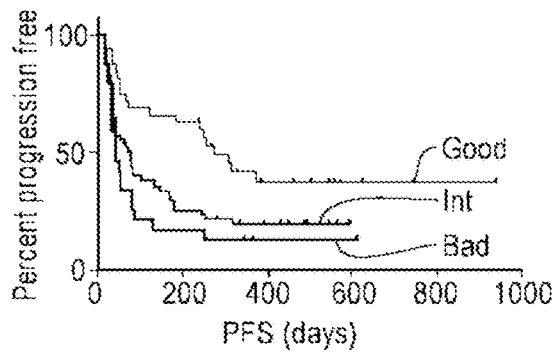
Figure 13C:
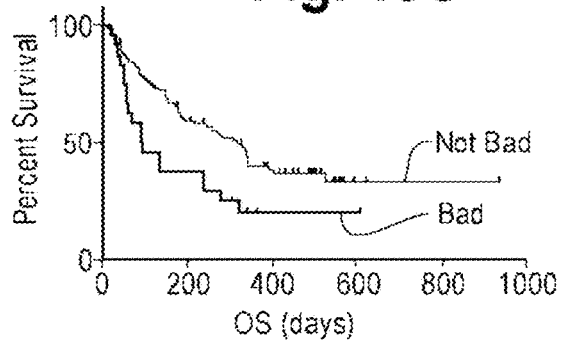
Figure 13D:
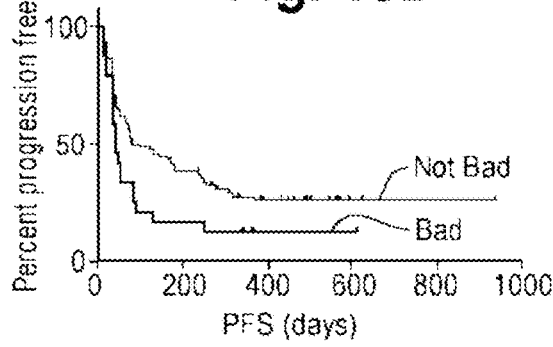
Figure 13E:
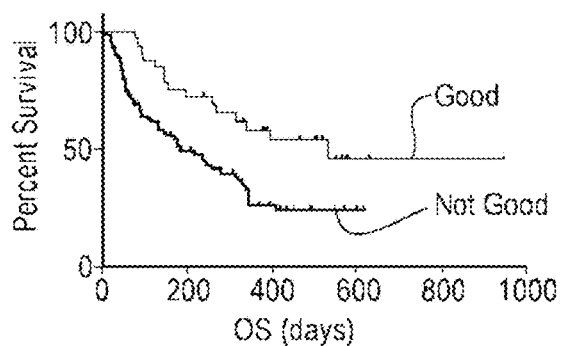
Figure 13F:
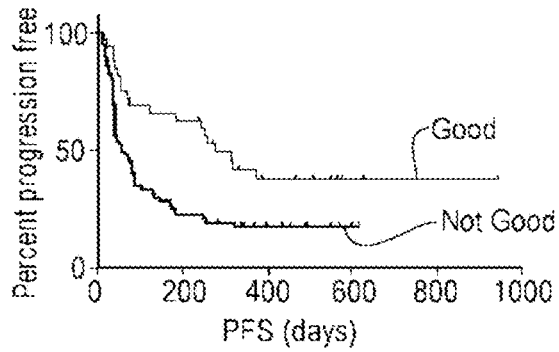
Figure 14A:
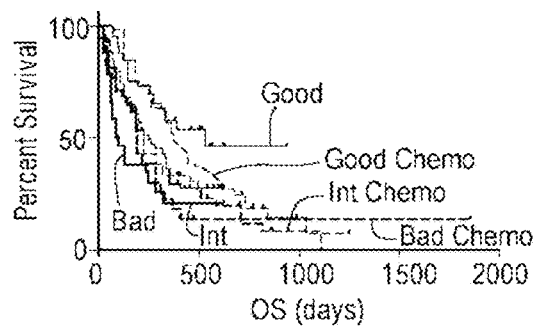
FIG. 14A-14F: Kaplan-Meier plots of OS and PFS split by Test 2 classifications of Set A and Set C (whole set, docetaxel and pemetrexed arms).
Figure 14B:
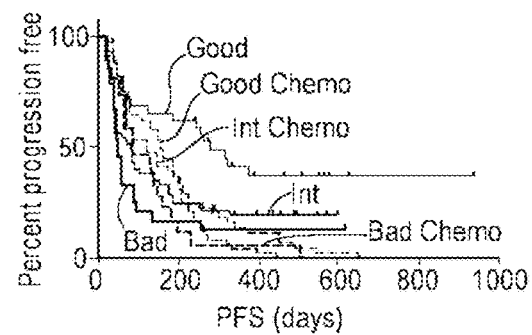
Figure 14C:
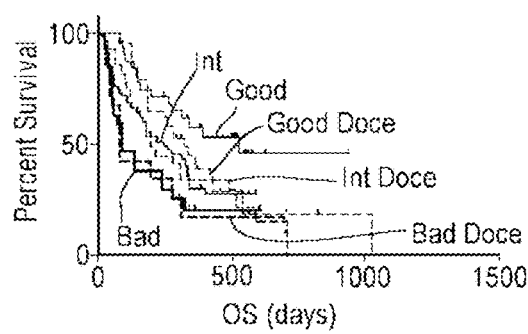
Figure 14D:
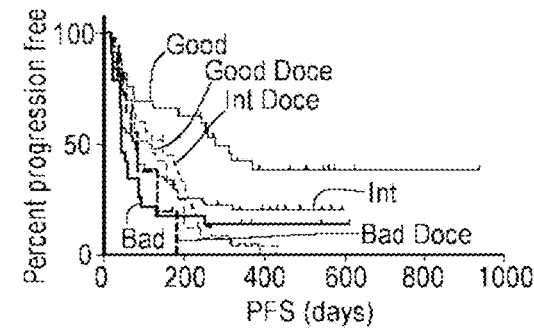
Figure 14E:
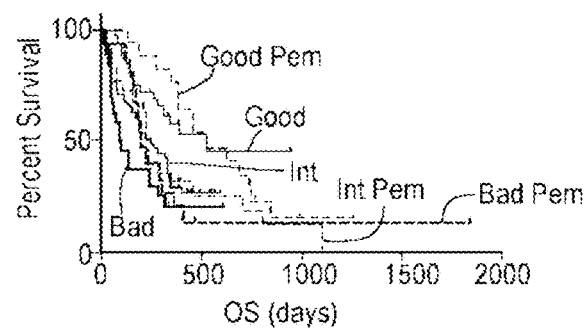
Figure 14F:
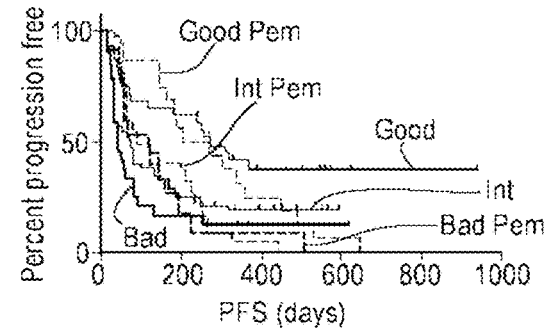
Figure 15A:
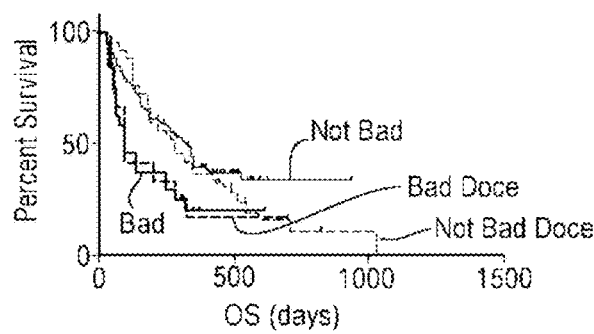
FIG. 15A-15D: Kaplan-Meier plots of OS and PFS split by binary combinations of Test 2 classifications of Set A and Set C (docetaxel arm)
Figure 15B:
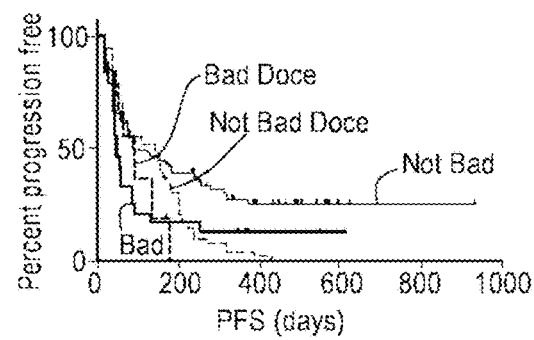
Figure 15C:
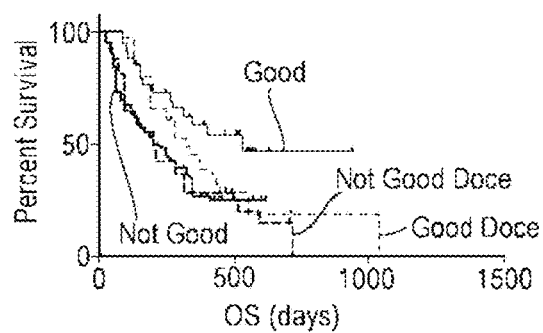
Figure 15D:
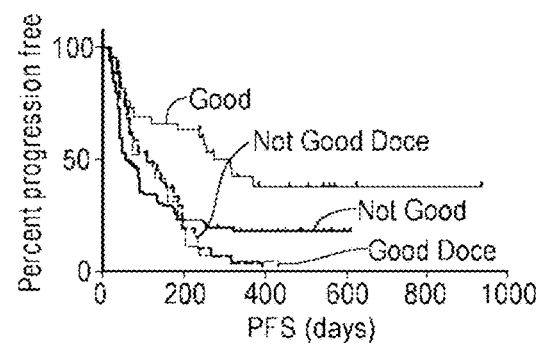

Test 2 (FIG. 12)

While the Test 1 Bad group appears to identify patients that have a very poor prognosis, and can be predicted to exhibit primary Immune resistance if later treated with anti-PD-1/anti-PD-L1 therapies, it is likely that this group contains patients that have a poor prognosis in general, whether they get immunotherapy or not. Test 2 addresses this by Identifying a smaller group of patients with very poor outcomes, which based on comparison with data from a chemotherapy-treated cohort, seem to have similarly poor outcomes on alternative therapy. Such patients are assigned the Bad class label in Test 2. In one embodiment, the test consists of classification by Classifier C. If a sample is classified as Group1 by Classifier C, it is given a final classification of "Bad". In another embodiment, Test 2 consists of a logical combination of outputs of Classifiers B, C and D, in a schema to also produce Intermediate and Good final class labels. If a sample is classified as Group1 by Classifier C, it Is given a final classification of "Bad". If it Is not classified as Bad by Classifier C, it is subject to classification by Classifiers B and D. If the classifications of the sample by Classifiers B and D are Group2, the final classification is set to "Good". Otherwise, the sample is given a final classification of "Intermediate". This combination schema is shown in FIG. 12. Patients classified as Good under Test 2 are also predicted to do particularly well on immune monotherapy.

In a configuration of Test 2 in the form of logical combination on Classifiers B, C and D as shown in FIG. 12, it assigned 24 (21%) samples of the development cohort to the Bad group, 60 (52%) to the "Intermediate" group and the remaining 32 (28%) samples were assigned to the "Good" group. As in one configuration of Test 1, in which Classifiers A, B and D are all used, Test 2 assigns samples one of three classifications Bad, Intermediate or Good, and for the development cohort the Test 2 Good group is Identical to the Test 1 Good group. The Bad group demonstrated very poor outcomes with median OS and PFS of 3.1 months and 1.4 months, respectively, with 79% of patients with a best response of PD.

The baseline clinical characteristics of Set A split by Test 2 classifications are listed in table 19. Kaplan-Meier plots of OS and PFS split by Test 2 classifications of Set A (and binary combinations of the classification labels) are shown in FIG. 13. Hazard ratios (HRs), Cox p values and log-rank p values obtained when comparing the time-to-event data between the classification groups and their binary combinations are shown in table 20 for OS and in table 21 for PFS. Hazard ratios (HRs) and Cox p values, adjusted for PS, smoking status, histology and PD-L1 status and obtained when comparing the time-to-event data (OS and PFS) between the Bad vs Not Bad binary combination are shown in table 22 and between the Not Good vs Good binary combination are shown in table 23. The OS and PFS medians are shown in table 24 for each of the classification groups and for their binary combinations.

TABLE 19

Baseline clinical characteristics of Set A split by Test 2 classifications

| | | Bad (N = 24) n (%) | Intermediate (N = 60) n (%) | Good (N = 32) n (%) | P value |
| --- | --- | --- | --- | --- | --- |
| Gender | Male | 14 (58) | 33 (55) | 19 (59) | 0.909 |
| | Female | 10 (42) | 27 (45) | 13 (41) | |
| Age | Median (Range) | 68 (52-83) | 64 (43-80) | 64 (49-82) | — |
| Response | CR | 0 (0) | 0 (0) | 1 (3) | 0.009 |
| | PR | 2 (8) | 6 (10) | 8 (25) | |
| | SD | 2 (8) | 10 (17) | 7 (22) | |
| | PD | 19 (79) | 37 (62) | 9 (28) | |
| | NA | 1 (4) | 7 (12) | 7 (22) | |
| Performance Status | 0 | 5 (21) | 16 (27) | 15 (47) | 0.011 |
| | 1 | 9 (38) | 37 (62) | 14 (44) | |
| | 2 | 6 (25) | 5 (8) | 1 (3) | |
| | 3 | 2 (8) | 1 (2) | 0 (0) | |
| | NA | 2 (8) | 1 (2) | 2 (6) | |
| Histology | Two primary tumors | 0 (0) | 2 (3) | 0 (0) | 0.731 |
| | Adenocarcinoma | 16 (67) | 36 (60) | 25 (78) | |
| | NSCLC-NEC | 0 (0) | 2 (3) | 1 (3) | |

TABLE 19-continued

Baseline clinical characteristics of Set A split by Test 2 classifications

|  |  | Bad (N = 24) n (%) | Intermediate (N = 60) n (%) | Good (N = 32) n (%) | P value |
|---|---|---|---|---|---|
|  | NSCLC-NOS | 1 (4) | 5 (8) | 2 (6) |  |
|  | Squamous | 7 (29) | 15 (25) | 4 (13) |  |
| Smoking Status | Current | 4 (17) | 12 (20) | 7 (22) | 0.725 |
|  | Former | 17 (71) | 44 (73) | 20 (63) |  |
|  | Never | 3 (13) | 3 (5) | 4 (13) |  |
|  | NA | 0 (0) | 1 (2) | 1 (3) |  |
| Brain Metastases at start of Itx | No | 18 (75) | 45 (75) | 24 (75) | >0.999 |
|  | Yes | 6 (25) | 15 (25) | 8 (25) |  |
| Previous Rtx | No | 8 (33) | 20 (33) | 15 (47) | 0.431 |
|  | Yes | 16 (67) | 40 (67) | 17 (53) |  |
| Previous Thoracic Rtx | No | 17 (71) | 37 (62) | 25 (78) | 0.281 |
|  | Yes | 7 (29) | 23 (38) | 7 (22) |  |
| VeriStrat classification † | Good | 3 (13) | 53 (88) | 32 (100) | <0.001 |
|  | Poor | 21 (88) | 7 (12) | 0 (0) |  |
| PD-L1 status | Positive (≥1%) | 5 (21) | 17 (28) | 10 (31) | 0.117 |
|  | Negative (<1%) | 9 (38) | 24 (40) | 5 (16) |  |
|  | NA | 10 (42) | 19 (32) | 17 (53) |  |

† VeriStrat Classifier applied to Deep MALDI average spectra

TABLE 20

Statistics for OS by Test 2 classification (of Set A) bad vs intermediate vs good and by combinations not bad vs bad and good vs not good

|  | CP HR (95% CI) | Cox p value | Log-rank p value |
|---|---|---|---|
| Intermediate vs Bad | 0.64 (0.37-1.11) | 0.114 | 0.112 |
| Good vs Intermediate | 0.50 (0.28-0.91) | 0.024 | 0.021 |
| Good vs Bad | 0.31 (0.16-0.62) | <0.001 | <0.001 |
| Not Bad vs Bad | 0.50 (0.29-0.84) | 0.009 | 0.008 |
| Good vs Not Good | 0.45 (0.25-0.79) | 0.006 | 0.004 |

TABLE 21

Statistics for PFS by Test 2 classification (of Set A) bad vs intermediate vs good and by combinations not bad vs bad and good vs not good

|  | CP HR (95% CI) | Cox p value | Log-rank p value |
|---|---|---|---|
| Intermediate vs Bad | 0.73 (0.44-1.22) | 0.230 | 0.235 |
| Good vs Intermediate | 0.49 (0.29-0.84) | 0.009 | 0.008 |
| Good vs Bad | 0.35 (0.18-0.66) | 0.001 | <0.001 |
| Not Bad vs Bad | 0.57 (0.35-0.93) | 0.024 | 0.024 |
| Good vs Not Good | 0.45 (0.27-0.76) | 0.003 | 0.002 |

TABLE 22

Multivariate statistics for OS and PFS by Test 2 Bad vs Not Bad binary combination of the classification groups (of Set A)

|  | OS | | PFS | |
|---|---|---|---|---|
|  | HR (95% CI) | p value | HR (95% CI) | p value |
| PIR Test2 (NotBad vs Bad) | 0.65 (0.34-1.22) | 0.179 | 0.64 (0.36-1.14) | 0.132 |
| ECOG PS (1 vs 0) | 1.69 (0.89-3.18) | 0.107 | 1.40 (0.81-2.41) | 0.224 |
| ECOG PS (≥2 vs 0) | 4.74 (2.05-10.95) | <0.001 | 2.65 (1.26-5.56) | 0.010 |
| Never vs ever smoker | 1.93 (0.85-4.38) | 0.117 | 1.20 (0.53-2.69) | 0.661 |
| Squamous vs Non-squamous | 1.05 (0.58-1.89) | 0.879 | 1.03 (0.61-1.76) | 0.908 |
| PD-L1 (<1% vs ≥1%) | 1.85 (0.96-3.58) | 0.068 | 1.60 (0.87-2.92) | 0.128 |
| PD-L1 (NA vs ≥1%) | 0.84 (0.42-1.68) | 0.617 | 0.85 (0.44-1.61) | 0.623 |

TABLE 23

Multivariate statistics for OS and PFS by Test 2 Not Good vs Good binary combination of the classification groups (of Set A)

|  | OS | | PFS | |
|---|---|---|---|---|
|  | HR (35% CI) | p value | HR (95% CI) | p value |
| PIR Test2 (Good vs NotGood) | 0.65 (0.32-1.29) | 0.216 | 0.65 (0.36-1.17) | 0.148 |
| ECOG PS (1 vs 0) | 1.63 (0.86-3.09) | 0.133 | 1.37 (0.80-2.36) | 0.257 |
| ECOG PS (≥2 vs 0) | 4.74 (2.08-10.80) | <0.001 | 2.54 (1.22-5.30) | 0.013 |
| Never vs ever smoker | 2.32 (1.00-5.37) | 0.051 | 1.43 (0.63-3.23) | 0.390 |
| Squamous vs Non-squamous | 1.04 (0.57-1.88) | 0.899 | 1.06 (0.63-1.79) | 0.831 |
| PD-L1 (<1% vs ≥1%) | 1.76 (0.91-3.42) | 0.095 | 1.63 (0.89-2.97) | 0.113 |
| PD-L1 (NA vs ≥1%) | 0.91 (0.46-1.80) | 0.777 | 0.96 (0.52-1.78) | 0.893 |

TABLE 24

Medians for OS and PFS by Test 2 classification (of Set A) bad vs intermediate vs good and by combinations not bad vs bad and good vs not good

|  | Number of samples | Median OS (95% CI) days | Median PFS (95% CI) days |
| --- | --- | --- | --- |
| Bad | 24 | 93 (54-240) | 43 (36-84) |
| Intermediate | 60 | 248 (152-338) | 76 (42-130) |
| Good | 32 | 528 (260-undefined) | 276 (75-undefined) |
| Not Bad | 92 | 316 (193-393) | 93 (69-182) |
| Not Good | 84 | 183 (130-280) | 55 (42-83) |

Kaplan-Meer plots of OS and PFS split by Test 2 classifications of Set A and Set C (whole set, docetaxel and pemetrexed arms) are shown in FIG. 14. Kaplan-Meier plots of OS and PFS split by binary combinations of Test 2 classifications of Set A and Set C (docetaxel arm) are shown in FIG. 15.

To assess the reproducibility of Test 2, the Classifiers were run on the average spectra obtained from two rounds of spectral acquisition of an external set of 98 samples. These pre-treatment samples were collected from Non-Small Cell Lung Cancer (NSCLC) patients receiving nivolumab. The classifications obtained for Round1 and Round2 are compared in table 25 for Test 2 three-way classifications, in table 26 for the binary combination Bad vs Not Bad, and in table 27 for the binary combination Not Good vs Good. Classification concordance is 87% for the three-way classifications, 94% for the Bad Not Bad combination and 93% for the Not Good/Good combination.

TABLE 25

Reproducibility of Test 2 (three way classifications)

|  |  | Round2 | | |
| --- | --- | --- | --- | --- |
|  |  | Bad (N = 20) | Intermediate (N = 47) | Good (N = 31) |
| Round1 | Bad (N = 20) | 17 | 3 | 0 |
|  | Intermediate (N = 42) | 3 | 38 | 1 |
|  | Good (N = 36) | 0 | 6 | 30 |

TABLE 26

Reproducibility of Test 2 (Bad vs Not Bad binary combination)

|  |  | Round2 | |
| --- | --- | --- | --- |
|  |  | Bad (N = 20) | Not Bad (N = 78) |
| Round1 | Bad (N = 20) | 17 | 3 |
|  | Not Bad (N = 78) | 3 | 75 |

TABLE 27

Reproducibility of Test 2 (Not Good vs Good binary combination)

|  |  | Round2 | |
| --- | --- | --- | --- |
|  |  | Not Good (N = 67) | Good (N = 31) |
| Round1 | Not Good (N = 62) | 61 | 1 |
|  | Good (N = 36) | 6 | 30 |

PSEA (as per our original approach referenced above in the discussion of Test 1) was used to look for an association of the classifications from Test 2 with biological processes. Of the 49 samples with paired deep MALDI and protein panel measurements, 10 (20%) classified as Bad, 22 (45%) as Intermediate and 17 (35%) as Good.

The results for the 29 different biological processes tested are shown in table 28 when looking at the biological association of the Bad vs Not Bad binary combination. P values are not corrected for multiple comparisons. At the $\alpha=0.05$ significance level, associations of the test classifications were found with complement.

TABLE 28

Results of Protein Set Enrichment Analysis for Test 2 binary combinations Bad vs Not Bad

| Biological Process | Enrichment score | P value |
| --- | --- | --- |
| Acute inflammation | 0.338 | 0.157 |
| Innate Immune Response | 0.523 | 0.299 |
| Adaptive immune response | 0.213 | 0.948 |
| Glycolytic Processes | −0.481 | 0.323 |
| Immune T-cells | −0.201 | 0.791 |
| Immune B-cells | 0.334 | 0.435 |
| Cell cycle | 0.162 | 0.982 |
| NK regulation | −0.288 | 0.744 |
| Complement | 0.493 | 0.044 |
| Cancer - experimental | 0.863 | 0.261 |
| Acute response | 0.515 | 0.139 |
| Cytokine activity | −0.310 | 0.251 |
| Wound healing | −0.239 | 0.641 |
| Interferon | 0.196 | 0.870 |
| Interleukin-10 | 0.235 | 0.350 |
| GFR* signaling | −0.255 | 0.187 |
| Immune response | 0.247 | 0.193 |
| Immune Response Type 1 | −0.324 | 0.792 |
| Immune Response Type 2 | 0.587 | 0.317 |
| Immune Response - Complement | 0.180 | 0.807 |
| Immune Response - Complement - Acute | −0.157 | 0.964 |
| Acute phase | 0.442 | 0.148 |
| Hypoxia | −0.311 | 0.309 |
| Cancer | 0.151 | 0.967 |
| Cell adhesion | −0.228 | 0.479 |
| Mesenchymal transition | 0.321 | 0.719 |
| Extracellular matrix - restricted source, UNIPROT | −0.315 | 0.450 |
| Extracellular matrix - from different sources | −0.241 | 0.613 |
| Angiogenesis | −0.289 | 0.207 |

*GFR = growth factor receptor

The results obtained when looking at biological associations of the Not Good vs Good binary combination are shown in table 29. P values are not corrected for multiple comparisons. At the $\alpha=0.05$ significance level, associations of the Not Good vs Good binary labels were found with innate immune response, acute response and acute phase. In addition, at the $\alpha=0.10$ significance level, associations were found with acute Inflammation and wound healing.

TABLE 29

Results of Protein Set Enrichment Analysis for Test 2 binary combinations Not Good vs Good

| Biological process | Enrichment score | p value |
| --- | --- | --- |
| Acute inflammation | 0.370 | 0.079 |
| Innate Immune Response | 0.674 | 0.042 |
| Adaptive immune response | 0.379 | 0.409 |

TABLE 29-continued

Results of Protein Set Enrichment Analysis for
Test 2 binary combinations Not Good vs Good

| Biological process | Enrichment score | p value |
|---|---|---|
| Glycolytic Process | −0.380 | 0.630 |
| Immune T-cells | −0.296 | 0.218 |
| Immune B-cells | 0.228 | 0.866 |
| Cell cycle | 0.197 | 0.870 |
| NK regulation | −0.481 | 0.217 |
| Complement | 0.411 | 0.161 |
| Cancer - experimental | 0.894 | 0.188 |
| Acute response | 0.604 | 0.031 |
| Cytokine activity | −0.257 | 0.523 |
| Wound healing | −0.386 | 0.082 |
| Interferon | 0.149 | 0.990 |
| Interleukin-10 | 0.233 | 0.366 |
| GFR* signaling | −0.235 | 0.324 |
| Immune response | 0.255 | 0.146 |
| Immune Response Type 1 | 0.194 | 0.996 |
| Immune Response Type 2 | 0.477 | 0.565 |
| Immune Response - Complement | −0.191 | 0.693 |
| Immune Response - Complement - Acute | −0.243 | 0.234 |
| Acute phase | 0.552 | 0.018 |
| Hypoxia | 0.214 | 0.821 |
| Cancer | 0.198 | 0.484 |
| Cell adhesion | −0.285 | 0.165 |
| Mesenchymal transition | −0.286 | 0.841 |
| Extracellular matrix - restricted source, UNIPROT | −0.369 | 0.270 |
| Extracellular matrix - from different sources | −0.273 | 0.439 |
| Angiogenesis | −0.197 | 0.833 |

*GFR = growth factor receptor

In summary, the presented tests provide a potential tool to inform on the likelihood of immune therapy benefit, with special emphasis on primary resistance. In its Bad group Test 1, the PIR test, Identifies a group of patients that obtains little benefit from anti-PD1/PD-L1 therapies over chemotherapy. Test 2 identifies a group of patients that appears to have poor outcomes regardless of therapy, indicated by the Bad final class label. In a configuration of Tests 1 and 2 which produce Intermediate and Good class labels as shown in the Test 1 and Test 2 schema figures, the Good group of Test 1 and Test 2 demonstrates excellent outcomes, indicating that these patients are likely to do well on immune checkpoint inhibition, e.g., nivolumab monotherapy.

Test 3

The Test 2 "Bad" group has an outcome roughly as poor as for treatment with docetaxel as for immunotherapy, as observed in FIG. 15A-15D. The patients classified in this group seem to have poor outcomes no matter which of the two treatments they receive. On the other hand, the Test 1 "Bad" group seems to have better outcome for treatment with docetaxel when compared with immunotherapy, as observed in FIG. 11A-11D. It is reasonable to hypothesize that the group of patients that are classified as Bad by Test 1 but not as Bad by Test 2 corresponds to the subset of patients that is resistant to immunotherapies and would rather benefit from alternative chemotherapies, e. g. docetaxel and pemetrexed. Test 3 was designed to identify this subset of patients.

If a sample is classified as Bad by Test 1 and as Intermediate or Good (i.e., "Not Bad") by Test 2, it is given a final classification of "Resistant". All other samples get the final classification of "Non-resistant". This combination scheme is shown in FIG. 18.

Figure 17A:
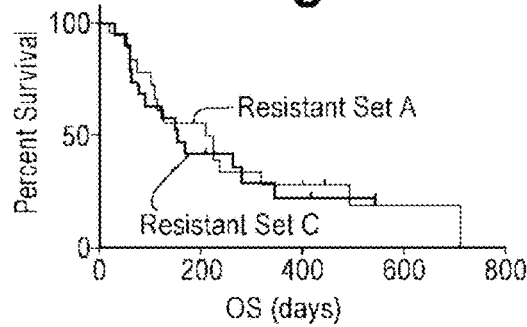
FIGS. 17A-17F: Kaplan-Meier plots of OS and PFS for set A and set C (whole set, docetaxel and pemetrexed arms) for samples classified as Bad (Resistant) by Test 3.
Figure 17B:
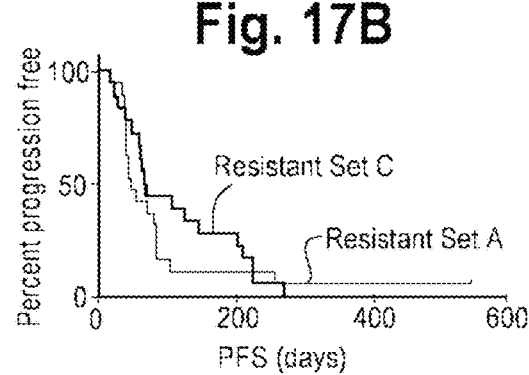
Figure 17C:
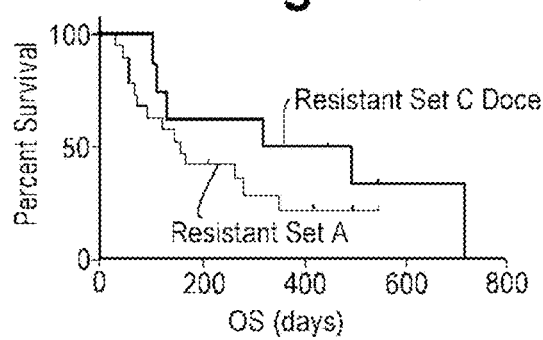
Figure 17D:
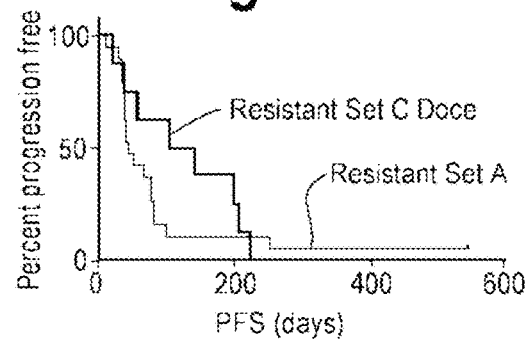
Figure 17E:
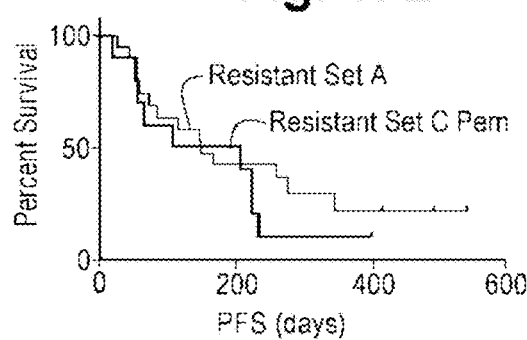
Figure 17F:
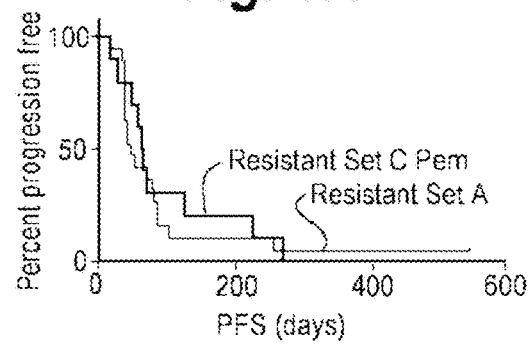

Nineteen (16%) samples of Set A were assigned to the "Resistant" group and the remaining 97 (84%) samples were assigned to the "Non-resistant" (also referred to as "Sensitive") group. The baseline clinical characteristics of Set A split by Test 3 classifications are listed in table 30. Kaplan-Meier plots of OS and PFS are shown for set A and set C (whole set, docetaxel and pemetrexed arms) In FIG. 17A-F for samples classified as Resistant by Test 3. Note the similar survival curves in FIGS. 17A and 17B and the numerically inferior outcomes in FIGS. 17C and 17D for the patients classified as Resistant in Set A (development—treated with nivolumab) compared with Set C (treated with chemotherapy (docetaxel or pemetrexed) or treated with docetaxel, respectively). The OS and PFS medians are shown in table 31 for each of the sample subsets.

TABLE 30

Baseline clinical characteristics of
Set A split by Test 3 classifications

| | | Non-Resistant (N = 97) n (%) | Resistant (N = 19) n (%) | P value |
|---|---|---|---|---|
| Gender | Male | 54 (56) | 12 (63) | 0.619 |
| | Female | 43 (44) | 7 (37) | |
| Age | Median (Range) | 64 (43-83) | 65 (52-79) | — |
| Response | CR | 1 (1) | 0 (0) | 0.010 |
| | PR | 14 (14) | 2 (11) | |
| | SD | 19 (20) | 0 (0) | |
| | PD | 48 (49) | 17 (89) | |
| | NA | 15 (15) | 0 (0) | |
| Performance Status | 0 | 32 (33) | 4 (21) | 0.634 |
| | 1 | 47 (48) | 13 (68) | |
| | 2 | 10 (10) | 2 (11) | |
| | 3 | 3 (3) | 0 (0) | |
| | NA | 5 (5) | 0 (0) | |
| Histology | Two primary tumors | 1 (1) | 1 (5) | 0.228 |
| | Adenocarcinoma | 67 (69) | 10 (53) | |
| | NSCLC-NEC | 3 (3) | 0 (0) | |
| | NSCLC-NOS | 7 (7) | 1 (5) | |
| | Squamous | 19 (20) | 7 (37) | |
| Smoking Status | Current | 16 (16) | 7 (37) | 0.090 |
| | Former | 71 (73) | 10 (53) | |
| | Never | 9 (9) | 1 (5) | |
| | NA | 1 (1) | 1 (5) | |
| Brain Metastases at start of Itx | No | 73 (75) | 14 (74) | >0.999 |
| | Yes | 24 (25) | 5 (26) | |
| Previous Rtx | No | 38 (39) | 5 (26) | 0.436 |
| | Yes | 59 (61) | 14 (74) | |
| Previous Thoracic Rtx | No | 65 (67) | 14 (74) | 0.788 |
| | Yes | 32 (33) | 5 (26) | |
| VeriStrat classification † | Good | 74 (76) | 14 (74) | 0.776 |
| | Poor | 23 (24) | 5 (26) | |
| PD-L1 status | Positive (≥1%) | 27 (28) | 5 (26) | 0.630 |
| | Negative (<1%) | 30 (31) | 8 (42) | |
| | NA | 40 (41) | 6 (32) | |

† VeriStrat classifier applied to Deep MALDI average spectra

TABLE 31

Medians for OS and PFS for samples from Set A and Set C (whole set, docetaxel and pemetrexed arms) classified as Resistant by Test 3

| | Number of samples | Median OS (95% CI) days | Median PFS (95% CI) days |
|---|---|---|---|
| Set A | 19 | 152 (60-345) | 45 (39-81) |
| Set C (whole set) | 18 | 216 (99-316) | 66 (46-144) |
| Set C (docetaxel arm) | 8 | 405 (99-713) | 125 (22-209) |
| Set C (pemetrexed arm) | 10 | 159 (19-225) | 62 (15-123) |

Reproducibility

To assess the reproducibility of Test 3, the classifier was run on the average spectra obtained from two rounds of spectral acquisition of an external set of 98 samples. These pre-treatment samples were collected from Non-Small Cell Lung Cancer (NSCLC) patients receiving nivolumab. The classifications obtained for Round1 and Round2 are compared in table 32. Classification concordance is 89%.

TABLE 32

Reproducibility of Test 3

|  |  | Round2 | |
| --- | --- | --- | --- |
|  |  | Non-Resistant (N = 79) | Resistant (N = 19) |
| Round1 | Non-Resistant (N = 78) | 73 | 5 |
|  | Resistant (N = 20) | 6 | 14 |

Relation to Protein Functional Groups

PSEA (as per our original approach) was used to look for an association of the classifications from Test 3 with biological processes. Of the 49 samples with paired deep MALDI and protein panel measurements, 37 (76%) classified as Non-resistant and 12 (24%) as Resistant. For the subset of 39 samples that were not classified as Bad by Test 2, 27 (69%) classified as Non-resistant and 12 (31%) as Resistant.

The results for the 29 different biological processes tested are shown in table 33 when looking at the biological association of Test 3 classification. Only the 39 samples that were not classified as Bad by Test 2 were used in the analysis. P values are not corrected for multiple comparisons. At the $\alpha=0.05$ significance level, associations of the test classifications were found with complement, wound healing, immune response—complement—acute, acute phase and extracellular matrix. In addition, at the $\alpha=0.10$ significance level, associations of the test classifications were found with acute inflammation, acute response and interleukin-10.

TABLE 33

Results of Protein Set Enrichment Analysis for Test 3 classifications

| Biological process | Enrichment score | p value |
| --- | --- | --- |
| Acute inflammation | 0.379 | 0.057 |
| Innate Immune Response | 0.399 | 0.583 |
| Adaptive immune response | −0.256 | 0.847 |
| Glycolytic Process | 0.317 | 0.831 |
| Immune T-cells | −0.261 | 0.363 |
| Immune B-cells | −0.171 | 0.982 |
| Cell cycle | −0.188 | 0.912 |
| NK regulation | −0.432 | 0.362 |
| Complement | 0.544 | 0.011 |
| Cancer - experimental | −0.641 | 0.725 |
| Acute response | 0.546 | 0.065 |
| Cytokine activity | −0.189 | 0.888 |
| Wound healing | −0.476 | 0.010 |
| Interferon | −0.280 | 0.330 |
| Interleukin-10 | 0.288 | 0.071 |
| GFR* signaling | −0.187 | 0.796 |
| Immune response | 0.244 | 0.172 |
| Immune Response Type 1 | 0.450 | 0.411 |
| Immune Response Type 2 | 0.436 | 0.631 |
| Immune Response - Complement | −0.245 | 0.201 |
| Immune Response - Complement - Acute | −0.297 | 0.042 |
| Acute phase | 0.569 | 0.009 |
| Hypoxia | 0.264 | 0.571 |
| Cancer | 0.187 | 0.619 |
| Cell adhesion | −0.259 | 0.270 |
| Mesenchymal transition | 0.194 | 0.993 |
| Extracellular matrix - restricted source, UNIPROT | −0.567 | 0.008 |
| Extracellular matrix - from different sources | −0.425 | 0.031 |
| Angiogenesis | −0.202 | 0.805 |

*GFR = growth factor receptor

Discussion

Test 3 assigned samples classified as Bad by Test 1 and Not Bad by Test 2 as "resistant", with the hypothesis that, while patients classified as Bad by Test 2 may have very poor outcomes under all therapies, the poor prognosis of "Resistant" patients labelled in accordance with Test 3 may be induced by checkpoint inhibition, and these patients may have better outcomes with alternative therapies, such as docetaxel, or newer chemotherapy regimens, such as docetaxel plus ramucirumab, than on an anti-PD-1 agent. The percentage of patients classified by Test 3 as Resistant is 16% in the development set, which is in line with the numbers suggested in clinical studies of the hyperprogression or early death phenomenon. Resistant patients showed poor outcomes on nivolumab, with median OS and PFS of 5.0 months and 1.5 months, respectively and 89% of patients had PD as their best response to therapy.

In summary, the presented tests provide a potential tool to inform on the likelihood of immune therapy benefit, with special emphasis on primary resistance. In its Bad group Test 1, the PIR test, identifies a group of patients that, compared to chemotherapy, obtains little benefit. Test 2 identifies a group of patients that appears to have poor outcomes regardless of therapy. Test 3 Identifies a group of patients where checkpoint inhibition might potentially be detrimental, and if the patient sample is assigned the "resistant" label in Test 3 the patient is guided towards alternative therapies to anti-PD-1 agents, such as docetaxel, or newer chemotherapy regimens, such as docetaxel plus ramucirumab. The Good group of Test 1 and Test 2 demonstrates excellent outcomes, indicating that these patients are likely to do well on checkpoint inhibition.

Laboratory Test Center

The practical tests of this disclosure will be implemented typically in a laboratory test center configured with a mass spectrometer (e.g., MALDI-TOF) configured to conduct mass spectrometry on a blood-based sample obtained from the cancer patient. The mass spectrometer is configured to obtain a mass spectrum in the form of a set of integrated intensity values for a multitude of features in the mass spectrum, for example the features of Appendix A and Appendix B. A fulsome description of a laboratory test center and the manner of conducting a test on a blood-based sample Is described in Example 5 and FIG. 15 of our prior U.S. Pat. No. 10,007,766, the description of which is incorporated by reference.

The laboratory test center includes a computer including a processing unit and a nontransitory computer memory storing instructions and classification parameters for one or more of the Classifiers of this disclosure (A, B, C and D) for execution by the processing unit.

For Test 1, a memory stores parameters for at least Classifiers A and D. The parameters for Classifier A take the form of:
 a) a reference set of integrated intensity mass spectral feature values for a set of mass spectral features associated with immune response type 2, the feature values obtained by conducting mass spectrometry on a development set of blood-based samples obtained from a population of non-small cell lung cancer patients treated with an anti-PD-1 drug (see the description of the set of mass spectral features values for the samples of set A used to develop Classifier A); and
 b) parameters defining a classification procedure for generating a class label for the mass spectrum of the blood-based sample of the cancer patient by comparing the integrated intensity values of features associated with immune response type 2 in the mass spectrum of the blood-based sample of the cancer patient with the reference set of Classifier A. For example the classification procedure could take the form of a combination or ensemble of master Classifiers generated in accordance with the procedure of FIG. 5.

The parameters for Classifier D take the form of:
 a) a reference set of integrated intensity mass spectral feature values for a set of mass spectral features, the feature values obtained by conducting mass spectrometry on a development set of blood-based samples obtained from a population of melanoma patients treated with an anti-PD-1 drug (see the description of Set B used to develop Classifier D); and
 b) parameters defining a classification procedure for generating a class label for the mass spectrum of the blood-based sample of the cancer patient by comparing the integrated intensity values of features in the mass spectrum of the blood-based sample of the cancer patient with the reference set of Classifier D. For example the classification procedure could take the form of a combination or ensemble of master Classifiers generated in accordance with the procedure of FIG. 5.

For example, the Classifier procedure includes code implementing a kNN classification algorithm (which is implemented in the mini-Classifiers as explained above), including the features and depth of the kNN algorithm (parameters) and identification of all the mini-Classifiers passing filtering, program code for executing the final Classifier generated in accordance with FIG. 5 on the mass spectrum of a patient sample, including logistic regression weights and data representing master Classifier(s) forming the final Classifier, including probability cutoff parameter, mini-Classifier parameters for each mini-Classifier that passed filtering, etc., and a data structure for storing classification results, including a final class label for the test sample.

For Test 2, a memory stores instructions and classification parameters for at least a first classifier (Classifier C), for execution by the processing unit. Classifier C is defined by:
 a) a reference set of integrated intensity mass spectral feature values for a set of mass spectral features, the feature values obtained by conducting mass spectrometry on a development set of blood-based samples obtained from a population of non-small-cell lung cancer patients treated with an anti-PD1 drug; and
 b) parameters defining a classification procedure for generating a class label for the mass spectrum of the blood-based sample of the cancer patient by comparing the integrated Intensity values of features in the mass spectrum of the blood-based sample of the cancer patient with the reference set of Classifier C.

If the class label generated by Classifier C is "Group1" or the equivalent indicating poor overall survival or progression free survival the patient Is predicted to have a poor prognosis in response to treatment by either the immunotherapy drug or the alternative chemotherapy.

The reader will note that Classifier C (in Test 2) differs from Classifier A (in Test 1) in that in Classifier A the reference set is limited to mass spectral feature values which are associated with immune response type 2 (see Appendix B) whereas in Classifier C there is no such limitation, for example all 274 features listed in Appendix A are used. Also, there are differences in the reference subsets of patients that were used in classifier development, as explained above in the description of Classifiers A and C.

For Test 3, the laboratory testing apparatus is provided for predicting primary immune resistance to immunotherapy drugs for a cancer patient. The apparatus includes a mass spectrometer configured to conduct mass spectrometry on a blood-based sample obtained from the cancer patient and obtaining a mass spectrum in the form of a set of integrated intensity values for a multitude of features in the mass spectrum, a processing unit, and a nontransitory computer memory storing instructions and classification parameters for performing two mass spectrometry classification tests on the mass spectrum. Such tests take the form of:
 a) a first test assigning a class label indicating whether the patient is likely to exhibit primary immune resistance if treated with an immunotherapy drug (class label "Bad" or the equivalent (i.e., Test 1) and
 2) a second test assigning a class label indicating whether a patient is likely to have poor outcomes on both Immunotherapy and alternative chemotherapies (class label "Bad" or the equivalent, i.e., Test 2)
  wherein if the mass spectrum is assigned the Bad class label by the first test but is not assigned a "Bad" class label by the second test (e.g., either Intermediate or Good), the mass spectrum is assigned a "resistant" class label or the equivalent, wherein the resistant class label indicates that that patient is likely to be resistant to immunotherapy drugs and may have better outcomes when treated with alternative chemotherapies.

In one embodiment the first test takes the form of classification by at least a first classifier and a second classifier (Classifiers A and D, respectively), for execution by the processing unit,
 wherein Classifier A is defined by:
 a) a reference set of integrated intensity mass spectral feature values for a set of mass spectral features associated with immune response type 2, the feature values obtained by conducting mass spectrometry on a development set of blood-based samples obtained from a population of non-small cell lung cancer patients treated with an anti-PD1 drug; and
 b) parameters defining a classification procedure for generating a class label for the mass spectrum of the blood-based sample of the cancer patient by comparing the integrated intensity values of features associated with immune response type 2 in the mass spectrum of the blood-based sample of the cancer patient with the reference set of Classifier A;
 wherein Classifier D is defined by:
 a) a reference set of integrated intensity mass spectral feature values for a set of mass spectral features, the feature values obtained by conducting mass spectrometry on a development set of blood-based samples obtained from a population of melanoma patients treated with an anti-PD1 drug; and b) parameters defining a classification procedure for generating a class label for the mass spectrum of the blood-based sample of the cancer patient by comparing the integrated intensity values of features in the mass spectrum of the blood-based sample of the cancer patient with the reference set of Classifier D;

wherein if both Classifier A and Classifier D produce a "Group1" or the equivalent indicating primary immune resistance the mass spectrum is assigned the Bad class label in Test 1.

In one embodiment, the second test comprises classification of the mass spectrum by at least a first classifier (Classifier C), for execution by the processing unit, wherein Classifier C is defined by:

a) a reference set of integrated intensity mass spectral feature values for a set of mass spectral features, the feature values obtained by conducting mass spectrometry on a development set of blood-based samples obtained from a population of non-small-cell lung cancer patients treated with an anti-PD-1 drug; and b) parameters defining a classification procedure for generating a class label for the mass spectrum of the blood-based sample of the cancer patient by comparing the integrated intensity values of features in the mass spectrum of the blood-based sample of the cancer patient with the reference set of Classifier C;

wherein if the class label generated by Classifier C comprises "Group1" or the equivalent indicating poor overall survival or progression free survival the patient is predicted to have a poor prognosis in response to treatment by either the immunotherapy drug or the alternative chemotherapy, class label "Bad", otherwise a class label other than "Bad" is assigned to the mass spectrum.

In still another aspect, a method is disclosed of guiding treatment of a cancer patient towards chemotherapies that are alternatives to immunotherapy, comprising the steps of:

a) conducting mass spectrometry on a blood-based sample of the cancer patient and obtaining a mass spectrum;

b) conducting, in a programmed computer, mass spectrometry Tests 1 and 2 on the mass spectrum, wherein if Test 1 produces a "Bad" class label or the equivalent and Test 2 does not produce a "Bad" class label or the equivalent, the patient is assigned a "Resistant" class label guiding the patient towards chemotherapies which are alternatives to immunotherapy, and wherein Test 1 comprises classification of the mass spectrum by at least two classifiers (A and D) each having their own reference set of mass spectral feature values and developed from different sample sets and wherein Test 2 comprises classification by at least a third classifier (classifier C).

Validation Results

VW obtained two validation sample sets (V1 and V2) and performed validation of our Test 1 on these sample sets, as will be described in this section.

Validation Set 1, V1 (N=98): consisted of serum samples obtained from 58 2nd line, 31 3rd line, 8 4th line and 1 5th line NSCLC patients treated at Netherlands Cancer Institute (NKI, Amsterdam, NL) with nivolumab.

Validation Set 2, V2 (N=75): consisted of serum samples obtained from 2nd line NSCLC patients treated at Erasmus Medical Center (Rotterdam, NL) with nivolumab. Note that V2 has only patients treated in second line with the PD-1 checkpoint inhibitor, while V1 has 58 patients treated in second line and an additional 40 treated in higher line.

The clinical data for the patient cohorts are shown in the Table 34 below, with S the original classifier development cohort, V1 and V2 the validation cohorts, and D the subset of 68 patients in Set C treated with docetaxel.

TABLE 34

|  |  | S (N = 116) | V1 $2^{nd}$ line (N = 58) | V1 $3^{rd}$ + line (N = 40) | V2 (N = 75) | D (N = 68) |
| --- | --- | --- | --- | --- | --- | --- |
| Age | Median | 65 | 63 | 65 | 65 | 64 |
|  | (Range) | (43-83) | (29-75) | (46-77) | (35-78) | (39-77) |
| *% of available data |  | n (%*) | n (%*) | n (%*) | n (%*) | n (%*) |
| Gender | Male | 66 (57) | 31 (53) | 20 (50) | 48 (64) | 52 (76) |
|  | Female | 50 (43) | 27 (47) | 20 (50) | 27 (36) | 16 (24) |
| PS | 0 | 36 (32) | 15 (26) | 5 (13) | 18 (32) | 35 (51) |
|  | 1 | 60 (54) | 38 (66) | 27 (68) | 37 (66) | 29 (43) |
|  | 2+ | 15 (14) | 5 (9) | 8 (20) | 1 (2) | 4 (6) |
| Smoking Status | Ever | 104 (91) | 55 (95) | 33 (87) | 61 (92) | 64 (94) |
|  | Never | 10 (9) | 3 (5) | 5 (13) | 5 (8) | 4 (6) |
| Histology | Adenocarcinoma | 77 (66) | 27 (75) | 15 (71) | 49 (65) | 47 (75) |
|  | Squamous | 26 (22) | 6 (17) | 4 (19) | 17 (23) | 12 (19) |
|  | Other | 13 (11) | 3 (8) | 2 (10) | 9 (12) | 4 (6) |
| Response | CR | 1 (1) | 0 (0) | 1 (3) | 0 (0) | 0 (0) |
|  | PR | 16 (14) | 16 (28) | 12 (30) | 15 (20) | 7 (10) |
|  | SD | 19 (16) | 19 (33) | 7 (18) | 25 (33) | 23 (34) |
|  | PD | 65 (56) | 19 (33) | 18 (45) | 31 (41) | 22 (32) |
|  | NA/NE | 15 (13) | 4 (7) | 2 (5) | 4 (5) | 16 (24) |
| PFS (months) | Median | 2.6 | 5.2 | 2.6 | 4.3 | 3.5 |
| OS (months) | Median | 8.5 | 11.3 | 6.2 | 12.0 | 8.0 |

Figure 18A:
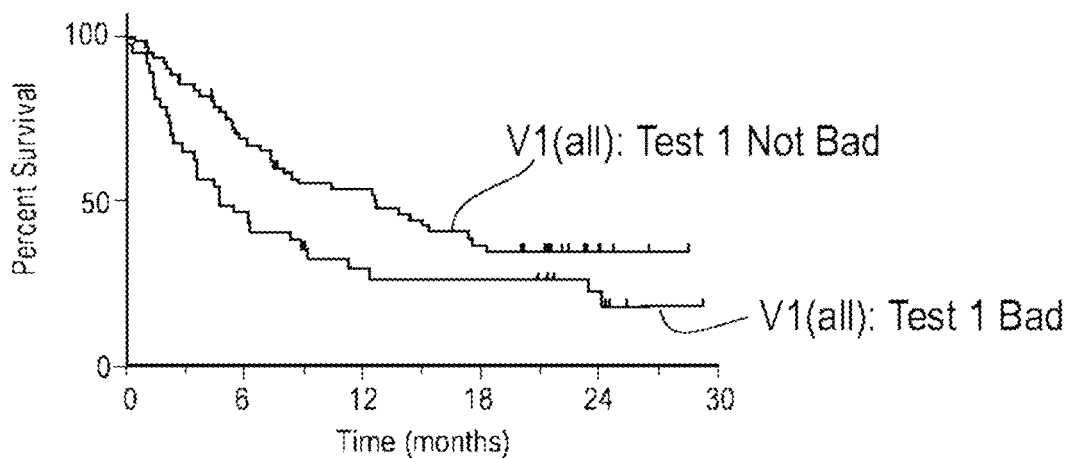
FIGS. 18A-18C: Kaplan-Meier plots of survival by class label Bad or Not Bad (Intermediate+Good class labels) for the Validation Set V1 for all patients (FIG. 18A), second line patients (FIG. 18B) and $3^{rd}$ and above line patients (FIG. 18C), after testing by Test 1.
Figure 18B:
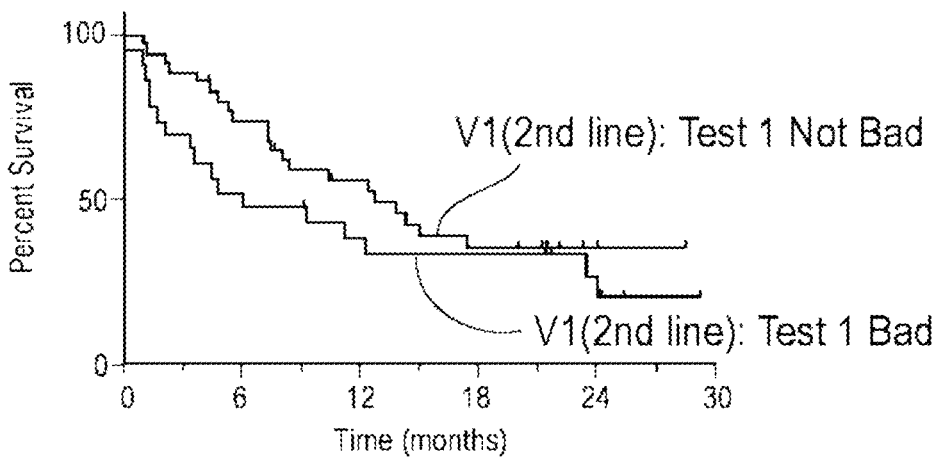
Figure 18C:
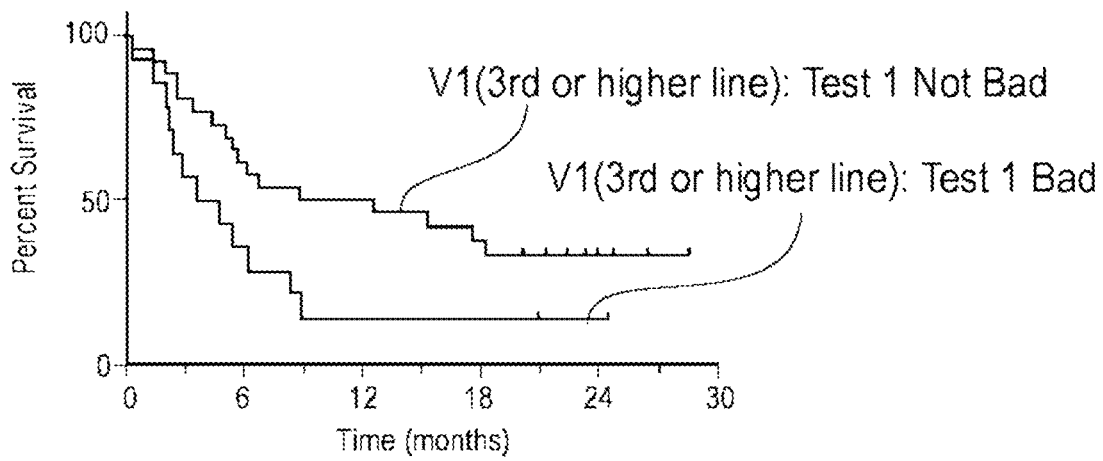
Figure 19:
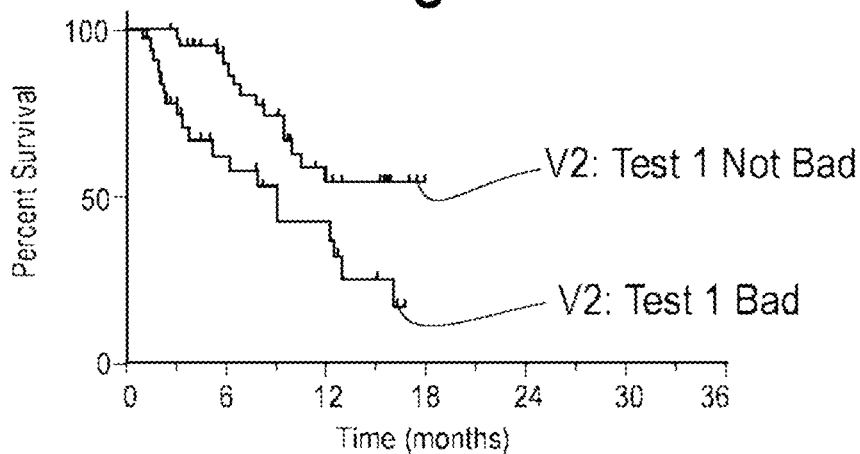
FIG. 19: Kaplan-Meier plots of survival by class label Bad or Not Bad (Intermediate+Good class labels) for the Validation Set V2 after testing by Test 1.

Validation sets V1 and V2 were subject to mass spectrometry and spectral data processing as explained above; the same procedures used to obtain mass spectral data for classifier development were used to obtain mass spectral data for these validation sample sets. The mass spectral data from these sample sets was then subject to classification in accordance with Test 1. The results for V1 are shown as Kaplan-Meier plots in FIGS. 18A-18C along with the classification statistics. FIG. 18A shows the plots for all patients in the V1 validation cohort; FIG. 18B shows the plots for just the second line patients, and FIG. 18C shows the plots for the third and above line patients. The results for set V2 are shown as Kaplan-Meier plots in FIG. 19. In these plots of FIGS. 18A-18C and 19, "Test 1 Not Bad" again refers to the combined Intermediate and Good final classification results produced by the Test 1 schema in accordance with FIG. 8.

Figure 20:
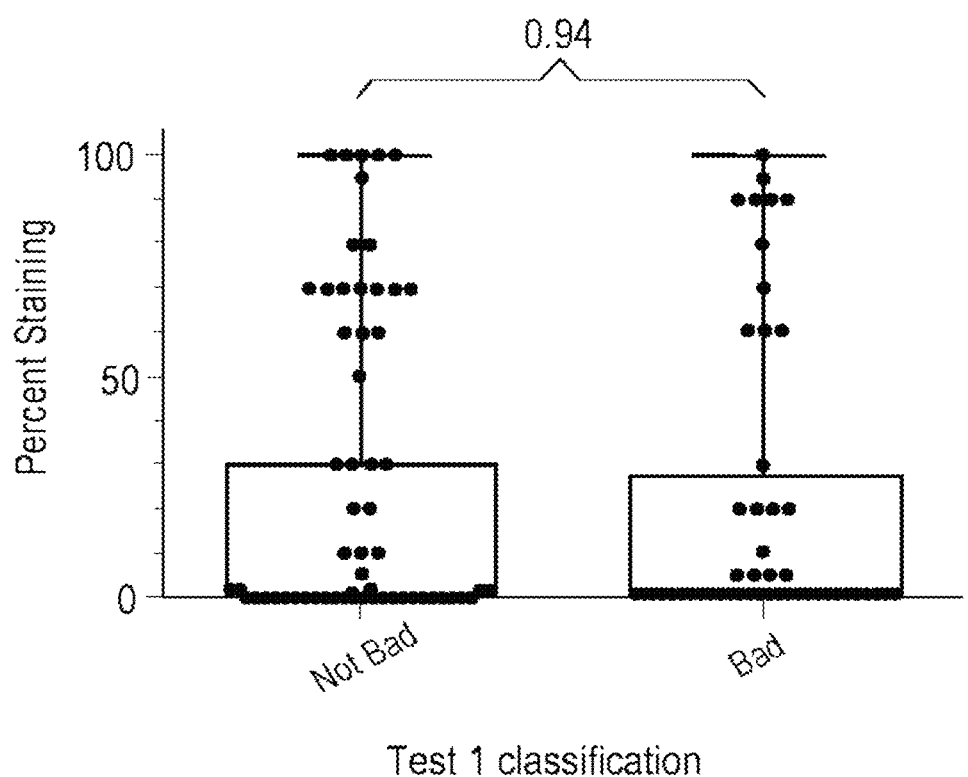
FIG. 20: box plot showing no association of Bad and Not Bad groups in the validation set with PD-L1 status.

As shown in the box plot of FIG. 20 and the Table 35 below the test classifications show no association with PD-L1 status:

TABLE 35

Test classifications for V1 + V2 show no association with PD-L1 status

|  | Test 1 Bad (N = 34) | Test 1 Not Bad (N = 63) |
|---|---|---|
| PD-L1 <1% | 20 (59%) | 38 (60%) |
| PD-L1 ≥1% | 14 (41%) | 25 (40%) |

Given the additional validations sets and PD-1 status, we have done a pooled multivariate analysis of the 3 cohorts (development and two validation, with validation restricted to 2nd line patients only). This takes advantage of the increased number of samples that we have in total (N=116+58+75). This analysis can be performed either stratified by cohort (which allows for a different baseline hazard in the Cox analysis for each cohort) or unstratified. The stratified analysis is likely to be most reliable and so is presented here in Table 36.

TABLE 36

Pooled analysis of all second line patients, stratified by cohort:

|  |  | HR (95% CI) | P value |
|---|---|---|---|
| OS: | | | |
| Test 1 (vs Bad) | NotBad | 0.53 (0.38-0.75) | <0.001 |
| Histology (vs adeno) | squamous | 0.83 (0.54-1.29) | 0.413 |
|  | NA/other | 1.10 (0.66-1.83) | 0.727 |
| Age (vs >=65) | <65 | 1.17 (0.82-1.66) | 0.394 |
| Gender (vs male) | female | 0.51 (0.35-0.75) | 0.001 |
| PS (vs 0) | 1 | 1.57 (1.03-2.41) | 0.037 |
|  | 2+ | 3.66 (2.00-6.68) | <0.001 |
|  | NA | 2.28 (1.15-4.53) | 0.019 |
| Smoking (vs Ever) | never | 1.88 (0.97-3.65) | 0.061 |
|  | NA | 0.75 (0.30-1.90) | 0.544 |
| PD-L1 (vs Positive) | negative | 1.23 (0.75-2.02) | 0.407 |
|  | NA | 0.84 (0.53-1.35) | 0.478 |
| PFS: | | | |
| Test 1 (vs Bad) | NotBad | 0.65 (0.48-0.90) | 0.008 |
| Histology (vs adeno) | squamous | 1.10 (0.75-1.61) | 0.626 |
|  | NA/other | 1.08 (0.69-1.68) | 0.744 |
| Age (vs >=65) | <65 | 1.30 (0.95-1.77) | 0.101 |
| Gender (vs male) | female | 0.68 (0.49-0.94) | 0.021 |
| PS (vs 0) | 1 | 1.38 (0.96-1.98) | 0.078 |
|  | 2+ | 2.24 (1.27-3.97) | 0.005 |
|  | NA | 1.90 (1.05-3.46) | 0.035 |
| Smoking (vs Ever) | never | 1.52 (0.84-2.77) | 0.165 |
|  | NA | 0.75 (0.33-1.75) | 0.510 |
| PD-L1 (vs Positive) | negative | 1.30 (0.83-2.04) | 0.246 |
|  | NA | 0.84 (0.56-1.26) | 0.393 |

This pooled analysis is consistent with the multivariate analysis of the development set. However, with its increased sample size, it allows us to demonstrate that Test1 classification Not Bad vs Bad is a statistically significant predictor of both OS and PFS when adjusted for performance status, smoking history, histology, age, gender, and PD-L1 status. Hence it adds additional, complementary information to these prognostic patient characteristics that are available to physicians.

To look more closely at any association between test classification and PD-L1 status, we have pooled the data from all 3 cohorts as well. The results are shown in the tables below for Test1 classifications only. The tables 37-39 include all patients and the tables 40-42 include only second line patients.

TABLE 37

|  | Bad | Intermediate | Good |
|---|---|---|---|
| PDL1 Positive (≥1%) | 22 | 21 | 15 |
| PDL1 Negative (<1%) | 28 | 30 | 16 |
| NA | 60 | 41 | 56 |

$\chi^2$ p = 0.114 (including NA),
$\chi^2$ p = 0.816 (excluding NA)

TABLE 38

|  | Bad | NotBad |
|---|---|---|
| PDL1 Positive (≥1%) | 22 | 36 |
| PDL1 Negative (<1%) | 28 | 46 |
| NA | 60 | 97 |

$\chi^2$ p = 0.998 (including NA),
$\chi^2$ p = 0.991 (excluding NA)

TABLE 39

|  | NotGood | Good |
|---|---|---|
| PDL1 Positive (≥1%) | 43 | 15 |
| PDL1 Negative (<1%) | 58 | 16 |
| NA | 101 | 56 |

$\chi^2$ p = 0.069 (including NA),
$\chi^2$ p = 0.568 (excluding NA)

Second Line Only:

TABLE 40

|  | Bad | Int | Good |
|---|---|---|---|
| PDL1 Positive (≥1%) | 21 | 19 | 14 |
| PDL1 Negative (<1%) | 25 | 26 | 12 |
| NA | 50 | 35 | 47 |

$\chi^2$ p = 0.117 (including NA),
$\chi^2$ p = 0.637 (excluding NA)

TABLE 41

|  | Bad | NotBad |
|---|---|---|
| PDL1 Positive (≥1%) | 21 | 33 |
| PDL1 Negative (<1%) | 25 | 38 |
| NA | 50 | 82 |

$\chi^2$ p = 0.970 (incl. NA);
$\chi^2$ p = 0.930 (excluding NA)

TABLE 42

|  | NotGood | Good |
|---|---|---|
| PDL1 Positive (≥1%) | 40 | 14 |
| PDL1 Negative (<1%) | 51 | 12 |
| NA | 85 | 47 |

$\chi^2$ p = 0.049 (including NA);
$\chi^2$ p = 0.372 (excluding NA)

The appended claims are offered by way of further descriptions of the disclosed inventions.

TABLE 43

Appendix A: List of feature definitions
The features marked with an asterisk * were removed from the final feature table, and used only for batch correction.

| Left M/Z | Center M/Z | Right M/Z |
| --- | --- | --- |
| 3071.22 | 3085.19 | 3099.16 |
| 3099.64 | 3111.21 | 3122.77 |
| 3125.22 | 3137.00 | 3148.78 |
| 3149.02 | 3156.94 | 3164.86 |
| 3165.70 | 3177.13 | 3188.57 |
| 3189.67 | 3198.85 | 3208.03 |
| 3208.33 | 3216.82 | 3225.30 |
| 3231.00 | 3243.53 | 3256.07 |
| 3256.90 | 3267.00 | 3277.10 |
| 3305.44 | 3314.98 | 3324.51 |
| 3353.79 | 3366.37 | 3378.94 |
| 3384.77 | 3396.02 | 3407.27 |
| 3410.04 | 3422.21 | 3434.37 |
| 3434.51 | 3443.90 | 3453.30 |
| 3454.74 | 3466.38 | 3478.02 |
| 3540.72 | 3555.53 | 3570.35 |
| 3583.14 | 3593.09 | 3603.05 |
| 3667.06 | 3681.88 | 3696.70 |
| 3697.35 | 3705.33 | 3713.31 |
| 3747.09 | 3755.81 | 3764.52 |
| 3766.63 | 3776.40 | 3786.17 |
| 3811.87 | 3821.31 | 3830.74 |
| 3832.00 | 3841.64 | 3851.28 |
| 3860.09 | 3867.51 | 3874.93 |
| 3877.78 | 3888.14 | 3898.49 |
| 3899.28 | 3907.43 | 3915.58 |
| 3915.70 | 3927.75 | 3939.80 |
| 3943.30 | 3952.26 | 3961.21 |
| 3999.11 | 4011.41 | 4023.71 |
| 4023.91 | 4031.43 | 4038.96 |
| 4039.25 | 4051.40 | 4063.54 |
| 4080.14 | 4094.83 | 4109.53 |
| 4112.17 | 4119.37 | 4126.57 |
| 4127.25 | 4133.39 | 4139.52 |
| 4198.95 | 4210.81 | 4222.68 |
| 4258.83 | 4266.50 | 4274.18 |
| 4276.79 | 4289.24 | 4301.69 |
| 4332.05 | 4341.63 | 4351.22 |
| 4351.40 | 4359.83 | 4368.27 |
| 4372.40 | 4381.03 | 4389.66 |
| 4397.29 | 4407.28 | 4417.26 |
| 4427.40 | 4433.22 | 4439.04 |
| 4439.75 | 4443.96 | 4448.18 |
| 4449.38 | 4461.23 | 4473.07 |
| 4502.53 | 4508.75 | 4514.98 |
| 4553.30 | 4565.57 | 4577.84 |
| 4580.87 | 4586.84 | 4592.81 |
| 4593.22 | 4599.59 | 4605.96 |
| 4618.51 | 4625.99 | 4633.46 |
| 4633.75 | 4642.42 | 4651.09 |
| 4667.54 | 4679.99 | 4692.43 |
| 4698.76 | 4713.31 | 4727.86 |
| 4747.49 | 4755.82 | 4764.15 |
| 4770.57 | 4776.34 | 4782.12 |
| 4782.62 | 4790.85 | 4799.08 |
| 4807.16 | 4819.05 | 4830.95 |
| 4845.90 | 4857.70 | 4869.49 |
| 4885.05 | 4893.33 | 4901.61 |
| 4910.19 | 4919.12 | 4928.06 |
| 4928.26 | 4938.24 | 4948.23 |
| 4949.44 | 4964.30 | 4979.15 |
| 4989.38 | 5000.07 | 5010.76 |
| 5012.17 | 5020.40 | 5028.63 |
| 5033.64 | 5041.17 | 5048.71 |
| 5048.95 | 5054.98 | 5061.00 |
| 5061.10 | 5070.88 | 5080.67 |
| 5093.87 | 5106.47 | 5119.06 |
| 5120.38 | 5127.97 | 5135.56 |
| 5162.99 | 5185.80 | 5208.61 |
| 5209.58 | 5224.44 | 5239.30 |
| 5240.40 | 5251.05 | 5261.69 |
| 5274.04 | 5288.09 | 5302.14 |
| 5351.59 | 5362.36 | 5373.12 |
| 5396.97 | 5404.07 | 5411.16 |
| 5411.52 | 5418.07 | 5424.63 |
| 5424.89 | 5431.54 | 5438.18 |
| 5442.72 | 5449.54 | 5456.36 |
| 5512.62 | 5520.50 | 5528.38 |
| 5540.44 | 5552.25 | 5564.06 |
| 5564.15 | 5573.62 | 5583.09 |
| 5685.16 | 5693.39 | 5701.62 |
| 5701.82 | 5708.30 | 5714.77 |
| 5714.97 | 5720.49 | 5726.01 |
| 5726.03 | 5734.42 | 5742.81 |
| 5743.56 | 5750.24 | 5756.93 |
| 5757.29 | 5764.16 | 5771.03 |
| 5771.12 | 5778.62 | 5786.11 |
| 5786.29 | 5794.96 | 5803.62 |
| 5803.89 | 5810.08 | 5816.27 |
| 5816.42 | 5822.76 | 5829.11 |
| 5832.02 | 5840.46 | 5848.89 |
| 5850.08 | 5863.91 | 5877.73 |
| 5879.59 | 5888.74 | 5897.90 |
| 5898.07 | 5909.77 | 5921.47 |
| 5922.62 | 5934.73 | 5946.84 |
| 5949.41 | 5963.90 | 5978.40 |
| 5978.83 | 5987.76 | 5996.69 |
| 5998.01 | 6008.58 | 6019.14 |
| 6020.13 | 6028.93 | 6037.72 |
| 6054.61 | 6061.94 | 6069.27 |
| 6069.47 | 6082.86 | 6096.26 |
| 6099.57 | 6109.12 | 6118.68 |
| 6134.48 | 6148.68 | 6162.88 |
| 6165.75 | 6175.04 | 6184.34 |
| 6186.65 | 6194.45 | 6202.25 |
| 6202.33 | 6209.35 | 6216.38 |
| 6216.68 | 6224.86 | 6233.04 |
| 6275.16 | 6284.15 | 6293.14 |
| 6293.16 | 6301.49 | 6309.82 |
| 6322.27 | 6331.46 | 6340.64 |
| 6378.77 | 6393.09 | 6407.42 |
| 6409.41 | 6479.04 | 6548.68 |
| 6553.89 | 6564.68 | 6575.47 |
| 6575.85 | 6589.26 | 6602.67 |
| 6604.74 | 6675.06 | 6745.39 |
| 6779.07 | 6798.12 | 6817.17 |
| 6825.83 | 6837.67 | 6849.52 |
| 6849.89 | 6859.44 | 6868.99 |
| 6869.08 | 6878.92 | 6888.75 |
| 6889.03 | 6896.99 | 6904.95 |
| 6911.60 | 6920.97 | 6930.34 |
| 6930.88 | 6939.55 | 6948.22 |
| 6948.87 | 6956.18 | 6963.49 |
| 6963.58 | 6971.11 | 6978.64 |
| 6979.01 | 6995.27 | 7011.52 |
| 7011.77 | 7019.83 | 7027.88 |
| 7029.37 | 7033.60 | 7037.84 |
| 7037.91 | 7046.82 | 7055.73 |
| 7055.81 | 7060.15 | 7064.50 |
| 7065.49 | 7072.90 | 7080.31 |
| 7118.24 | 7143.95 | 7169.66 |
| 7178.66 | 7189.32 | 7199.97 |
| 7234.04 | 7243.67 | 7253.30 |
| 7279.59 | 7292.85 | 7306.11 |
| 7309.51 | 7318.12 | 7326.73 |
| 7327.41 | 7332.74 | 7338.06 |
| 7375.19 | 7390.07 | 7404.95 |
| 7406.19 | 7448.51 | 7490.84 |
| *7553.58 | 7566.50 | 7579.42 |
| *7659.19 | 7672.34 | 7685.48 |
| 7731.02 | 7736.79 | 7742.56 |
| 7742.75 | 7751.34 | 7759.93 |
| 7760.24 | 7767.77 | 7775.30 |
| 7776.52 | 7788.92 | 7801.31 |
| 7803.18 | 7820.32 | 7837.46 |
| *7924.01 | 7937.38 | 7950.75 |

TABLE 43-continued

Appendix A: List of feature definitions
The features marked with an asterisk * were removed from the final
feature table, and used only for batch correction.

| Left M/Z | Center M/Z | Right M/Z |
|---|---|---|
| 7984.80 | 7994.91 | 8005.01 |
| 8006.66 | 8018.69 | 8030.72 |
| *8030.75 | 8041.85 | 8052.96 |
| 8131.01 | 8153.05 | 8175.09 |
| 8192.54 | 8215.68 | 8238.82 |
| 8306.66 | 8314.70 | 8322.74 |
| 8353.19 | 8366.02 | 8378.85 |
| 8401.71 | 8411.17 | 8420.63 |
| 8420.71 | 8428.79 | 8436.87 |
| 8466.84 | 8474.84 | 8482.84 |
| 8483.32 | 8489.05 | 8494.77 |
| 8516.01 | 8528.96 | 8541.91 |
| 8555.29 | 8565.12 | 8574.94 |
| 8575.31 | 8592.03 | 8608.74 |
| 8650.35 | 8659.11 | 8667.86 |
| 8754.04 | 8766.76 | 8779.48 |
| 8799.09 | 8820.53 | 8841.97 |
| 8860.56 | 8871.76 | 8882.96 |
| 8882.98 | 8891.91 | 8900.84 |
| 8904.09 | 8925.16 | 8946.24 |
| 8954.36 | 8961.34 | 8968.33 |
| 8968.81 | 8978.23 | 8987.65 |
| 8988.02 | 8998.68 | 9009.33 |
| 9010.43 | 9019.53 | 9028.62 |
| 9028.78 | 9037.31 | 9045.84 |
| 9066.55 | 9077.91 | 9089.26 |
| 9089.32 | 9096.91 | 9104.51 |
| 9112.47 | 9133.46 | 9154.45 |
| 9196.31 | 9207.88 | 9219.45 |
| 9234.27 | 9243.94 | 9253.60 |
| 9254.17 | 9263.30 | 9272.44 |
| 9272.68 | 9289.41 | 9306.14 |
| 9308.35 | 9319.83 | 9331.31 |
| 9341.10 | 9374.82 | 9408.53 |
| 9411.21 | 9454.03 | 9496.84 |
| 9560.23 | 9585.25 | 9610.26 |
| 9613.48 | 9626.56 | 9639.65 |
| 9639.94 | 9647.57 | 9655.20 |
| 9688.55 | 9723.57 | 9758.58 |
| 9903.45 | 9934.33 | 9965.21 |
| 10128.04 | 10139.87 | 10151.71 |
| 10152.46 | 10161.84 | 10171.22 |
| 10171.98 | 10184.57 | 10197.16 |
| 10197.54 | 10211.07 | 10224.60 |
| 10249.52 | 10262.23 | 10274.94 |
| 10295.62 | 10305.69 | 10315.75 |
| 10328.34 | 10350.14 | 10371.93 |
| 10435.64 | 10450.45 | 10465.26 |
| 10465.61 | 10482.62 | 10499.63 |
| 10518.75 | 10564.38 | 10610.01 |
| 10615.18 | 10638.37 | 10661.56 |
| 10711.79 | 10737.82 | 10763.85 |
| 10764.79 | 10775.15 | 10785.51 |
| 10828.47 | 10847.99 | 10867.50 |
| 10951.44 | 10963.37 | 10975.30 |
| 11028.77 | 11056.40 | 11084.03 |
| 11090.89 | 11107.43 | 11123.96 |
| 11132.45 | 11152.43 | 11172.40 |
| 11285.82 | 11305.10 | 11324.39 |
| 11378.42 | 11392.26 | 11406.11 |
| 11428.16 | 11442.74 | 11457.32 |
| 11468.24 | 11485.30 | 11502.35 |
| 11513.71 | 11530.99 | 11548.26 |
| 11567.26 | 11584.42 | 11601.59 |
| 11611.34 | 11634.82 | 11658.30 |
| 11670.69 | 11686.46 | 11702.22 |
| 11719.74 | 11732.72 | 11745.69 |
| 11746.38 | 11756.13 | 11765.89 |
| 11769.80 | 11786.10 | 11802.40 |
| 11826.75 | 11843.48 | 11860.20 |
| 11876.81 | 11889.88 | 11902.95 |
| 11903.39 | 11913.25 | 11923.11 |
| 11927.82 | 11938.26 | 11948.69 |
| 11974.12 | 11997.34 | 12020.56 |
| 12084.48 | 12116.90 | 12149.32 |
| 12151.24 | 12160.63 | 12170.03 |
| 12266.86 | 12290.16 | 12313.47 |
| 12552.61 | 12629.48 | 12706.34 |
| 12723.06 | 12738.33 | 12753.59 |
| 12769.89 | 12789.06 | 12808.24 |
| 12834.49 | 12917.52 | 13000.55 |
| 13018.32 | 13031.40 | 13044.48 |
| 13049.54 | 13076.86 | 13104.18 |
| 13119.56 | 13135.29 | 13151.02 |
| 13265.30 | 13276.12 | 13286.94 |
| 13304.84 | 13325.96 | 13347.09 |
| 13351.99 | 13364.15 | 13376.31 |
| 13501.19 | 13524.33 | 13547.48 |
| 13554.22 | 13569.52 | 13584.82 |
| 13602.38 | 13612.58 | 13622.78 |
| 13708.20 | 13723.60 | 13739.00 |
| 13740.40 | 13762.02 | 13783.64 |
| 13783.92 | 13795.98 | 13808.04 |
| 13832.96 | 13846.00 | 13859.04 |
| 13860.73 | 13881.13 | 13901.52 |
| 13905.76 | 13917.74 | 13929.71 |
| 13929.96 | 13944.37 | 13958.78 |
| 13959.98 | 13981.28 | 14002.58 |
| 14014.11 | 14067.59 | 14121.06 |
| 14122.86 | 14174.53 | 14226.20 |
| 14229.93 | 14254.82 | 14279.70 |
| 14280.60 | 14301.90 | 14323.20 |
| 14401.51 | 14431.22 | 14460.94 |
| 14462.27 | 14541.41 | 14620.56 |
| 14623.06 | 14642.87 | 14662.69 |
| 14684.56 | 14699.66 | 14714.76 |
| 14764.89 | 14786.87 | 14808.84 |
| 14859.96 | 14882.15 | 14904.35 |
| *15114.72 | 15136.98 | 15159.25 |
| *15321.76 | 15344.32 | 15366.88 |
| *15856.28 | 15879.62 | 15902.96 |
| *16066.16 | 16087.64 | 16109.12 |
| 18248.47 | 18271.03 | 18293.59 |
| 18548.49 | 18570.16 | 18591.84 |
| 18603.02 | 18630.68 | 18658.34 |
| 18708.84 | 18730.03 | 18751.21 |
| 18811.43 | 18848.65 | 18885.87 |
| 19343.00 | 19378.06 | 19413.11 |
| 20886.02 | 21156.71 | 21427.39 |
| 21669.84 | 21804.69 | 21939.55 |
| 22566.70 | 22604.25 | 22641.79 |
| 22999.81 | 23033.14 | 23066.47 |
| 23097.51 | 23130.26 | 23163.02 |
| 23213.01 | 23246.92 | 23280.82 |
| 23305.86 | 23353.04 | 23400.22 |
| 23429.20 | 23467.05 | 23504.91 |
| 25144.70 | 25185.27 | 25225.84 |
| 25429.35 | 25473.61 | 25517.87 |
| 25519.61 | 25570.37 | 25621.14 |
| 25624.40 | 25686.01 | 25747.63 |
| 27915.48 | 27962.78 | 28010.08 |
| 28037.85 | 28133.53 | 28229.20 |
| 28237.01 | 28338.55 | 28440.09 |
| 28800.67 | 28859.90 | 28919.13 |
| 28924.34 | 28972.72 | 29021.10 |
| 29030.65 | 29078.60 | 29126.55 |

TABLE 44

Appendix B
Mass spectral peaks (m/z values) for 29 features associated with immune response type 2 used in development of Classifier A

| Left M/Z | Center M/Z | Right M/Z |
|---|---|---|
| 5998.01 | 6008.58 | 6019.14 |
| 8192.54 | 8215.68 | 8238.82 |
| 5922.62 | 5934.73 | 5946.84 |
| 11428.16 | 11442.74 | 11457.32 |
| 5162.99 | 5185.8 | 5208.61 |
| 14764.89 | 14786.87 | 14808.84 |
| 11876.81 | 11889.88 | 11902.95 |
| 3149.02 | 3156.94 | 3164.86 |
| 5786.29 | 5794.96 | 5803.62 |
| 13783.92 | 13795.98 | 13808.04 |
| 10828.47 | 10847.99 | 10867.5 |
| 11513.71 | 11530.99 | 11548.26 |
| 3384.77 | 3396.02 | 3407.27 |
| 6165.75 | 6175.04 | 6184.34 |
| 23305.86 | 23353.04 | 23400.22 |
| 3165.7 | 3177.13 | 3188.57 |
| 3877.78 | 3888.14 | 3898.49 |
| 14859.96 | 14882.15 | 14904.35 |
| 3099.64 | 3111.21 | 3122.77 |
| 5743.56 | 5750.24 | 5756.93 |
| 11903.39 | 11913.25 | 11923.11 |
| 9903.45 | 9934.33 | 9965.21 |
| 11974.12 | 11997.34 | 12020.56 |
| 5685.16 | 5693.39 | 5701.62 |
| 11028.77 | 11056.4 | 11084.03 |
| 4633.75 | 4642.42 | 4651.09 |
| 5726.03 | 5734.42 | 5742.81 |
| 11567.26 | 11584.42 | 11601.59 |
| 11826.75 | 11843.48 | 11860.2 |

What is claimed is:

1. Testing apparatus comprising, in combination:
a mass spectrometer configured to conduct mass spectrometry on a blood-based sample obtained from a cancer patient and obtaining a mass spectrum in the form of a set of integrated intensity values for a multitude of features in the mass spectrum;
a processing unit, and
a nontransitory computer memory storing instructions and classification parameters for at least a first classifier and a second classifier (Classifiers A and D, respectively), for execution by the processing unit,
wherein Classifier A is defined by:
a) a reference set of integrated intensity mass spectral feature values for a set of mass spectral features associated with immune response type 2, the feature values obtained by conducting mass spectrometry on a development set of blood-based samples obtained from a population of non-small cell lung cancer patients treated with an anti-PD1 drug, wherein the set of mass spectral features associated with immune response type 2 comprise a list of features:

| Left M/Z | Center M/Z | Right M/Z |
|---|---|---|
| 5998.01 | 6008.58 | 6019.14 |
| 8192.54 | 8215.68 | 8238.82 |
| 5922.62 | 5934.73 | 5946.84 |
| 11428.16 | 11442.74 | 11457.32 |
| 5162.99 | 5185.8 | 5208.61 |
| 14764.89 | 14786.87 | 14808.84 |
| 11876.81 | 11889.88 | 11902.95 |
| 3149.02 | 3156.94 | 3164.86 |
| 5786.29 | 5794.96 | 5803.62 |
| 13783.92 | 13795.98 | 13808.04 |
| 10828.47 | 10847.99 | 10867.5 |
| 11513.71 | 11530.99 | 11548.26 |
| 3384.77 | 3396.02 | 3407.27 |
| 6165.75 | 6175.04 | 6184.34 |
| 23305.86 | 23353.04 | 23400.22 |
| 3165.7 | 3177.13 | 3188.57 |
| 3877.78 | 3888.14 | 3898.49 |
| 14859.96 | 14882.15 | 14904.35 |
| 3099.64 | 3111.21 | 3122.77 |
| 5743.56 | 5750.24 | 5756.93 |
| 11903.39 | 11913.25 | 11923.11 |
| 9903.45 | 9934.33 | 9965.21 |
| 11974.12 | 11997.34 | 12020.56 |
| 5685.16 | 5693.39 | 5701.62 |
| 11028.77 | 11056.4 | 11084.03 |
| 4633.75 | 4642.42 | 4651.09 |
| 5726.03 | 5734.42 | 5742.81 |
| 11567.26 | 11584.42 | 11601.59 |
| 11826.75 | 11843.48 | 11860.2; | and
b) parameters defining a classification procedure for generating a class label for the mass spectrum of the blood-based sample of the cancer patient by comparing the integrated intensity values of features associated with immune response type 2 in the mass spectrum of the blood-based sample of the cancer patient with the reference set of Classifier A;
wherein Classifier D is defined by:
a) a reference set of integrated intensity mass spectral feature values for a set of mass spectral features, the feature values obtained by conducting mass spectrometry on a development set of blood-based samples obtained from a population of melanoma patients treated with an anti-PD1 drug; and
b) parameters defining a classification procedure for generating a class label for the mass spectrum of the blood-based sample of the cancer patient by comparing the integrated intensity values of features in the mass spectrum of the blood-based sample of the cancer patient with the reference set of Classifier D.

2. The apparatus of claim 1, wherein the computer memory is further configured with program code in the form of logic for comparing the class labels produced by Classifier A and Classifier D on the mass spectrum of the blood-based sample of the cancer patient, wherein if the class labels produced by both Classifier A and Classifier D are "Group1" indicating poor overall survival or progression free survival the cancer patient is predicted to exhibit primary immune resistance if treated with immunotherapy drugs.

3. The apparatus of claim 1, wherein the set of mass spectral features for Classifier D comprises features selected from a list of features:

| Left M/Z | Center M/Z | Right M/Z |
|---|---|---|
| 3071.22 | 3085.19 | 3099.16 |
| 3099.64 | 3111.21 | 3122.77 |
| 3125.22 | 3137.00 | 3148.78 |
| 3149.02 | 3156.94 | 3164.86 |
| 3165.70 | 3177.13 | 3188.57 |
| 3189.67 | 3198.85 | 3208.03 |
| 3208.33 | 3216.82 | 3225.30 |
| 3231.00 | 3243.53 | 3256.07 |
| 3256.90 | 3267.00 | 3277.10 |
| 3305.44 | 3314.98 | 3324.51 |

| Left M/Z | Center M/Z | Right M/Z | | Left M/Z | Center M/Z | Right M/Z |
|---|---|---|---|---|---|---|
| 3353.79 | 3366.37 | 3378.94 | | 5786.29 | 5794.96 | 5803.62 |
| 3384.77 | 3396.02 | 3407.27 | | 5803.89 | 5810.08 | 5816.27 |
| 3410.04 | 3422.21 | 3434.37 | | 5816.42 | 5822.76 | 5829.11 |
| 3434.51 | 3443.90 | 3453.30 | | 5832.02 | 5840.46 | 5848.89 |
| 3454.74 | 3466.38 | 3478.02 | | 5850.08 | 5863.91 | 5877.73 |
| 3540.72 | 3555.53 | 3570.35 | | 5879.59 | 5888.74 | 5897.90 |
| 3583.14 | 3593.09 | 3603.05 | | 5898.07 | 5909.77 | 5921.47 |
| 3667.06 | 3681.88 | 3696.70 | | 5922.62 | 5934.73 | 5946.84 |
| 3697.35 | 3705.33 | 3713.31 | | 5949.41 | 5963.90 | 5978.40 |
| 3747.09 | 3755.81 | 3764.52 | | 5978.83 | 5987.76 | 5996.69 |
| 3766.63 | 3776.40 | 3786.17 | | 5998.01 | 6008.58 | 6019.14 |
| 3811.87 | 3821.31 | 3830.74 | | 6020.13 | 6028.93 | 6037.72 |
| 3832.00 | 3841.64 | 3851.28 | | 6054.61 | 6061.94 | 6069.27 |
| 3860.09 | 3867.51 | 3874.93 | | 6069.47 | 6082.86 | 6096.26 |
| 3877.78 | 3888.14 | 3898.49 | | 6099.57 | 6109.12 | 6118.68 |
| 3899.28 | 3907.43 | 3915.58 | | 6134.48 | 6148.68 | 6162.88 |
| 3915.70 | 3927.75 | 3939.80 | | 6165.75 | 6175.04 | 6184.34 |
| 3943.30 | 3952.26 | 3961.21 | | 6186.65 | 6194.45 | 6202.25 |
| 3999.11 | 4011.41 | 4023.71 | | 6202.33 | 6209.35 | 6216.38 |
| 4023.91 | 4031.43 | 4038.96 | | 6216.68 | 6224.86 | 6233.04 |
| 4039.25 | 4051.40 | 4063.54 | | 6275.16 | 6284.15 | 6293.14 |
| 4080.14 | 4094.83 | 4109.53 | | 6293.16 | 6301.49 | 6309.82 |
| 4112.17 | 4119.37 | 4126.57 | | 6322.27 | 6331.46 | 6340.64 |
| 4127.25 | 4133.39 | 4139.52 | | 6378.77 | 6393.09 | 6407.42 |
| 4198.95 | 4210.81 | 4222.68 | | 6409.41 | 6479.04 | 6548.68 |
| 4258.83 | 4266.50 | 4274.18 | | 6553.89 | 6564.68 | 6575.47 |
| 4276.79 | 4289.24 | 4301.69 | | 6575.85 | 6589.26 | 6602.67 |
| 4332.05 | 4341.63 | 4351.22 | | 6604.74 | 6675.06 | 6745.39 |
| 4351.40 | 4359.83 | 4368.27 | | 6779.07 | 6798.12 | 6817.17 |
| 4372.40 | 4381.03 | 4389.66 | | 6825.83 | 6837.67 | 6849.52 |
| 4397.29 | 4407.28 | 4417.26 | | 6849.89 | 6859.44 | 6868.99 |
| 4427.40 | 4433.22 | 4439.04 | | 6869.08 | 6878.92 | 6888.75 |
| 4439.75 | 4443.96 | 4448.18 | | 6889.03 | 6896.99 | 6904.95 |
| 4449.38 | 4461.23 | 4473.07 | | 6911.60 | 6920.97 | 6930.34 |
| 4502.53 | 4508.75 | 4514.98 | | 6930.88 | 6939.55 | 6948.22 |
| 4553.30 | 4565.57 | 4577.84 | | 6948.87 | 6956.18 | 6963.49 |
| 4580.87 | 4586.84 | 4592.81 | | 6963.58 | 6971.11 | 6978.64 |
| 4593.22 | 4599.59 | 4605.96 | | 6979.01 | 6995.27 | 7011.52 |
| 4618.51 | 4625.99 | 4633.46 | | 7011.77 | 7019.83 | 7027.88 |
| 4633.75 | 4642.42 | 4651.09 | | 7029.37 | 7033.60 | 7037.84 |
| 4667.54 | 4679.99 | 4692.43 | | 7037.91 | 7046.82 | 7055.73 |
| 4698.76 | 4713.31 | 4727.86 | | 7055.81 | 7060.15 | 7064.50 |
| 4747.49 | 4755.82 | 4764.15 | | 7065.49 | 7072.90 | 7080.31 |
| 4770.57 | 4776.34 | 4782.12 | | 7118.24 | 7143.95 | 7169.66 |
| 4782.62 | 4790.85 | 4799.08 | | 7178.66 | 7189.32 | 7199.97 |
| 4807.16 | 4819.05 | 4830.95 | | 7234.04 | 7243.67 | 7253.30 |
| 4845.90 | 4857.70 | 4869.49 | | 7279.59 | 7292.85 | 7306.11 |
| 4885.05 | 4893.33 | 4901.61 | | 7309.51 | 7318.12 | 7326.73 |
| 4910.19 | 4919.12 | 4928.06 | | 7327.41 | 7332.74 | 7338.06 |
| 4928.26 | 4938.24 | 4948.23 | | 7375.19 | 7390.07 | 7404.95 |
| 4949.44 | 4964.30 | 4979.15 | | 7406.19 | 7448.51 | 7490.84 |
| 4989.38 | 5000.07 | 5010.76 | | *7553.58 | 7566.50 | 7579.42 |
| 5012.17 | 5020.40 | 5028.63 | | *7659.19 | 7672.34 | 7685.48 |
| 5033.64 | 5041.17 | 5048.71 | | 7731.02 | 7736.79 | 7742.56 |
| 5048.95 | 5054.98 | 5061.00 | | 7742.75 | 7751.34 | 7759.93 |
| 5061.10 | 5070.88 | 5080.67 | | 7760.24 | 7767.77 | 7775.30 |
| 5093.87 | 5106.47 | 5119.06 | | 7776.52 | 7788.92 | 7801.31 |
| 5120.38 | 5127.97 | 5135.56 | | 7803.18 | 7820.32 | 7837.46 |
| 5162.99 | 5185.80 | 5208.61 | | *7924.01 | 7937.38 | 7950.75 |
| 5209.58 | 5224.44 | 5239.30 | | 7984.80 | 7994.91 | 8005.01 |
| 5240.40 | 5251.05 | 5261.69 | | 8006.66 | 8018.69 | 8030.72 |
| 5274.04 | 5288.09 | 5302.14 | | *8030.75 | 8041.85 | 8052.96 |
| 5351.59 | 5362.36 | 5373.12 | | 8131.01 | 8153.05 | 8175.09 |
| 5396.97 | 5404.07 | 5411.16 | | 8192.54 | 8215.68 | 8238.82 |
| 5411.52 | 5418.07 | 5424.63 | | 8306.66 | 8314.70 | 8322.74 |
| 5424.89 | 5431.54 | 5438.18 | | 8353.19 | 8366.02 | 8378.85 |
| 5442.72 | 5449.54 | 5456.36 | | 8401.71 | 8411.17 | 8420.63 |
| 5512.62 | 5520.50 | 5528.38 | | 8420.71 | 8428.79 | 8436.87 |
| 5540.44 | 5552.25 | 5564.06 | | 8466.84 | 8474.84 | 8482.84 |
| 5564.15 | 5573.62 | 5583.09 | | 8483.32 | 8489.05 | 8494.77 |
| 5685.16 | 5693.39 | 5701.62 | | 8516.01 | 8528.96 | 8541.91 |
| 5701.82 | 5708.30 | 5714.77 | | 8555.29 | 8565.12 | 8574.94 |
| 5714.97 | 5720.49 | 5726.01 | | 8575.31 | 8592.03 | 8608.74 |
| 5726.03 | 5734.42 | 5742.81 | | 8650.35 | 8659.11 | 8667.86 |
| 5743.56 | 5750.24 | 5756.93 | | 8754.04 | 8766.76 | 8779.48 |
| 5757.29 | 5764.16 | 5771.03 | | 8799.09 | 8820.53 | 8841.97 |
| 5771.12 | 5778.62 | 5786.11 | | 8860.56 | 8871.76 | 8882.96 |

| Left M/Z | Center M/Z | Right M/Z |
|---|---|---|
| 8882.98 | 8891.91 | 8900.84 |
| 8904.09 | 8925.16 | 8946.24 |
| 8954.36 | 8961.34 | 8968.33 |
| 8968.81 | 8978.23 | 8987.65 |
| 8988.02 | 8998.68 | 9009.33 |
| 9010.43 | 9019.53 | 9028.62 |
| 9028.78 | 9037.31 | 9045.84 |
| 9066.55 | 9077.91 | 9089.26 |
| 9089.32 | 9096.91 | 9104.51 |
| 9112.47 | 9133.46 | 9154.45 |
| 9196.31 | 9207.88 | 9219.05 |
| 9234.27 | 9243.94 | 9253.60 |
| 9254.17 | 9263.30 | 9272.44 |
| 9272.68 | 9289.41 | 9306.14 |
| 9308.35 | 9319.83 | 9331.31 |
| 9341.10 | 9374.82 | 9408.53 |
| 9411.21 | 9454.03 | 9496.84 |
| 9560.23 | 9585.25 | 9610.26 |
| 9613.48 | 9626.56 | 9639.65 |
| 9639.94 | 9647.57 | 9655.20 |
| 9688.55 | 9723.57 | 9758.58 |
| 9903.45 | 9934.33 | 9965.21 |
| 10128.04 | 10139.87 | 10151.71 |
| 10152.46 | 10161.84 | 10171.22 |
| 10171.98 | 10184.57 | 10197.16 |
| 10197.54 | 10211.07 | 10224.60 |
| 10249.52 | 10262.23 | 10274.94 |
| 10295.62 | 10305.69 | 10315.75 |
| 10328.34 | 10350.14 | 10371.93 |
| 10435.64 | 10450.45 | 10465.26 |
| 10465.61 | 10482.62 | 10499.63 |
| 10518.75 | 10564.38 | 10610.01 |
| 10615.18 | 10638.37 | 10661.56 |
| 10711.79 | 10737.82 | 10763.85 |
| 10764.79 | 10775.15 | 10785.51 |
| 10828.47 | 10847.99 | 10867.50 |
| 10951.44 | 10963.37 | 10975.30 |
| 11028.77 | 11056.40 | 11084.03 |
| 11090.89 | 11107.43 | 11123.96 |
| 11132.45 | 11152.43 | 11172.40 |
| 11285.82 | 11305.10 | 11324.39 |
| 11378.42 | 11392.26 | 11406.11 |
| 11428.16 | 11442.74 | 11457.32 |
| 11468.24 | 11485.30 | 11502.35 |
| 11513.71 | 11530.99 | 11548.26 |
| 11567.26 | 11584.42 | 11601.59 |
| 11611.34 | 11634.82 | 11658.30 |
| 11670.69 | 11686.46 | 11702.22 |
| 11719.74 | 11732.72 | 11745.69 |
| 11746.38 | 11756.13 | 11765.89 |
| 11769.80 | 11786.10 | 11802.40 |
| 11826.75 | 11843.48 | 11860.20 |
| 11876.81 | 11889.88 | 11902.95 |
| 11903.39 | 11913.25 | 11923.11 |
| 11927.82 | 11938.26 | 11948.69 |
| 11974.12 | 11997.34 | 12020.56 |
| 12084.48 | 12116.90 | 12149.32 |
| 12151.24 | 12160.63 | 12170.03 |
| 12266.86 | 12290.16 | 12313.47 |
| 12552.61 | 12629.48 | 12706.34 |
| 12723.06 | 12738.33 | 12753.59 |
| 12769.89 | 12789.06 | 12808.24 |
| 12834.49 | 12917.52 | 13000.55 |
| 13018.32 | 13031.40 | 13044.48 |
| 13049.54 | 13076.86 | 13104.18 |
| 13119.56 | 13135.29 | 13151.02 |
| 13265.30 | 13276.12 | 13286.94 |
| 13304.84 | 13325.96 | 13347.09 |
| 13351.99 | 13364.15 | 13376.31 |
| 13501.19 | 13524.33 | 13547.48 |
| 13554.22 | 13569.52 | 13584.82 |
| 13602.38 | 13612.58 | 13622.78 |
| 13708.20 | 13723.60 | 13739.00 |
| 13740.40 | 13762.02 | 13783.64 |
| 13783.92 | 13795.98 | 13808.04 |
| 13832.96 | 13846.00 | 13859.04 |
| 13860.73 | 13881.13 | 13901.52 |
| 13905.76 | 13917.74 | 13929.71 |
| 13929.96 | 13944.37 | 13958.78 |
| 13959.98 | 13981.28 | 14002.58 |
| 14014.11 | 14067.59 | 14121.06 |
| 14122.86 | 14174.53 | 14226.20 |
| 14229.93 | 14254.82 | 14279.70 |
| 14280.60 | 14301.90 | 14323.20 |
| 14401.51 | 14431.22 | 14460.94 |
| 14462.27 | 14541.41 | 14620.56 |
| 14623.06 | 14642.87 | 14662.69 |
| 14684.56 | 14699.66 | 14714.76 |
| 14764.89 | 14786.87 | 14808.84 |
| 14859.96 | 14882.15 | 14904.35 |
| *15114.72 | 15136.98 | 15159.25 |
| *15321.76 | 15344.32 | 15366.88 |
| *15856.28 | 15879.62 | 15902.96 |
| *16066.16 | 16087.64 | 16109.12 |
| 18248.47 | 18271.03 | 18293.59 |
| 18548.49 | 18570.16 | 18591.84 |
| 18603.02 | 18630.68 | 18658.34 |
| 18708.84 | 18730.03 | 18751.21 |
| 18811.43 | 18848.65 | 18885.87 |
| 19343.00 | 19378.06 | 19413.11 |
| 20886.02 | 21156.71 | 21427.39 |
| 21669.84 | 21804.69 | 21939.55 |
| 22566.70 | 22604.25 | 22641.79 |
| 22999.81 | 23033.14 | 23066.47 |
| 23097.51 | 23130.26 | 23163.02 |
| 23213.01 | 23246.92 | 23280.82 |
| 23305.86 | 23353.04 | 23400.22 |
| 23429.20 | 23467.05 | 23504.91 |
| 25144.70 | 25185.27 | 25225.84 |
| 25429.35 | 25473.61 | 25517.87 |
| 25519.61 | 25570.37 | 25621.14 |
| 25624.40 | 25686.01 | 25747.63 |
| 27915.48 | 27962.78 | 28010.08 |
| 28037.85 | 28133.53 | 28229.20 |
| 28237.01 | 28338.55 | 28440.09 |
| 28800.67 | 28859.90 | 28919.13 |
| 28924.34 | 28972.72 | 29021.10 |
| 29030.65 | 29078.60 | 29126.55. |

4. The apparatus of claim 1, wherein the classification procedure of Classifiers A and D comprises an ensemble average of a plurality of master Classifiers each developed from different realizations of a splitting of the development set into training and test sets.

5. The apparatus of claim 4, wherein each of the master Classifiers comprise a combination of filtered mini-Classifiers combined using a regularized combination method.

6. The apparatus of claim 2, wherein the immunotherapy drugs comprise an anti-PD1 or anti-PDL1 drug.

7. The apparatus of claim 6, wherein the immunotherapy drugs comprise nivolumab.

8. The apparatus of claim 1, wherein the cancer patient has non-small-cell lung cancer.

9. A method of detecting a first and second class label in a cancer patient, comprising, in combination:
conducting mass spectrometry on a blood-based sample obtained from the cancer patient and obtaining mass spectral data in the form of a set of integrated intensity values for a multitude of features in the mass spectral data;
operating on the mass spectral data with a programmed computer implementing at least a first classifier and a second classifier (Classifiers A and D, respectively), wherein Classifier A is defined by:
a) a first reference set of integrated intensity mass spectral feature values for a set of mass spectral features associated with immune response type 2, the feature values obtained by conducting mass spectrometry on a development set of blood-based samples obtained from a first population of non-small cell lung cancer patients treated with an anti-PD-1 drug, wherein the set of mass spectral features associated with immune response type 2 comprise a list of features:

| Left M/Z | Center M/Z | Right M/Z |
|---|---|---|
| 5998.01 | 6008.58 | 6019.14 |
| 8192.54 | 8215.68 | 8238.82 |
| 5922.62 | 5934.73 | 5946.84 |
| 11428.16 | 11442.74 | 11457.32 |
| 5162.99 | 5185.8 | 5208.61 |
| 14764.89 | 14786.87 | 14808.84 |
| 11876.81 | 11889.88 | 11902.95 |
| 3149.02 | 3156.94 | 3164.86 |
| 5786.29 | 5794.96 | 5803.62 |
| 13783.92 | 13795.98 | 13808.04 |
| 10828.47 | 10847.99 | 10867.5 |
| 11513.71 | 11530.99 | 11548.26 |
| 3384.77 | 3396.02 | 3407.27 |
| 6165.75 | 6175.04 | 6184.34 |
| 23305.86 | 23353.04 | 23400.22 |
| 3165.7 | 3177.13 | 3188.57 |
| 3877.78 | 3888.14 | 3898.49 |
| 14859.96 | 14882.15 | 14904.35 |
| 3099.64 | 3111.21 | 3122.77 |
| 5743.56 | 5750.24 | 5756.93 |
| 11903.39 | 11913.25 | 11923.11 |
| 9903.45 | 9934.33 | 9965.21 |
| 11974.12 | 11997.34 | 12020.56 |
| 5685.16 | 5693.39 | 5701.62 |
| 11028.77 | 11056.4 | 11084.03 |
| 4633.75 | 4642.42 | 4651.09 |
| 5726.03 | 5734.42 | 5742.81 |
| 11567.26 | 11584.42 | 11601.59 |
| 11826.75 | 11843.48 | 11860.2; | and
  b) parameters defining a classification procedure for generating a first class label for the mass spectral data of the blood-based sample of the cancer patient by comparing the integrated intensity values of features associated with immune response type 2 in the mass spectral data of the blood-based sample of the cancer patient with the first reference set of Classifier A;
  wherein Classifier D is defined by:
    a) a second reference set of integrated intensity mass spectral feature values for a set of mass spectral features, the feature values obtained by conducting mass spectrometry on a development set of blood-based samples obtained from a second population of melanoma patients treated with an anti-PD-1 drug; and
    b) parameters defining a classification procedure for generating a second class label for the mass spectral data of the blood-based sample of the cancer patient by comparing the integrated intensity values of features in the mass spectral data of the blood-based sample of the cancer patient with the second reference set of Classifier D,
  wherein the first and second class label are detected.

10. The method of claim 9, wherein the patient has non-small-cell lung cancer.

11. The method of claim 9, further comprising with the aid of the programmed computer, classifying the mass spectral data with at least the second classifier (Classifier D) and a third classifier (Classifier B), wherein Classifier B is defined by:
    a) a third reference set of integrated intensity mass spectral feature values for a set of mass spectral features, the feature values obtained by conducting mass spectrometry on a development set of blood-based samples obtained from a third population of non-small cell lung cancer patients treated with an anti-PD1 drug; and
    b) parameters defining a classification procedure for generating a class label for the mass spectral data of the blood-based sample of the cancer patient by comparing the integrated intensity values of features in the mass spectral data of the blood-based sample of the cancer patient with the third reference set of Classifier B; and
  wherein where the class labels produced by both Classifier D and Classifier B are "Group2" indicating good overall survival or progression free survival the cancer patient is predicted to not exhibit primary immune resistance when treated with immunotherapy drugs.

12. The method of claim 9, wherein the programmed computer is further configured with program code in the form of logic for comparing the class labels produced by Classifier A and Classifier D on the mass spectral data of the blood-based sample of the cancer patient, wherein if the class labels generated by both Classifier A and Classifier D are "Group1" indicating poor overall survival or progression free survival the cancer patient is predicted to exhibit primary immune resistance if treated with immunotherapy drugs.

13. The method of claim 12, wherein the immunotherapy drugs comprise an anti-PD-1 or anti-PDL-1 drug.

14. The method of claim 13, wherein the immunotherapy drugs comprise nivolumab.

15. A method of detecting a class label in a non-small-cell lung cancer patient, comprising:
  a) conducting mass spectrometry on a blood-based sample of the cancer patient and obtaining mass spectrometry data;
  b) obtaining integrated intensity values in the mass spectrometry data of mass spectral features, wherein the mass spectral features are selected from a list of mass spectral features:

| Left M/Z | Center M/Z | Right M/Z |
|---|---|---|
| 3071.22 | 3085.19 | 3099.16 |
| 3099.64 | 3111.21 | 3122.77 |
| 3125.22 | 3137.00 | 3148.78 |
| 3149.02 | 3156.94 | 3164.86 |
| 3165.70 | 3177.13 | 3188.57 |
| 3189.67 | 3198.85 | 3208.03 |
| 3208.33 | 3216.82 | 3225.30 |
| 3231.00 | 3243.53 | 3256.07 |
| 3256.90 | 3267.00 | 3277.10 |
| 3305.44 | 3314.98 | 3324.51 |
| 3353.79 | 3366.37 | 3378.94 |
| 3384.77 | 3396.02 | 3407.27 |
| 3410.04 | 3422.21 | 3434.37 |
| 3434.51 | 3443.90 | 3453.30 |
| 3454.74 | 3466.38 | 3478.02 |
| 3540.72 | 3555.53 | 3570.35 |
| 3583.14 | 3593.09 | 3603.05 |
| 3667.06 | 3681.88 | 3696.70 |
| 3697.35 | 3705.33 | 3713.31 |
| 3747.09 | 3755.81 | 3764.52 |
| 3766.63 | 3776.40 | 3786.17 |
| 3811.87 | 3821.31 | 3830.74 |
| 3832.00 | 3841.64 | 3851.28 |
| 3860.09 | 3867.51 | 3874.93 |
| 3877.78 | 3888.14 | 3898.49 |
| 3899.28 | 3907.43 | 3915.58 |
| 3915.70 | 3927.75 | 3939.80 |
| 3943.30 | 3952.26 | 3961.21 |
| 3999.11 | 4011.41 | 4023.71 |

| Left M/Z | Center M/Z | Right M/Z |
|---|---|---|
| 4023.91 | 4031.43 | 4038.96 |
| 4039.25 | 4051.40 | 4063.54 |
| 4080.14 | 4094.83 | 4109.53 |
| 4112.17 | 4119.37 | 4126.57 |
| 4127.25 | 4133.39 | 4139.52 |
| 4198.95 | 4210.81 | 4222.68 |
| 4258.83 | 4266.50 | 4274.18 |
| 4276.79 | 4289.24 | 4301.69 |
| 4332.05 | 4341.63 | 4351.22 |
| 4351.40 | 4359.83 | 4368.27 |
| 4372.40 | 4381.03 | 4389.66 |
| 4397.29 | 4407.28 | 4417.26 |
| 4427.40 | 4433.22 | 4439.04 |
| 4439.75 | 4443.96 | 4448.18 |
| 4449.38 | 4461.23 | 4473.07 |
| 4502.53 | 4508.75 | 4514.98 |
| 4553.30 | 4565.57 | 4577.84 |
| 4580.87 | 4586.84 | 4592.81 |
| 4593.22 | 4599.59 | 4605.96 |
| 4618.51 | 4625.99 | 4633.46 |
| 4633.75 | 4642.42 | 4651.09 |
| 4667.54 | 4679.99 | 4692.43 |
| 4698.76 | 4713.31 | 4727.86 |
| 4747.49 | 4755.82 | 4764.15 |
| 4770.57 | 4776.34 | 4782.12 |
| 4782.62 | 4790.85 | 4799.08 |
| 4807.16 | 4819.05 | 4830.95 |
| 4845.90 | 4857.70 | 4869.49 |
| 4885.05 | 4893.33 | 4901.61 |
| 4910.19 | 4919.12 | 4928.06 |
| 4928.26 | 4938.24 | 4948.23 |
| 4949.44 | 4964.30 | 4979.15 |
| 4989.38 | 5000.07 | 5010.76 |
| 5012.17 | 5020.40 | 5028.63 |
| 5033.64 | 5041.17 | 5048.71 |
| 5048.95 | 5054.98 | 5061.00 |
| 5061.10 | 5070.88 | 5080.67 |
| 5093.87 | 5106.47 | 5119.06 |
| 5120.38 | 5127.97 | 5135.56 |
| 5162.99 | 5185.80 | 5208.61 |
| 5209.58 | 5224.44 | 5239.30 |
| 5240.40 | 5251.05 | 5261.69 |
| 5274.04 | 5288.09 | 5302.14 |
| 5351.59 | 5362.36 | 5373.12 |
| 5396.97 | 5404.07 | 5411.16 |
| 5411.52 | 5418.07 | 5424.63 |
| 5424.89 | 5431.54 | 5438.18 |
| 5442.72 | 5449.54 | 5456.36 |
| 5512.62 | 5520.50 | 5528.38 |
| 5540.44 | 5552.25 | 5564.06 |
| 5564.15 | 5573.62 | 5583.09 |
| 5685.16 | 5693.39 | 5701.62 |
| 5701.82 | 5708.30 | 5714.77 |
| 5714.97 | 5720.49 | 5726.01 |
| 5726.03 | 5734.42 | 5742.81 |
| 5743.56 | 5750.24 | 5756.93 |
| 5757.29 | 5764.16 | 5771.03 |
| 5771.12 | 5778.62 | 5786.11 |
| 5786.29 | 5794.96 | 5803.62 |
| 5803.89 | 5810.08 | 5816.27 |
| 5816.42 | 5822.76 | 5829.11 |
| 5832.02 | 5840.46 | 5848.89 |
| 5850.08 | 5863.91 | 5877.73 |
| 5879.59 | 5888.74 | 5897.90 |
| 5898.07 | 5909.77 | 5921.47 |
| 5922.62 | 5934.73 | 5946.84 |
| 5949.41 | 5963.90 | 5978.40 |
| 5978.83 | 5987.76 | 5996.69 |
| 5998.01 | 6008.58 | 6019.14 |
| 6020.13 | 6028.93 | 6037.72 |
| 6054.61 | 6061.94 | 6069.27 |
| 6069.47 | 6082.86 | 6096.26 |
| 6099.57 | 6109.12 | 6118.68 |
| 6134.48 | 6148.68 | 6162.88 |
| 6165.75 | 6175.04 | 6184.34 |
| 6186.65 | 6194.45 | 6202.25 |
| 6202.33 | 6209.35 | 6216.38 |
| 6216.68 | 6224.86 | 6233.04 |
| 6275.16 | 6284.15 | 6293.14 |
| 6293.16 | 6301.49 | 6309.82 |
| 6322.27 | 6331.46 | 6340.64 |
| 6378.77 | 6393.09 | 6407.42 |
| 6409.41 | 6479.04 | 6548.68 |
| 6553.89 | 6564.68 | 6575.47 |
| 6575.85 | 6589.26 | 6602.67 |
| 6604.74 | 6675.06 | 6745.39 |
| 6779.07 | 6798.12 | 6817.17 |
| 6825.83 | 6837.67 | 6849.52 |
| 6849.89 | 6859.44 | 6868.99 |
| 6869.08 | 6878.92 | 6888.75 |
| 6889.03 | 6896.99 | 6904.95 |
| 6911.60 | 6920.97 | 6930.34 |
| 6930.88 | 6939.55 | 6948.22 |
| 6948.87 | 6956.18 | 6963.49 |
| 6963.58 | 6971.11 | 6978.64 |
| 6979.01 | 6995.27 | 7011.52 |
| 7011.77 | 7019.83 | 7027.88 |
| 7029.37 | 7033.60 | 7037.84 |
| 7037.91 | 7046.82 | 7055.73 |
| 7055.81 | 7060.15 | 7064.50 |
| 7065.49 | 7072.90 | 7080.31 |
| 7118.24 | 7143.95 | 7169.66 |
| 7178.66 | 7189.32 | 7199.97 |
| 7234.04 | 7243.67 | 7253.30 |
| 7279.59 | 7292.85 | 7306.11 |
| 7309.51 | 7318.12 | 7326.73 |
| 7327.41 | 7332.74 | 7338.06 |
| 7375.19 | 7390.07 | 7404.95 |
| 7406.19 | 7448.51 | 7490.84 |
| *7553.58 | 7566.50 | 7579.42 |
| *7659.19 | 7672.34 | 7685.48 |
| 7731.02 | 7736.79 | 7742.56 |
| 7742.75 | 7751.34 | 7759.93 |
| 7760.24 | 7767.77 | 7775.30 |
| 7776.52 | 7788.92 | 7801.31 |
| 7803.18 | 7820.32 | 7837.46 |
| *7924.01 | 7937.38 | 7950.75 |
| 7984.80 | 7994.91 | 8005.01 |
| 8006.66 | 8018.69 | 8030.72 |
| *8030.75 | 8041.85 | 8052.96 |
| 8131.01 | 8153.05 | 8175.09 |
| 8192.54 | 8215.68 | 8238.82 |
| 8306.66 | 8314.70 | 8322.74 |
| 8353.19 | 8366.02 | 8378.85 |
| 8401.71 | 8411.17 | 8420.63 |
| 8420.71 | 8428.79 | 8436.87 |
| 8466.84 | 8474.84 | 8482.84 |
| 8483.32 | 8489.05 | 8494.77 |
| 8516.01 | 8528.96 | 8541.91 |
| 8555.29 | 8565.12 | 8574.94 |
| 8575.31 | 8592.03 | 8608.74 |
| 8650.35 | 8659.11 | 8667.86 |
| 8754.04 | 8766.76 | 8779.48 |
| 8799.09 | 8820.53 | 8841.97 |
| 8860.56 | 8871.76 | 8882.96 |
| 8882.98 | 8891.91 | 8900.84 |
| 8904.09 | 8925.16 | 8946.24 |
| 8954.36 | 8961.34 | 8968.33 |
| 8968.81 | 8978.23 | 8987.65 |
| 8988.02 | 8998.68 | 9009.33 |
| 9010.43 | 9019.53 | 9028.62 |
| 9028.78 | 9037.31 | 9045.84 |
| 9066.55 | 9077.91 | 9089.26 |
| 9089.32 | 9096.91 | 9104.51 |
| 9112.47 | 9133.46 | 9154.45 |
| 9196.31 | 9207.88 | 9219.45 |
| 9234.27 | 9243.94 | 9253.60 |
| 9254.17 | 9263.30 | 9272.44 |
| 9272.68 | 9289.41 | 9306.14 |
| 9308.35 | 9319.83 | 9331.31 |
| 9341.10 | 9374.82 | 9408.53 |
| 9411.21 | 9454.03 | 9496.84 |

| Left M/Z | Center M/Z | Right M/Z |
|---|---|---|
| 9560.23 | 9585.25 | 9610.26 |
| 9613.48 | 9626.56 | 9639.65 |
| 9639.94 | 9647.57 | 9655.20 |
| 9688.55 | 9723.57 | 9758.58 |
| 9903.45 | 9934.33 | 9965.21 |
| 10128.04 | 10139.87 | 10151.71 |
| 10152.46 | 10161.84 | 10171.22 |
| 10171.98 | 10184.57 | 10197.16 |
| 10197.54 | 10211.07 | 10224.60 |
| 10249.52 | 10262.23 | 10274.94 |
| 10295.62 | 10305.69 | 10315.75 |
| 10328.34 | 10350.14 | 10371.93 |
| 10435.64 | 10450.45 | 10465.26 |
| 10465.61 | 10482.62 | 10499.63 |
| 10518.75 | 10564.38 | 10610.01 |
| 10615.18 | 10638.37 | 10661.56 |
| 10711.79 | 10737.82 | 10763.85 |
| 10764.79 | 10775.15 | 10785.51 |
| 10828.47 | 10847.99 | 10867.50 |
| 10951.44 | 10963.37 | 10975.30 |
| 11028.77 | 11056.40 | 11084.03 |
| 11090.89 | 11107.43 | 11123.96 |
| 11132.45 | 11152.43 | 11172.40 |
| 11285.82 | 11305.10 | 11324.39 |
| 11378.42 | 11392.26 | 11406.11 |
| 11428.16 | 11442.74 | 11457.32 |
| 11468.24 | 11485.30 | 11502.35 |
| 11513.71 | 11530.99 | 11548.26 |
| 11567.26 | 11584.42 | 11601.59 |
| 11611.34 | 11634.82 | 11658.30 |
| 11670.69 | 11686.46 | 11702.22 |
| 11719.74 | 11732.72 | 11745.69 |
| 11746.38 | 11756.13 | 11765.89 |
| 11769.80 | 11786.10 | 11802.40 |
| 11826.75 | 11843.48 | 11860.20 |
| 11876.81 | 11889.88 | 11902.95 |
| 11903.39 | 11913.25 | 11923.11 |
| 11927.82 | 11938.26 | 11948.69 |
| 11974.12 | 11997.34 | 12020.56 |
| 12084.48 | 12116.90 | 12149.32 |
| 12151.24 | 12160.63 | 12170.03 |
| 12266.86 | 12290.16 | 12313.47 |
| 12552.61 | 12629.48 | 12706.34 |
| 12723.06 | 12738.33 | 12753.59 |
| 12769.89 | 12789.06 | 12808.24 |
| 12834.49 | 12917.52 | 13000.55 |
| 13018.32 | 13031.40 | 13044.48 |
| 13049.54 | 13076.86 | 13104.18 |
| 13119.56 | 13135.29 | 13151.02 |
| 13265.30 | 13276.12 | 13286.94 |
| 13304.84 | 13325.96 | 13347.09 |
| 13351.99 | 13364.15 | 13376.31 |
| 13501.19 | 13524.33 | 13547.48 |
| 13554.22 | 13569.52 | 13584.82 |
| 13602.38 | 13612.58 | 13622.78 |
| 13708.20 | 13723.60 | 13739.00 |
| 13740.40 | 13762.02 | 13783.64 |
| 13783.92 | 13795.98 | 13808.04 |
| 13832.96 | 13846.00 | 13859.04 |
| 13860.73 | 13881.13 | 13901.52 |
| 13905.76 | 13917.74 | 13929.71 |
| 13929.96 | 13944.37 | 13958.78 |
| 13959.98 | 13981.28 | 14002.58 |
| 14014.11 | 14067.59 | 14121.06 |
| 14122.86 | 14174.53 | 14226.20 |
| 14229.93 | 14254.82 | 14279.70 |
| 14280.60 | 14301.90 | 14323.20 |
| 14401.51 | 14431.22 | 14460.94 |
| 14462.27 | 14541.41 | 14620.56 |
| 14623.06 | 14642.87 | 14662.69 |
| 14684.56 | 14699.66 | 14714.76 |
| 14764.89 | 14786.87 | 14808.84 |
| 14859.96 | 14882.15 | 14904.35 |
| *15114.72 | 15136.98 | 15159.25 |
| *15321.76 | 15344.32 | 15366.88 |
| *15856.28 | 15879.62 | 15902.96 |
| *16066.16 | 16087.64 | 16109.12 |
| 18248.47 | 18271.03 | 18293.59 |
| 18548.49 | 18570.16 | 18591.84 |
| 18603.02 | 18630.68 | 18658.34 |
| 18708.84 | 18730.03 | 18751.21 |
| 18811.43 | 18848.65 | 18885.87 |
| 19343.00 | 19378.06 | 19413.11 |
| 20886.02 | 21156.71 | 21427.39 |
| 21669.84 | 21804.69 | 21939.55 |
| 22526.70 | 22604.25 | 22641.79 |
| 22999.81 | 23033.14 | 23066.47 |
| 23097.51 | 23130.26 | 23163.02 |
| 23213.01 | 23246.92 | 23280.82 |
| 23305.86 | 23353.04 | 23400.22 |
| 23429.20 | 23467.05 | 23504.91 |
| 25144.70 | 25185.27 | 25225.84 |
| 25429.35 | 25473.61 | 25517.87 |
| 25519.61 | 25570.37 | 25621.14 |
| 25624.40 | 25686.01 | 25747.63 |
| 27915.48 | 27962.78 | 28010.08 |
| 28037.85 | 28133.53 | 28229.20 |
| 28237.01 | 28338.55 | 28440.09 |
| 28800.67 | 28859.90 | 28919.13 |
| 28924.34 | 28972.72 | 29021.10 |
| 29030.65 | 29078.60 | 29126.55 | c) operating on the mass spectrometry data with a programmed computer implementing a first classifier and a second classifier (Classifiers A and D, respectively), wherein Classifier A is defined by:

a) a first reference set of class labeled integrated intensity mass spectral feature values for a set of mass spectral features comprising mass spectral features selected from a list of mass spectral features:

| Left M/Z | Center M/Z | Right M/Z |
|---|---|---|
| 5998.01 | 6008.58 | 6019.14 |
| 8192.54 | 8215.68 | 8238.82 |
| 5922.62 | 5934.73 | 5946.84 |
| 11428.16 | 11442.74 | 11457.32 |
| 5162.99 | 5185.8 | 5208.61 |
| 14764.89 | 14786.87 | 14808.84 |
| 11876.81 | 11889.88 | 11902.95 |
| 3149.02 | 3156.94 | 3164.86 |
| 5786.29 | 5794.96 | 5803.62 |
| 13783.92 | 13795.98 | 13808.04 |
| 10828.47 | 10847.99 | 10867.5 |
| 11513.71 | 11530.99 | 11548.26 |
| 3384.77 | 3396.02 | 3407.27 |
| 6165.75 | 6175.04 | 6184.34 |
| 23305.86 | 23353.04 | 23400.22 |
| 3165.7 | 3177.13 | 3188.57 |
| 3877.78 | 3888.14 | 3898.49 |
| 14859.96 | 14882.15 | 14904.35 |
| 3099.64 | 3111.21 | 3122.77 |
| 5743.56 | 5750.24 | 5756.93 |
| 11903.39 | 11913.25 | 11923.11 |
| 9903.45 | 9934.33 | 9965.21 |
| 11974.12 | 11997.34 | 12020.56 |
| 5685.16 | 5693.39 | 5701.62 |
| 11028.77 | 11056.4 | 11084.03 |
| 4633.75 | 4642.42 | 4651.09 |
| 5726.03 | 5734.42 | 5742.81 |
| 11567.26 | 11584.42 | 11601.59 |
| 11826.75 | 11843.48 | 11860.2 | associated with immune response type 2, the feature values obtained by conducting mass spectrometry on a development set of blood-based samples obtained from a first population of non-small cell lung cancer patients treated with an anti-PD-1 drug; and b) parameters defining a classification procedure for generating a class label for the mass spectrometry data of the blood-based sample of the cancer patient by comparing the integrated intensity values of features associated with immune response type 2 in the mass spectrometry data of the blood-based sample of the cancer patient with the first reference set of Classifier A;

wherein Classifier D is defined by:

a) a second reference set of class labeled integrated intensity mass spectral feature values for a set of mass spectral features comprising mass spectral features selected from a list of mass spectral features:

| Left M/Z | Center M/Z | Right M/Z |
|---|---|---|
| 3071.22 | 3085.19 | 3099.16 |
| 3099.64 | 3111.21 | 3122.77 |
| 3125.22 | 3137.00 | 3148.78 |
| 3149.02 | 3156.94 | 3164.86 |
| 3165.70 | 3177.13 | 3188.57 |
| 3189.67 | 3198.85 | 3208.03 |
| 3208.33 | 3216.82 | 3225.30 |
| 3231.00 | 3243.53 | 3256.07 |
| 3256.90 | 3267.00 | 3277.10 |
| 3305.44 | 3314.98 | 3324.51 |
| 3353.79 | 3366.37 | 3378.94 |
| 3384.77 | 3396.02 | 3407.27 |
| 3410.04 | 3422.21 | 3434.37 |
| 3434.51 | 3443.90 | 3453.30 |
| 3454.74 | 3466.38 | 3478.02 |
| 3540.72 | 3555.53 | 3570.35 |
| 3583.14 | 3593.09 | 3603.05 |
| 3667.06 | 3681.88 | 3696.70 |
| 3697.35 | 3705.33 | 3713.31 |
| 3747.09 | 3755.81 | 3764.52 |
| 3766.63 | 3776.40 | 3786.17 |
| 3811.87 | 3821.31 | 3830.74 |
| 3832.00 | 3841.64 | 3851.28 |
| 3860.09 | 3867.51 | 3874.93 |
| 3877.78 | 3888.14 | 3898.49 |
| 3899.28 | 3907.43 | 3915.58 |
| 3915.70 | 3927.75 | 3939.80 |
| 3943.30 | 3952.26 | 3961.21 |
| 3999.11 | 4011.41 | 4023.71 |
| 4023.91 | 4031.43 | 4038.96 |
| 4039.25 | 4051.40 | 4063.54 |
| 4080.14 | 4094.83 | 4109.53 |
| 4112.17 | 4119.37 | 4126.57 |
| 4127.25 | 4133.39 | 4139.52 |
| 4198.95 | 4210.81 | 4222.68 |
| 4258.83 | 4266.50 | 4274.18 |
| 4276.79 | 4289.24 | 4301.69 |
| 4332.05 | 4341.63 | 4351.22 |
| 4351.40 | 4359.83 | 4368.27 |
| 4372.40 | 4381.03 | 4389.66 |
| 4397.29 | 4407.28 | 4417.26 |
| 4427.40 | 4433.22 | 4439.04 |
| 4439.75 | 4443.96 | 4448.18 |
| 4449.38 | 4461.23 | 4473.07 |
| 4502.53 | 4508.75 | 4514.98 |
| 4553.30 | 4565.57 | 4577.84 |
| 4580.87 | 4586.84 | 4592.81 |
| 4593.22 | 4599.59 | 4605.96 |
| 4618.51 | 4625.99 | 4633.46 |
| 4633.75 | 4642.42 | 4651.09 |
| 4667.54 | 4679.99 | 4692.43 |
| 4698.76 | 4713.31 | 4727.86 |
| 4747.49 | 4755.82 | 4764.15 |
| 4770.57 | 4776.34 | 4782.12 |
| 4782.62 | 4790.85 | 4799.08 |
| 4807.16 | 4819.05 | 4830.95 |
| 4845.90 | 4857.70 | 4869.49 |
| 4885.05 | 4893.33 | 4901.61 |
| 4910.19 | 4919.12 | 4928.06 |
| 4928.26 | 4938.24 | 4948.23 |
| 4949.44 | 4964.30 | 4979.15 |
| 4989.38 | 5000.07 | 5010.76 |
| 5012.17 | 5020.40 | 5028.63 |
| 5033.64 | 5041.17 | 5048.71 |
| 5048.95 | 5054.98 | 5061.00 |
| 5061.10 | 5070.88 | 5080.67 |
| 5093.87 | 5106.47 | 5119.06 |
| 5120.38 | 5127.97 | 5135.56 |
| 5162.99 | 5185.80 | 5208.61 |
| 5209.58 | 5224.44 | 5239.30 |
| 5240.40 | 5251.05 | 5261.69 |
| 5274.04 | 5288.09 | 5302.14 |
| 5351.59 | 5362.36 | 5373.12 |
| 5396.97 | 5404.07 | 5411.16 |
| 5411.52 | 5418.07 | 5424.63 |
| 5424.89 | 5431.54 | 5438.18 |
| 5442.72 | 5449.54 | 5456.36 |
| 5512.62 | 5520.50 | 5528.38 |
| 5540.44 | 5552.25 | 5564.06 |
| 5564.15 | 5573.62 | 5583.09 |
| 5685.16 | 5693.39 | 5701.62 |
| 5701.82 | 5708.30 | 5714.77 |
| 5714.97 | 5720.49 | 5726.01 |
| 5726.03 | 5734.42 | 5742.81 |
| 5743.56 | 5750.24 | 5756.93 |
| 5757.29 | 5764.16 | 5771.03 |
| 5771.12 | 5778.62 | 5786.11 |
| 5786.29 | 5794.96 | 5803.62 |
| 5803.89 | 5810.08 | 5816.27 |
| 5816.42 | 5822.76 | 5829.11 |
| 5832.02 | 5840.46 | 5848.89 |
| 5850.08 | 5863.91 | 5877.73 |
| 5879.59 | 5888.74 | 5897.90 |
| 5898.07 | 5909.77 | 5921.47 |
| 5922.62 | 5934.73 | 5946.84 |
| 5949.41 | 5963.90 | 5978.40 |
| 5978.83 | 5987.76 | 5996.69 |
| 5998.01 | 6008.58 | 6019.14 |
| 6020.13 | 6028.93 | 6037.72 |
| 6054.61 | 6061.94 | 6069.27 |
| 6069.47 | 6082.86 | 6096.26 |
| 6099.57 | 6109.12 | 6118.68 |
| 6134.48 | 6148.68 | 6162.88 |
| 6165.75 | 6175.04 | 6184.34 |
| 6186.65 | 6194.45 | 6202.25 |
| 6202.33 | 6209.35 | 6216.38 |
| 6216.68 | 6224.86 | 6233.04 |
| 6275.16 | 6284.15 | 6293.14 |
| 6293.16 | 6301.49 | 6309.82 |
| 6322.27 | 6331.46 | 6340.64 |
| 6378.77 | 6393.09 | 6407.42 |
| 6409.41 | 6479.04 | 6548.68 |
| 6553.89 | 6564.68 | 6575.47 |
| 6575.85 | 6589.26 | 6602.67 |
| 6604.74 | 6675.06 | 6745.39 |
| 6779.07 | 6798.12 | 6817.17 |
| 6825.83 | 6837.67 | 6849.52 |
| 6849.89 | 6859.44 | 6868.99 |
| 6869.08 | 6878.92 | 6888.75 |
| 6889.03 | 6896.99 | 6904.95 |
| 6911.60 | 6920.97 | 6930.34 |
| 6930.88 | 6939.55 | 6948.22 |
| 6948.87 | 6956.18 | 6963.49 |
| 6963.58 | 6971.11 | 6978.64 |
| 6979.01 | 6995.27 | 7011.52 |
| 7011.77 | 7019.83 | 7027.88 |
| 7029.37 | 7033.60 | 7037.84 |
| 7037.91 | 7046.82 | 7055.73 |
| 7055.81 | 7060.15 | 7064.50 |
| 7065.49 | 7072.90 | 7080.31 |
| 7118.24 | 7143.95 | 7169.66 |
| 7178.66 | 7189.32 | 7199.97 |
| 7234.04 | 7243.67 | 7253.30 |
| 7279.59 | 7292.85 | 7306.11 |

| Left M/Z | Center M/Z | Right M/Z |
|---|---|---|
| 7309.51 | 7318.12 | 7326.73 |
| 7327.41 | 7332.74 | 7338.06 |
| 7375.19 | 7390.07 | 7404.95 |
| 7406.19 | 7448.51 | 7490.84 |
| *7553.58 | 7566.50 | 7579.42 |
| *7659.19 | 7672.34 | 7685.48 |
| 7731.02 | 7736.79 | 7742.56 |
| 7742.75 | 7751.34 | 7759.93 |
| 7760.24 | 7767.77 | 7775.30 |
| 7776.52 | 7788.92 | 7801.31 |
| 7803.18 | 7820.32 | 7837.46 |
| *7924.01 | 7937.38 | 7950.75 |
| 7984.80 | 7994.91 | 8005.01 |
| 8006.66 | 8018.69 | 8030.72 |
| *8030.75 | 8041.85 | 8052.96 |
| 8131.01 | 8153.05 | 8175.09 |
| 8192.54 | 8215.68 | 8238.82 |
| 8306.66 | 8314.70 | 8322.74 |
| 8353.19 | 8366.02 | 8378.85 |
| 8401.71 | 8411.17 | 8420.63 |
| 8420.71 | 8428.79 | 8436.87 |
| 8466.84 | 8474.84 | 8482.84 |
| 8483.32 | 8489.05 | 8494.77 |
| 8516.01 | 8528.96 | 8541.91 |
| 8555.29 | 8565.12 | 8574.94 |
| 8575.31 | 8592.03 | 8608.74 |
| 8650.35 | 8659.11 | 8667.86 |
| 8754.04 | 8766.76 | 8779.48 |
| 8799.09 | 8820.53 | 8841.97 |
| 8860.56 | 8871.76 | 8882.96 |
| 8882.98 | 8891.91 | 8900.84 |
| 8904.09 | 8925.16 | 8946.24 |
| 8954.36 | 8961.34 | 8968.33 |
| 8968.81 | 8978.23 | 8987.65 |
| 8988.02 | 8998.68 | 9009.33 |
| 9010.43 | 9019.53 | 9028.62 |
| 9028.78 | 9037.31 | 9045.84 |
| 9066.55 | 9077.91 | 9089.26 |
| 9089.32 | 9096.91 | 9104.51 |
| 9112.47 | 9133.46 | 9154.45 |
| 9196.31 | 9207.88 | 9219.45 |
| 9234.27 | 9243.94 | 9253.60 |
| 9254.17 | 9263.30 | 9272.44 |
| 9272.68 | 9289.41 | 9306.14 |
| 9308.35 | 9319.83 | 9331.31 |
| 9341.10 | 9374.82 | 9408.53 |
| 9411.21 | 9454.03 | 9496.84 |
| 9560.23 | 9585.25 | 9610.26 |
| 9613.48 | 9626.56 | 9639.65 |
| 9639.94 | 9647.57 | 9655.20 |
| 9688.55 | 9723.57 | 9758.58 |
| 9903.45 | 9934.33 | 9965.21 |
| 10128.04 | 10139.87 | 10151.71 |
| 10152.46 | 10161.84 | 10171.22 |
| 10171.98 | 10184.57 | 10197.16 |
| 10197.54 | 10211.07 | 10224.60 |
| 10249.52 | 10262.23 | 10274.94 |
| 10295.62 | 10305.69 | 10315.75 |
| 10328.34 | 10350.14 | 10371.93 |
| 10435.64 | 10450.45 | 10465.26 |
| 10465.61 | 10482.62 | 10499.63 |
| 10518.75 | 10564.38 | 10610.01 |
| 10615.18 | 10638.37 | 10661.56 |
| 10711.79 | 10737.82 | 10763.85 |
| 10764.79 | 10775.15 | 10785.51 |
| 10828.47 | 10847.99 | 10867.50 |
| 10951.44 | 10963.37 | 10975.30 |
| 11028.77 | 11056.40 | 11084.03 |
| 11090.89 | 11107.43 | 11123.96 |
| 11132.45 | 11152.43 | 11172.40 |
| 11285.82 | 11305.10 | 11324.39 |
| 11378.42 | 11392.26 | 11406.11 |
| 11428.16 | 11442.74 | 11457.32 |
| 11468.24 | 11485.30 | 11502.35 |
| 11513.71 | 11530.99 | 11548.26 |
| 11567.26 | 11584.42 | 11601.59 |
| 11611.34 | 11634.82 | 11658.30 |
| 11670.69 | 11686.46 | 11702.22 |
| 11719.74 | 11732.72 | 11745.69 |
| 11746.38 | 11756.13 | 11765.89 |
| 11769.80 | 11786.10 | 11802.40 |
| 11826.75 | 11843.48 | 11860.20 |
| 11876.81 | 11889.88 | 11902.95 |
| 11903.39 | 11913.25 | 11923.11 |
| 11927.82 | 11938.26 | 11948.69 |
| 11974.12 | 11997.34 | 12020.56 |
| 12084.48 | 12116.90 | 12149.32 |
| 12151.24 | 12160.63 | 12170.03 |
| 12266.86 | 12290.16 | 12313.47 |
| 12552.61 | 12629.48 | 12706.34 |
| 12723.06 | 12738.33 | 12753.59 |
| 12769.89 | 12789.06 | 12808.24 |
| 12834.49 | 12917.52 | 13000.55 |
| 13018.32 | 13031.40 | 13044.48 |
| 13049.54 | 13076.86 | 13104.18 |
| 13119.56 | 13135.29 | 13151.02 |
| 13265.30 | 13276.12 | 13286.94 |
| 13304.84 | 13325.96 | 13347.09 |
| 13351.99 | 13364.15 | 13376.31 |
| 13501.19 | 13524.33 | 13547.48 |
| 13554.22 | 13569.52 | 13584.82 |
| 13602.38 | 13612.58 | 13622.78 |
| 13708.20 | 13723.60 | 13739.00 |
| 13740.40 | 13762.02 | 13783.64 |
| 13783.92 | 13795.98 | 13808.04 |
| 13832.96 | 13846.00 | 13859.04 |
| 13860.73 | 13881.13 | 13901.52 |
| 13905.76 | 13917.74 | 13929.71 |
| 13929.96 | 13944.37 | 13958.78 |
| 13959.98 | 13981.28 | 14002.58 |
| 14014.11 | 14067.59 | 14121.06 |
| 14122.86 | 14174.53 | 14226.20 |
| 14229.93 | 14254.82 | 14279.70 |
| 14280.60 | 14301.90 | 14323.20 |
| 14401.51 | 14431.22 | 14460.94 |
| 14462.27 | 14541.41 | 14620.56 |
| 14623.06 | 14642.87 | 14662.69 |
| 14684.56 | 14699.66 | 14714.76 |
| 14764.89 | 14786.87 | 14808.84 |
| 14859.96 | 14882.15 | 14904.35 |
| *15114.72 | 15136.98 | 15159.25 |
| *15321.76 | 15344.32 | 15366.88 |
| *15856.28 | 15879.62 | 15902.96 |
| *16066.16 | 16087.64 | 16109.12 |
| 18248.47 | 18271.03 | 18293.59 |
| 18548.49 | 18570.16 | 18591.84 |
| 18603.02 | 18630.68 | 18658.34 |
| 18708.84 | 18730.03 | 18751.21 |
| 18811.43 | 18848.65 | 18885.87 |
| 19343.00 | 19378.06 | 19413.11 |
| 20886.02 | 21156.71 | 21427.39 |
| 21669.84 | 21804.69 | 21939.55 |
| 22566.70 | 22604.25 | 22641.79 |
| 22999.81 | 23033.14 | 23066.47 |
| 23097.51 | 23130.26 | 23163.02 |
| 23213.01 | 23246.92 | 23280.82 |
| 23305.86 | 23353.04 | 23400.22 |
| 23429.20 | 23467.05 | 23504.91 |
| 25144.70 | 25185.27 | 25225.84 |
| 25429.35 | 25473.61 | 25517.87 |
| 25519.61 | 25570.37 | 25621.14 |
| 25624.40 | 25686.01 | 25747.63 |
| 27915.48 | 27962.78 | 28010.08 |
| 28037.85 | 28133.53 | 28229.20 |
| 28237.01 | 28338.55 | 28440.09 |
| 28800.67 | 28859.90 | 28919.13 |
| 28924.34 | 28972.72 | 29021.10 |
| 29030.65 | 29078.60 | 29126.55 | the feature values obtained by conducting mass spectrometry on a development set of blood-based samples obtained from a second population of melanoma patients treated with an anti-PD-1 drug; and
  b) parameters defining a classification procedure for generating a class label for the mass spectrometry data of the blood-based sample of the cancer patient by comparing the integrated intensity values of features in the mass spectrometry data of the blood-based sample of the cancer patient with the second reference set of Classifier D;
  wherein in the operating step the classifiers A and D compare the integrated intensity values with the feature values of the first and second reference sets in accordance with the classification procedures of classifiers A and D and detect a first class label for the sample.

16. The method of claim 15, wherein classifiers A and D are obtained from filtered mini-classifiers combined using a regularized combination method.

17. The method of claim 15, further comprising operating on the mass spectrometry data with the programmed computer implementing the second classifier (Classifier D) and a third classifier (Classifier B),
wherein Classifier B is defined by:
  a) a third reference set of integrated intensity mass spectral feature values for a set of mass spectral features, the feature values obtained by conducting mass spectrometry on a development set of blood-based samples obtained from a third population of non-small cell lung cancer patients treated with an anti-PD1 drug; and
  b) parameters defining a classification procedure for generating a class label for the mass spectrometry data of the blood-based sample of the cancer patient by comparing the integrated intensity values of features in the mass spectrometry data of the blood-based sample of the cancer patient with the third reference set of Classifier B; and
  wherein in the operating step the classifiers D and B compare the integrated intensity values with the feature values of the second and third reference sets in accordance with the classification procedures of classifiers D and B and detect a second class label for the sample.

18. A testing apparatus comprising, in combination:
a mass spectrometer configured to conduct mass spectrometry on a blood-based sample obtained from a cancer patient and obtaining a mass spectrum in the form of a set of integrated intensity values for a multitude of features in the mass spectrum;
a processing unit, and
a nontransitory computer memory storing instructions and classification parameters for at least a first classifier, a second classifier, and a third classifier (Classifiers A, B, and D, respectively), for execution by the processing unit,
wherein Classifier A is defined by:
  a) a first reference set of integrated intensity mass spectral feature values for a set of mass spectral features associated with immune response type 2, the feature values obtained by conducting mass spectrometry on a development set of blood-based samples obtained from a first population of non-small cell lung cancer patients treated with an anti-PD1 drug; wherein the set of mass spectral features associated with immune response type 2 comprise a list of features:

| Left M/Z | Center M/Z | Right M/Z |
|---|---|---|
| 5998.01 | 6008.58 | 6019.14 |
| 8192.54 | 8215.68 | 8238.82 |
| 5922.62 | 5934.73 | 5946.84 |
| 11428.16 | 11442.74 | 11457.32 |
| 5162.99 | 5185.8 | 5208.61 |
| 14764.89 | 14786.87 | 14808.84 |
| 11876.81 | 11889.88 | 11902.95 |
| 3149.02 | 3156.94 | 3164.86 |
| 5786.29 | 5794.96 | 5803.62 |
| 13783.92 | 13795.98 | 13808.04 |
| 10828.47 | 10847.99 | 10867.5 |
| 11513.71 | 11530.99 | 11548.26 |
| 3384.77 | 3396.02 | 3407.27 |
| 6165.75 | 6175.04 | 6184.34 |
| 23305.86 | 23353.04 | 23400.22 |
| 3165.7 | 3177.13 | 3188.57 |
| 3877.78 | 3888.14 | 3898.49 |
| 14859.96 | 14882.15 | 14904.35 |
| 3099.64 | 3111.21 | 3122.77 |
| 5743.56 | 5750.24 | 5756.93 |
| 11903.39 | 11913.25 | 11923.11 |
| 9903.45 | 9934.33 | 9965.21 |
| 11974.12 | 11997.34 | 12020.56 |
| 5685.16 | 5693.39 | 5701.62 |
| 11028.77 | 11056.4 | 11084.03 |
| 4633.75 | 4642.42 | 4651.09 |
| 5726.03 | 5734.42 | 5742.81 |
| 11567.26 | 11584.42 | 11601.59 |
| 11826.75 | 11843.48 | 11860.2 | and
b) parameters defining a classification procedure for generating a class label for the mass spectrum of the blood-based sample of the cancer patient by comparing the integrated intensity values of features associated with immune response type 2 in the mass spectrum of the blood-based sample of the cancer patient with the first reference set of Classifier A;
wherein Classifier B is defined by:
  a) a third reference set of integrated intensity mass spectral feature values for a set of mass spectral features, the feature values obtained by conducting mass spectrometry on a development set of blood-based samples obtained from a third population of non-small cell lung cancer patients treated with an anti-PD1 drug; and
  b) parameters defining a classification procedure for generating a class label for the mass spectrum of the blood-based sample of the cancer patient by comparing the integrated intensity values of features in the mass spectrum of the blood-based sample of the cancer patient with the third reference set of Classifier B;
wherein Classifier D is defined by:
  a) a second reference set of integrated intensity mass spectral feature values for a set of mass spectral features, the feature values obtained by conducting mass spectrometry on a development set of blood-based samples obtained from a second population of melanoma patients treated with an anti-PD1 drug; and
  b) parameters defining a classification procedure for generating a class label for the mass spectrum of the blood-based sample of the cancer patient by comparing the integrated intensity values of features in the mass spectrum of the blood-based sample of the cancer patient with the second reference set of Classifier D;
and program logic for combining the outputs of the classification labels produced by Classifiers A, B and D in a ternary classification schema, wherein the program logic combining outputs of the classification labels produced by Classifiers A, B, and D generates a Good class label which is correlated to a prediction of good outcome on immune monotherapy.

19. The apparatus of claim 18, wherein each of the Classifiers comprise a combination of filtered mini-Classifiers combined using a regularized combination method.

* * * * *